(12) United States Patent
Milligan et al.

(10) Patent No.: US 10,548,994 B1
(45) Date of Patent: Feb. 4, 2020

(54) CONTROL OF CHRONIC NEUROPATHIC PAIN AND ALLODYNIA

(71) Applicant: STC.UNM, Albuquerque, NM (US)

(72) Inventors: Erin Damita Milligan, Placitas, NM (US); Jeffrey P. Norenberg, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 145 days.

(21) Appl. No.: 14/196,343

(22) Filed: Mar. 4, 2014

Related U.S. Application Data

(60) Provisional application No. 61/775,789, filed on Mar. 11, 2013, provisional application No. 61/875,264, filed on Sep. 9, 2013, provisional application No. 61/901,864, filed on Nov. 8, 2013.

(51) Int. Cl.
| | |
|---|---|
| *A61K 31/4166* | (2006.01) |
| *A61K 51/04* | (2006.01) |
| *A61K 31/4174* | (2006.01) |
| *A61K 38/18* | (2006.01) |
| *A61K 38/20* | (2006.01) |
| *A61K 38/34* | (2006.01) |

(52) U.S. Cl.
CPC ...... *A61K 51/0453* (2013.01); *A61K 31/4174* (2013.01); *A61K 38/1841* (2013.01); *A61K 38/2013* (2013.01); *A61K 38/2026* (2013.01); *A61K 38/2066* (2013.01); *A61K 38/2086* (2013.01); *A61K 38/34* (2013.01)

(58) Field of Classification Search
None
See application file for complete search history.

(56) References Cited

U.S. PATENT DOCUMENTS

| | | | | |
|---|---|---|---|---|
| 7,179,893 B2* | 2/2007 | Le | ......... | A61K 31/167 435/326 |
| 2005/0107399 A1* | 5/2005 | Boman | ......... | A61K 31/416 514/255.06 |

OTHER PUBLICATIONS

Milligan, Erin D., et al. "Repeated intrathecal injections of plasmid DNA encoding interleukin-10 produce prolonged reversal of neuropathic pain." Pain 126.1 (2006): 294-308.*
Ashley, Carlee E., et al. "The targeted delivery of multicomponent cargos to cancer cells by nanoporous particle-supported lipid bilayers." Nature materials 10.5 (2011): 389-397.*
Plunkett, Jeffery A., et al. "Effects of interleukin-10 (IL-10) on pain behavior and gene expression following excitotoxic spinal cord injury in the rat." Experimental neurology 168.1 (2001): 144-154.*
Scholz, Joachim, et al. "Low-dose methotrexate reduces peripheral nerve injury-evoked spinal microglial activation and neuropathic pain behavior in rats." Pain 138.1 (2008): 130-142. (Year: 2008).*
Parkitna, J. Rodriguez, et al. "Comparison of Gene Expression Profiles in Neuropathic and Inflammatory Pain." Journal of Physiology and Pharmacology 57.3 (2006): 401-414. (Year: 2006).*
Isaksson, Jonas, et al. "Expression of ICAM-1 and CD11b after experimental spinal cord injury in rats." Journal of neurotrauma 16.2 (1999): 165-173. (Year: 1999).*
Agrawal S, Kandimalla ER. Modulation of Toll-like Receptor 9 Responses through Synthetic Immunostimulatory Motifs of DNA. Ann N Y Acad Sci, 2003;1002:30-42.
Agrawal S, Kandimalla ER. Synthetic agonists of Toll-like receptors 7, 8 and 9. Biochem Soc Trans, 2007;35(pt 6): 1461-1467.
Amiji MM. Polymeric Gene Delivery: Principles and Applications. Boca Raton: CRC Press, 2005, Table of contents only.
Asensio, VS, Campbell IL. Chemokines in the CNS: plurifunctional mediators in diverse states. Trends in Neuroscience, 1999;22:504-512.
Beletskii A, et al. High-throughput phagocytosis assay utilizing a pH-sensitive fluorescent dye. Biotechniques, 2005;39(6):894-897.
Beutler AS, et al. Intrathecal gene transger by adeno-associated virus for pain. Current Opinion in Molecular therapeutics, 2005;7(5): 431-439.
Beutler B, Wagner H. Toll-Like Receptor Family Members and Their Ligands. Current Topics in Microbiology and Immunology, ed RW Compans, et al. vol. 270. 2002, New York: Springer, Table of contents only.
Bandhonneur N, et al. Specific and non-specific phagocytosis of ligand-grafted PLGA microspheres by macrophages. Eur J Pharm Sci, 2009;36(4-5):474-485.

(Continued)

*Primary Examiner* — Nissa M Westerberg
(74) *Attorney, Agent, or Firm* — Henry D. Coleman; R. Neil Sudol

(57) ABSTRACT

In one embodiment, the invention provides a method of treating a subject suffering from chronic neuropathic pain and/or allodynia by administering a therapeutically-effective amount of at least one LFA1 antagonist to the subject. In a preferred embodiment, the invention provides a method of treating a subject suffering from chronic neuropathic pain and/or allodynia, the method comprising administering intrathecally to the subject a therapeutically-effective amount of microparticles comprising PLGA-encapsulated pDNA-IL-10, optionally in combination with a therapeutically-effective amount of intrathecally-administered CpG oligodeoxynucleotide (CpG ODN) and/or at least one LFA1 antagonist.

26 Claims, 26 Drawing Sheets
(19 of 26 Drawing Sheet(s) Filed in Color)

(56) References Cited

OTHER PUBLICATIONS

Braun JS, et al. Cellular components of the immune barrier in the spinal meninges and dorsal root ganglia of the normal rat: Immunohistochemical (MHC class II) and electron-microscopic observations. Cell Tissue Res, 1992;273:209-217.
Bruijns RH, Bult H. Effects of local cytochalasin D delivery on smooth muscle cell migration and on collar-induced intimal hyperplasia in the rabbit carotid artery. Br J Pharmacol, 2001;134(3):473-483.
Buechler C, et al. Regulation of scavenger receptor CD163 expression in human monocytes and macrophages by pro- and anti-inflammatory stimuli. J Leukoc Biol, 2000;67(1):97-103.
Busha D, et al. Spinal cord gene transfer using naked plasmid DNA coding the anti-inflammatory gene, Interleukin-10 (IL10) leads to long-term reversal of thermal hyperalgesia in chronic constriction injury (CCI) rats. 25th Annual Scientific Meeting of the American Pain Society, 2006; San Antionio, TX: Elsevier.
Carter PH, et al. Capped diaminopropionamide-glycine dipeptides are inhibitors of CC chemokinereceptor 2 (CCR2). Bioorg Med Chem Lett, 2007;17(19):5455-5461.
Chacur M, et al. Snake venome components enhance pain upon subcutaneous injection: an initial examination of spinal cord mediators. Pain, 2004;111:65-76.
Chacur M, et al. Snake venom phospholipase A2s (Asp49 and Lys49) induce mechanical allodyniaupon peri-sciatic administration: involvement of spinal cord glia, proinflammatory cytokines and nitricoxide. Pain, 2004;108:180-191.
Chao CC, et al. Interleukin-1 and tumor necrosis factor-alpha synergistically mediate neurotoxicity: involvement of nitric oxide and N-methyl-D-aspartate receptors. Brain Behav Immunol, 1995;9:355-365.
Chaplan SR, et al. Quantitative assessment of tactile allodynia in the rat paw. J Neurosci Meth, 1994;53:55-63.
Cherney RJ, et al. Discovery of trisubstituted cyclohexanes as potent cc chemokine receptor 2 (CCR2) antagonists. Bioorg Med Chem Lett, 2009;19(3):597-601.
Costigan M, Scholz J, Woolf CJ. Neuropathic pain: a maladaptive response of the nervous system to damage. Annu Rev Neurosci, 2009;32:1-32.
Cotton M, et al. Lipopolysaccharide is a frequent contaminant of plasmid DNA preparation and can be toxic to primary human cells in the presence of adenovirus. Gene Therapy, 1994;1:239-246.
Dansereau MA, et al. Spinal CCL2 pronociceptive action is no longer effective in CCR2 receptor antagonist-treated rats. J Neurochem, 2008;106(2):757-769.
Diez S, Tros De Ilarduya C. Versatility of biodegradable poly(D,L-lactic-co-glycolic acid) microspheres for plasmid DNA delivery. Eur J Pharm Biopharm, 2006;63(2):188-197.
Dougherty PM, et al. Taxol-induced sensory disturbance is characterized by preferential impairment of myelinated fiber function in cancer patients. Pain, 2004;109(1-2):132-142.
Dromard C, et al. Adult human spinal cord harbors neural precursor cells that generate neurons and glial cells in vitro. J Neurosci Res, 2008;86(9):1916-1926.
Dubovy P, et al. Increased invasion of ED-1 positive macrophages in both ipsi- and contraleteral dorsal root ganglia following unilateral nerve injuries. Neurosci Lett, 2007;427(2):88-93.
Edelstein ML, et al. Gene therapy clinical trials worldwide: 1989-2004—an overview. Journal of Gene Medicine, 2004;6:597-602.
Fonnum F, Johnsen A, Hassel B. Use of fluorocitrate and fluoroacetate in the study of brain metabolism. Glia, 1997;21:106-113.
Ghosh TK, et al. Toll-like receptor (TLR) 2-9 agonists-induced cytokines and chemokines: I. Comparison with T cell receptor-induced responses. Cell Immunol, 2006;243(1):48-57.
Glover DJ, Lipps HJ, Jans DA. Towards safe, non-viral therapeutic gene expression in humans. Nat Reviews Genetics, 2005;6:299-310.
Gordon S. Alternative activation of macrophages. Nat Rev, 2003;3:23-35.
Goss JR, Goins WF, Glorioso JC. Gene therapy application for the treatment of neuropathic pain. Expert Rev Neurotherapeutics, 2007;7(5):487-506.
Goss JR, et al. Antinociceptive effect of a genomic herpes simplex virus-based vector expressing human proenkephalin in rat dorsal root ganglion. Gene Ther, 2001;8:551-556.
Gratchev A, et al. Alternatively activated antigen-presenting cells: molecular repertoire, immune regulation, and healing. Skin Pharmacol Appl Skin Physiol, 2001;14(5):272-279.
Hacker H, et al. Specificity in Toll-like receptor signaling through distinct effector functions of TRAF3 and TRAF6. Nature, 2006;439(7073):204-207.
Haghighi AB, et al. CSF levels of cytokines in neuro-Behcet's disease. Clin Neurol Neurosurg, 2009;111(6):507-510.
Hagihara Y, et al. Long-term functional assessment of encapsulated cells transfected with Tet-On system. Cell Transplant, 1999;8:431-434.
Haines DE, Harkey HL, Al-Mefty O. The "subdural" space: a new look at an outdated concept. Neurosurgery, 1993;32(1):111-120.
Hassel B, et al. Selective inhibition of glial cell metabolism by fluorocitrate. Brain Res, 1992;249:120-124.
Haydon PG. GLIA: Listening and talking to the synapse. Nat Rev Neurosci, 2001;2:185-193.
Hedley ML. Formulations containing poly-lactide-co-glycolide and plasmid DNA expression vectors. Exper Opin Biol Ther, 2003;3(6):903-910.
Hoerner PJ, et al. Proliferation and differentiation of progenitor cells throughout the intact adult rat spinal cord. J Neurosci, 2000;20(6):2218-2228.
Hu P, McLachlan EM. Macrophage and lymphocyte invasion of dorsal root ganglia after peripheral nerve lesions in the rat. Neuroscience, 2002;112(1):23-38.
Hua XY, et al. Intrathecal minocycline. Attenuates peripheral inflammation-induced hyperalgesia by inhibiting p38 MAPK in spinal microglia. Eur J Neurosci, 2005;22:2431-2440.
Huang D, et al. The neural chemokine CX3CL1/fractalkine selectively recruits NK cells that modify experimental autoimmune encephalomyelitis within the central nervous system. FASEB J, 2006;20:896-905.
Hughes TS, et al. Intrathecal injection of nake plasmid DNA provides long-term expression of secreted proteins. Mol Ther, 2009;17(1):88-94.
Hughes TS, et al. Immunogenicity of intrathecal plasmid gene delivery: cytokine release and effect on transgene expression. J Gene Med, 2009;17(1):782-790.
Hutchinson MR, et al. Minocycline suppresses morphine-induced respiratory depression, suppresses morphine-induced reward, and enhances systemic morphine-induced analgesia. Brain Behav Immun, 2008. in press.
Juang H, et al. Monocyte chemoattractant protein-1 functions as a neuromodulator in dorsal rootganglianeurons. J Neurochem, 2008;104(1):254-263.
Katakura T, et al. CCL17 and IL-10 as effectors that enable alternatively activated macrophages to inhibit the generation of classically activated macrophages. Journal of Immunology, 2004;172:1407-1413.
Keilhoff G, et al. Inhibiting effect of minocycline on the regeneration of peripheral nerves. Dev Neurobiol, 2007;67(10:1382-1395.
Khalil IA, et al. Uptake pathways and subsequent intracellular trafficking in nonviral gene delivery. Pharmacol Rev, 2006;58(1):32-45.
Kim SY, et al. Activation of p38 MAP kinase in the rat dorsal root ganglia and spinal cord following peripheral inflammation and nerve injury. Neuroreport, 2002;13(18):2483-2486.
Kohane DS, et al. Biodegradable polymeric microspheres and nanospheres for drug delivery in the peritoneum. J Biomed Mater Res, 2006;77A92):351-361.
Kojima A, Tator CH. Epidermal growth factor and fibroblast growth factor 2 cause proliferation of ependymal precursor cells in the adult rat spinal cord in vivo. Journal Neuropathology and Experimental Neurology, 2000;59(8):687-697.

(56) References Cited

OTHER PUBLICATIONS

Kolka JA, Vreede AP, Roessler BJ. Lipopolysaccharide recognition protein, MD-2, facilitates cellular uptake of E. coli-derived plasmid DNA in sunovium. J Gene Med, 2005;7(7):956-964.
Kolla VK, et al. Association of tumor necrosis factor alpha, interferon gamma and interleukin 10 gene polymorphisms with peripheral neuropathy in South Indian patients with type 2 diabetes. Cytokine, 2009;47(3):173-177.
Komohara Y, et al. Possible involvement of the M2 anti-inflammatory macrophage phenotype in growth of human gliomas. J Pathol, 2008;216(1):15-24.
Kreutzberg GW. Microglia: a sensor for pathological events in the CNS. Trends Neurosci, 1996;19:312-218.
Krieg AM. CpG motifs in bacterial DNA and their immune effects. Annu Ref Immunol, 2002;20:709-760.
Ladeby R, et al. Microglial cell population dynamics in the injured adult central nervous system. Brain Res Rev, 2005;48(2):196-206.
Lai AY, Todd KG. Hypoxia-activated microglial mediators of neuronal survival are differentially regulated by tetracyclines. Glia, 2006;53(8):809-816.
Lan YY, et al. "Alternatively activated" dendritic cells preferentially secrete IL-10, expand Foxp3+CD4+ T cells, and induce long-term organ allograft survival in combination with CTLA4-IG. J Immunol, 2006;177(9):5868-5877.
Latz E, et al. TLR9 signals after translocating from the ER to CpG DNA in the lysosome. Nature Immunology, 2004;5:190-198.
Lautermilch NJ, Spitzer NC. Regulation of calcineurin by growth cone calcium waves controls neurite extension. J Neurosci, 2000;20(1):315-325.
Ledeboer A, et al. Minocycline attenuates mechanical allodynia and proinflammatory cytokine expression in rat models of pain facilitation. Pain, 2005;115:71-83.
Ledeboer A, et al. Regional and temporal expression pattersn of interleukin-10, interleukin-10 receptor and adhesion molecules in the rat spinal cord during chronis relapsing EAE. J Neuroimmunol, 2003;136:94-103.
Ledeboer AM, et al. Intrathecal interleukin-10 gene therapy attenuates paclitaxel-induced mechanical allodynia and proinflammatory cytokine expression in dorsal root ganglia in rats. Brain Behavoir and Immunity, 2007;21(5):686-698.
Lenert P, et al. TLR-9 activation of marginal zone B cells in lupus mice regulates immunity through increased IL-10 production. J Clin Immunol, 2005;25(1):29-40.
Lenz FA. Neurosurgical treatment of pain. Handbook of Clinical Neurology; Pain, 2006;869-885.
Lingnau M, et al. Interleukin-10 enhances the CD14-dependent phagocytosis of bacteria and apoptotic cells by human monocytes. Hum Immunol, 2007;68(9):730-738.
Liu J, et al. Electrostatically mediated liposome fusion and lipid exchange with a nanoparticle supported bilayer for control of surface charge, drug containment and delivery. J Am Chem Soc, 2009;131(22):7567-7569.
Lunsford L, et al. Tissue distribution and persistence in mice of plasmid DNA encapsulated in a PLGA based microsphere delivery vehicle. J Drug Target, 2000;8(1):39-50.
Madsen M, et al. Molecular characterization of the haptoglobin. hemoglobin receptor CD163. Ligand binding properties of the scavenger receptor cystein-rich domain region. J Biol Chem, 2004;279(49):51561-51567.
Maheshwari A, et al. Biodegradable polymer-based interleukin-12 gene delivery: role of induced cytokines, tumor infiltrating cells and nitric oxide in anti-tumor activity. Gene Therapy, 2002;9:1075-1084.
Mantovani A, et al. Macrophage polarization: tumor-associated macrophages as a paradigm for polarized M2 mononuclear phagocytes. Trends Immunol, 2002;23(11):549-555.
Martinez FO, Helming L, Gordon S. Alternative activation of macrophages: an immunologic functional perspective. Annu Ref Immunol, 2009;27:451-483.
Mata M, Hao S, Fink DJ. Gene therapy directed at the neuroimmune component of chronic pain with particular attention to the role of TNF alpha. Neurosci Lett, 2008;437(3):209-213.
McMahon SB, Cafferty WBJ, Marchand F. Immune and glial cell factors as pain mediators and modulators. Experimental Neurology, 2005;192:444-462.
McMahon SB, Malcangio M. Current challenges in glia-pain biology. Cell, 2009;64.
McMenamin PG, et al. Macrophages and dendritic cells in the rat meninges and choroids plexus:three-dimensional localization by environmental scanning electron microscopy and confocal microscopy. Cell Tissue Res, 2003;313:259-269.
Medzhitov R, Janewar CA Jr. Decoding the Patterns of self and nonself by the innate immune system. Science, 2002;296(5566):298-300.
Milligan ED, et al. Controlling pathological pain by adenovirally driven spinal production of the anti-inflammatory cytokine, Interleukin-10. European Journal Neuroscience, 2005;21:2136-2148.
Milligan ED, et al. Thermal hyperalgesia and mechanical allodynia produced by intrathecal administration of the Human Immunodeficiency Virus-1 (HIV-1) envelope glycoprotein, gp120. Brain Res, 2000;861:105-116.
Milligan ED, et al. Systemic administration of CN1-1493, a p38 mitogen-activated protein kinase inhibitor, blocks intrathecal huan immunodeficiency virus-1 gp120-induced enhanced pain states in rats. J Pain, 2001;2(6):326-333.
Milligan ED, et al. Intrathecal HIV-1 envelope glycoprotein gp120 enhanced pain states mediated byspinal cord proinflammatory cytokines. J Neurosci, 2001;21:2808-2819.
Milligan ED, et al. Controlling neuropathic pain by adeno-associated virus driven production of the anti-inflammatory cytokine, interleukin-10. Molecular Pain, 2005;1:9-22.
Milligan ED, et al. Repeated intrathecal injections of plasmid DNA encoding interleukin-10 produce prolonged reversal of neuropathetic pain. Pain, 2006;126:294-308.
Milligan ED, et al. Intrathecal polymer-based interleukin-10 gene delivery for neuropathic pain. Neuron Glia Biology, 2006;2:293-308.
Milligan ED, et al. Spinal glia and proinflammatory cytokines mediate mirror-image neuropathic pain in rats. J Neuroscience, 2003;23:1026-1040.
Milligan ED, Watkins LR. Pathological and protective roles of glia in chronic pain. Nat Rev Neurosci, 2009;10(1):23-36.
Millligan ED, et al. Evidence that exogenous and endogenous fractalkine can induce spinal nociceptive facilitation in rats. Eur J Neurosci, 2004;20:2294-2302.
Milligan ED, et al. An initial investigation of spinal mechanisms undlying pain enhancement induced by fractalkine, a neuronally released chemokine. Eur J Neurosci, 2005;22:2775-2782.
Mirzadegan T, et al. Identification of the binding site for a novel class of CCR2b chemokine receptor antagonists: binding to a common chemokine receptor motif within the helical bundle. J Biol Chem, 2000;275(33):25562-25571.
Moore KW, al. Interleukin-10 and the interleukin-10 receptor. Annu Rev Immunol, 2001;19:683-765.
Morin N, et al. Neutrophils invade lumbar dorsal root ganglia after chronic constriction injury of the sciatic nerve. J Neuroimmunol, 2007;184(1-2):164-171.
Muskhelishvili L, et al. Evaluation of cell proliferation in rat tissues with BrdU, PCNA, Ki-67(MIB-5) immunohistochemistry and in situ hybridization for histone mRNA. J Histochem Cytochem, 2003;51(12):1681-688.
Nutile-McMenemy N, Elfenbein A, Deleo JA. Minocycline decreases in vitro microglial motility, B1-integrin, and Kv1.3 channel expression. J Neurochem, 2007;10.1111/j.1471-4150.2007.04889.
Pack DW, et al. Design and development of polymers for gene delivery. Nature Rev Drug Discovery, 2005;4:581-593.
Papadopoulos NG, et al. An improved fluorescence assay for the determination of lymphocyte mediated cytotoxicity using flow cytometry. J Immunol Methods, 1994;177(1-2):101-111.
Planck SR, et al. Characterizing extravascular neutrophil migration in vivo in the iris. Inflammation, 2008;31(2):105-111.

(56) References Cited

OTHER PUBLICATIONS

Ponomarev Ed, et al. CNS-derived interleukin-4 is essential for the regulation of autoimmune inflammation and induces a state of alternative activation in microglial cells, J Neurosci, 2007;27(40):10714-10721.
Porcheray F, et al. Macrophage activation switching: an asset for the resolution of inflammation. Clin Exp Immunol, 2005;142(3):481-489.
Ribes S, et al. Toll-like receptor prestimulation increases phagocytosis of *Escherichia coli* DH5 alpha an *Escherichia coli* K1 strains by murine microglial cells. Infect Immun, 2009;77(1):557-564.
Rossi D, Zlotnik A. The biology of chemokines and their receptors. Annu Rev Immunol, 2000;18:217-242.
Sarrias MR, et al. The Scavenger Receptor Cysteine-Rich (SRCR) domain: an ancient and highly conserved protein module of the innate immune system. Crit Rev Immunol, 2004;24(1):1-37.
Schwach G, et al. Biodegradable microparticles for sustained release of a new GnRH antagonist-partI: Screening commercial PLGA and formulation technologies. Eur J Pharm Biopharm, 2003;56(3):327-336.
Sendil D, et al. Antinociceptive effects of hydromorphone, bupivacaine and biphalin released from PLGA polymer after intrathecal implantation in rats. Biomaterials, 2003;24:1969-1976.
Shoskes DA, et al. Cytokine polymorphisms in men with chronic prostatitis/chronic pelvic pain syndrome: association with diagnosis and treatment response. J Urol, 2002;168(1):331-335.
Sloane E, et al. Anti-inflammatory cytokine gene therapy decreases sensory and motor dysfunction inexperimental Multiple Sclerosis: MOG-EAE behavioral and anatomical symptom treatment with cytokine gene therapy. Brain Behav Immun, 2009;23(1):92-100.
Sloane EM, et al. Long term control of neuropathic pain in a non-viral gene therapy paradigm. Gene Therapy, 2009;16(4):470-475.
Soderquist RG, et al. Release of plasmid DNA encoding IL-10 from PLGA microparticles facilitates long-term reversal of neuropathic pain following a single intrathecal administration. J Controlled Release, 2009.
Spittler A, et al. Immunomodulatory effects of glycine on LPS-treated monocytes: reduced TNF-alpha production and accelerated IL-10 expression. FASEB J, 1999;13(3):563-571.
Spittler A, et al. IL-10 augments CD23 expression on U937 cells and down-regulates IL-4-driven CD23 expression on cultured human blood monocytes: effects of IL-10 and other cytokines on cell phenotype and phagocytosis. Immunology, 1995;85(2):311-317.
Stevens SL, et al. Toll-like receptor 9: a new target of ischemic preconditioning in the brain. J Cereb Blood Flow Metab, 2008;28(5):1040-1047.
Sulahian TH, et al. Human monocytes express CD163, which is upregulated by IL-10 and identical to p155. Cytokine, 2000;12(9):1312-1321.
Sweitzer SM, et al. Focal peripheral nerve injury induced leukocyte trafficking into the central nervous system: potential relationship to neuropathic pain. Pain, 2002;100:163-170.
Tikka TM, Koistinaho JE. Minocycline provides neuroprotection against N-methyl-D-apartate neurotoxicity by inhibiting microglia. J Immunology, 2001;166:7526-7533.
Tsai EC, et al. A novel method for simultaneous anterograde and retrograde labeling of spinal cord motor tracts in the same animal. J Histochemistry & Cytochemistry, 2001;49(9):1111-1121.
Uceyler N, et al. Reduced levels of anti-inflammatory cytokines in patients with chronic widespread pain. Arthritis and Rheumatism, 2006;54:2656-2664.
Vandenabeele F, Creemers J, Lambrichts I. Ultrastructure of the human spinal arachnoid mater and dura mater. J Anat, 1996;189(2):417-430.
Vollmer J, et al. Impact of modifications of heterocyclic bases in CpG dinucleotides on their immune modulatory activity. J Leukoc Biol, 2004;76(3):585-593.
Wagner H. The immunobiology of the TLR9 subfamily. Trends Immunol, 2004;25(7):381-386.
Wang D, et al. Oligodeoxyribonucleotide-based antagonists for Toll-like receptors 7 and 9. J Med Chem, 2009;52(2):551-558.
Wang Y, et al. The Toll-like receptor 7 (TLR7) agonist, imiquimod, and the TLR9 agonist, CpG ODN, induce antiviral cytokines and chemokines but do not prevent vaginal transmission of simian immunodeficiency virus when applied intravaginally to rhesus macaques. J Virol, 2005;79(22):14355-14370.
Watkins LR, Maier SF. Glia: A novel drug discovery target for clinical pain. Nat Rev Drug Disc 2003;2:973-985.
Watkins LR, Milligan ED, Maier SF. Spinal cord glia: new players in pain. Pain, 2001;93:201-205.
Watson JD. Molecular Biology of the Gene, 1997;4th Ed, Menlo Park, CA.
White FA, Bhangoo SK, Miller RD. Chemokines: Integrators of pain and inflammation. Nature Rev, 2005;4:834-844.
White FA, Jung H, Miller RJ. Chemokines and the pathophysiology of neuropathic pain. Proc Natl Acad Sci U S A, 2007;104(51):20151-20158.
White FA, et al. Excitatory monocyte chemoattractant protein-I signaling is up-regulated in sensory neurons after chronic compression of the dorsal root ganglion. Proc Natl Acad Sci U S A, 2005;102(39):14092-14097.
et al. Bacterial Lipopolysaccharide copurifies with plasmid DNA: implications for animal models and human gene therapy. Human Gene Therapy, 1995;6:317-323.
Willis WDJ. Hyperalgesia and Allodynia. Hyperalgesia and Allodynia, 1992; New York: Raven Press, Table of contents only.
Yew NS, Cheng SH. Reducing the immunostimulatory activity of CpG-containing plasmid DNA vectors for non-viral gene therapy. Expert Opin Drug Deliv, 2004;1(1):115-125.
Yi AK, et al. Role of mitogen-activated protein kinases in CpG DNA-mediated IL-10 and IL-12 production: Central role of extracellular signal-regulated kinase in the negative feedback loop of the CpG DNA-mediated Th1 response. J Immunol, 2002;168:4711-4720.
Zhang J, et al. Expression of CCR2 in both resident and bone marrow-derived microglia plays a critical role in neuropathic pain. J Neurosci, 2007;27(45):12396-12406.
Zhang RX, et al. Spinal glial activation in a new rat model of bone cancer pain produced by prostate cancer cell inoculation of the tibia. Pain, 2005;118:125-136.
Zhao H, et al. Contribution of Toll-like receptor9 signaling to the acute inflammatory response to nonviral vectors. Mol Ther, 2004;9(2):241-248.
Carroll, et al. Microparticles with Bimodal Nanoporosity Derived by Microemulsion Templating. Langmuir, 2009;25:13540-13544.
Liu, et al. Silica nanoparticle supported lipid bilayers for gene delivery. Chem Comm, 2009;5100-5102.
Liu, et al. Porous Nanoparticle Supported Lipid Bilayers (Protocells) as Delivery Vehicles. J Amer Chem Soc, 2009;131:1354-1355.
Lu, et al. Aerosol-assisted self-assembly of mesostructured spherical nanoparticles. Nature, 1999;398:223-226.
Ashley, et al. The targeted delivery of multicomponent cargos to cancer cells by nanoporous particle-supported lipid bilayers. Nature Materials, 2011;10(5):389-397.
Dengler, et al. Mesoporous silica-supported lipid bilayers (protocells) for DNA cargo delivery to the spinal cord. Journal of Controlled Release, 2013;168:209-224.
NIST. Particle Size Characterization, Special Publication 960-1, 2001.
Takeuchi, et al. An Axissymmetric Flow-Focusing Microfluidic Device. Advanced Materials, 2005;17(8):1067-1072.

\* cited by examiner

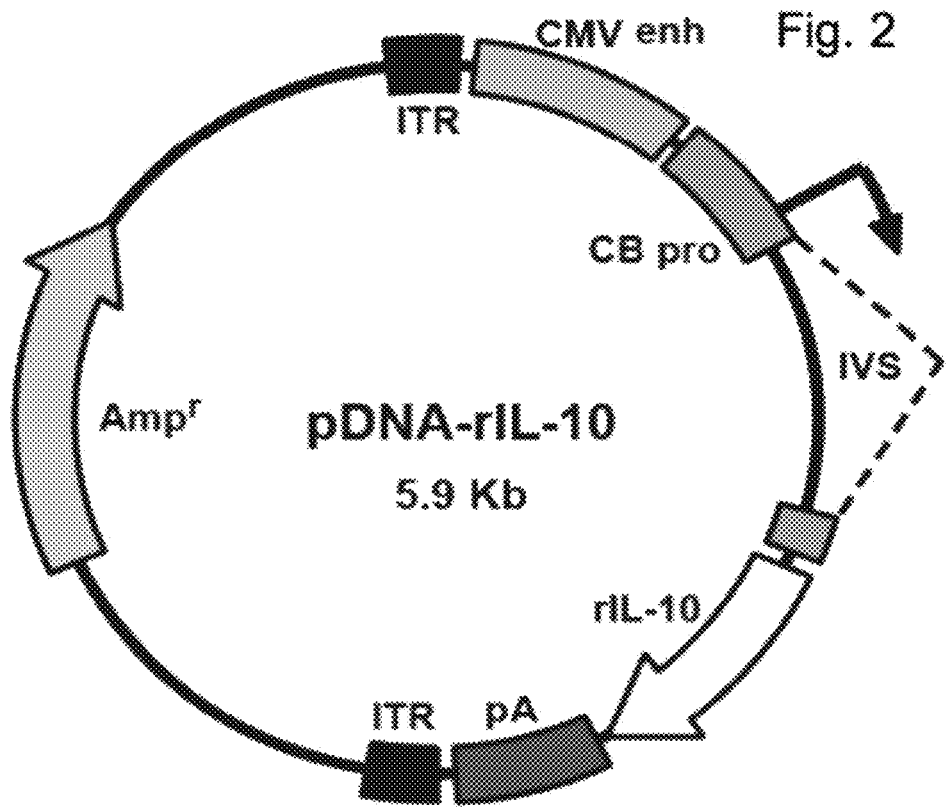
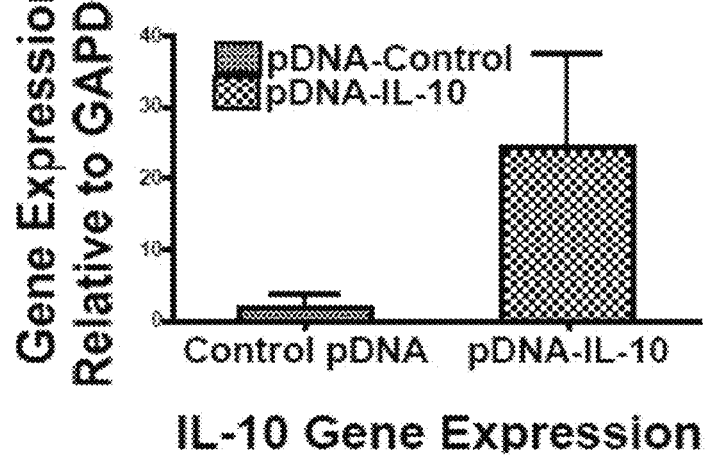

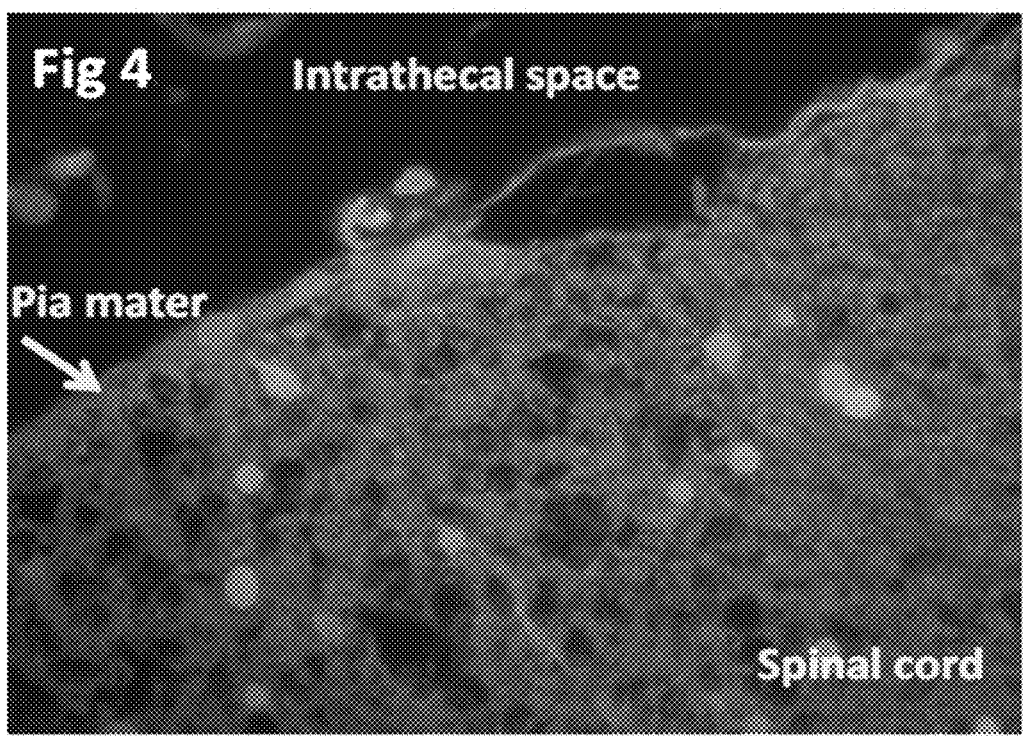
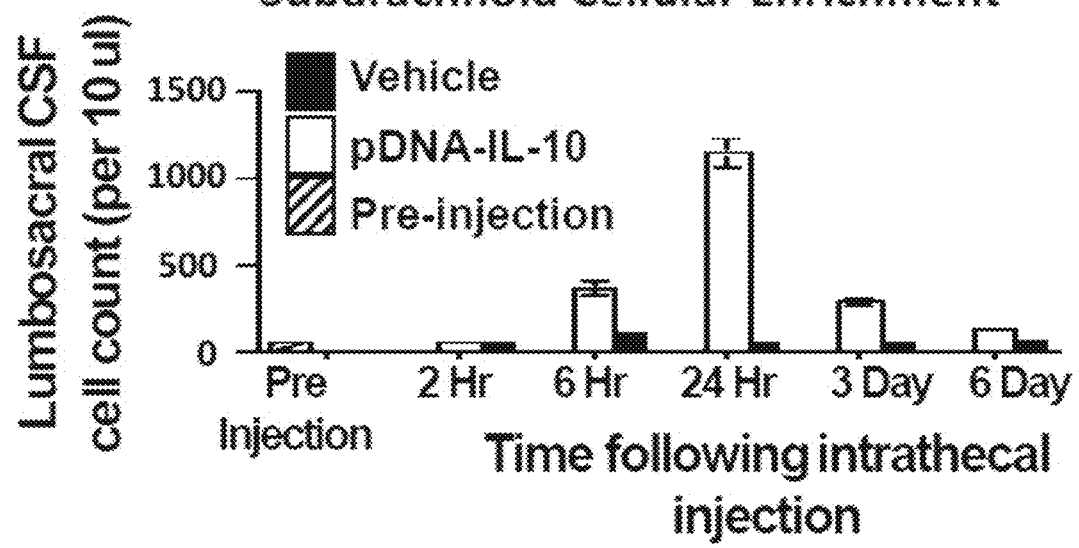

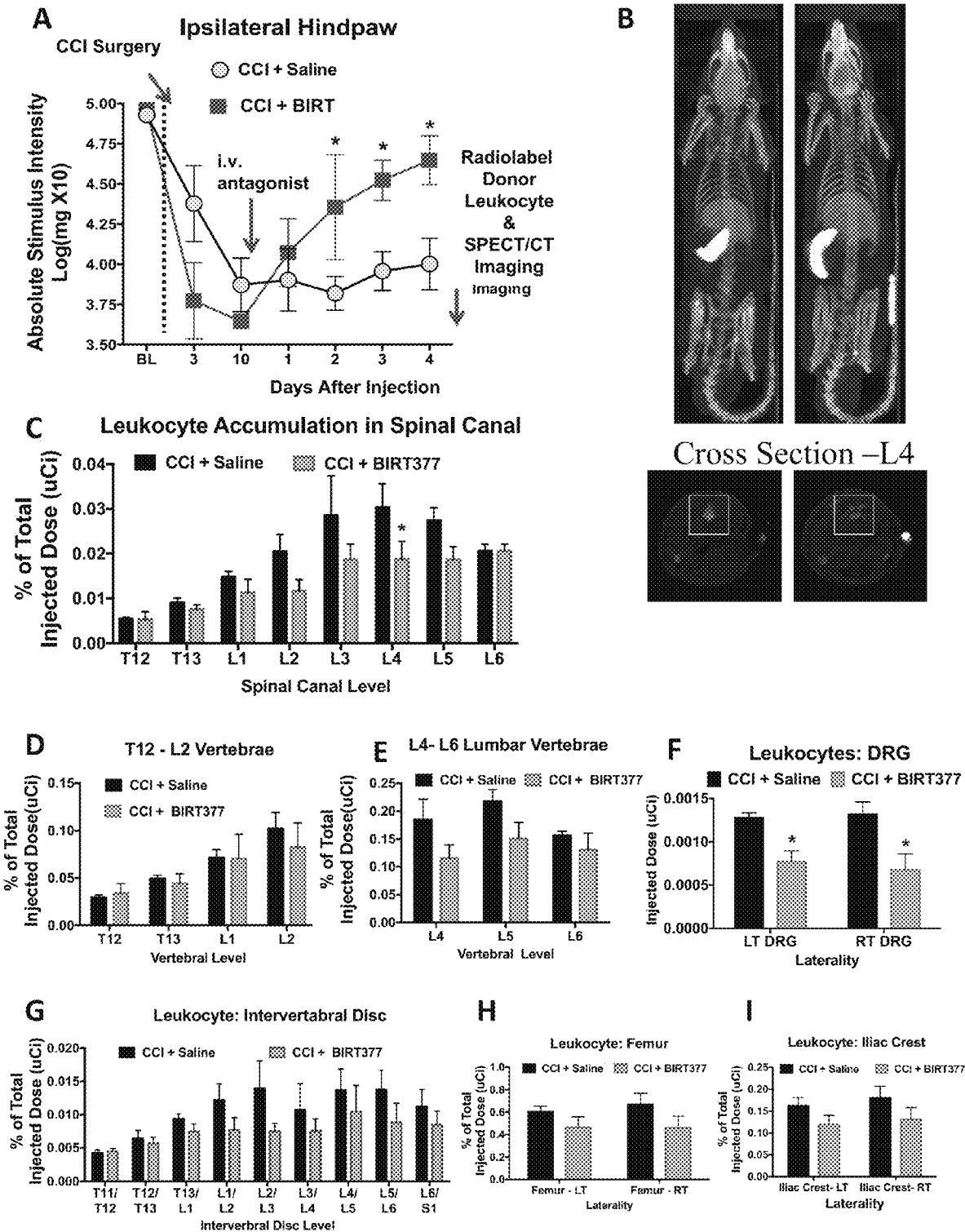

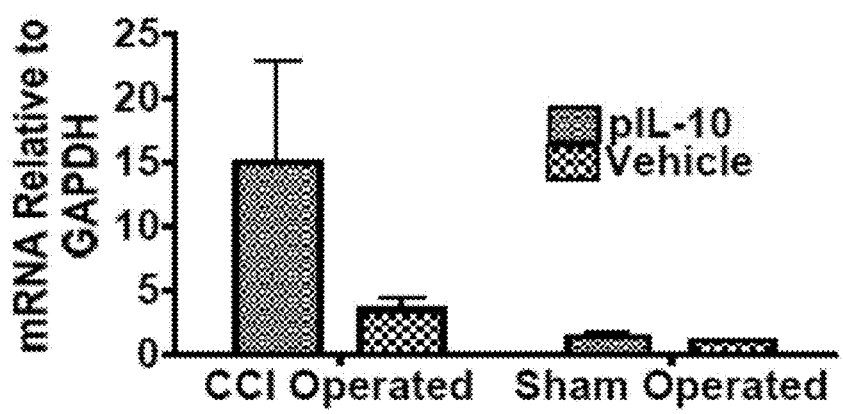
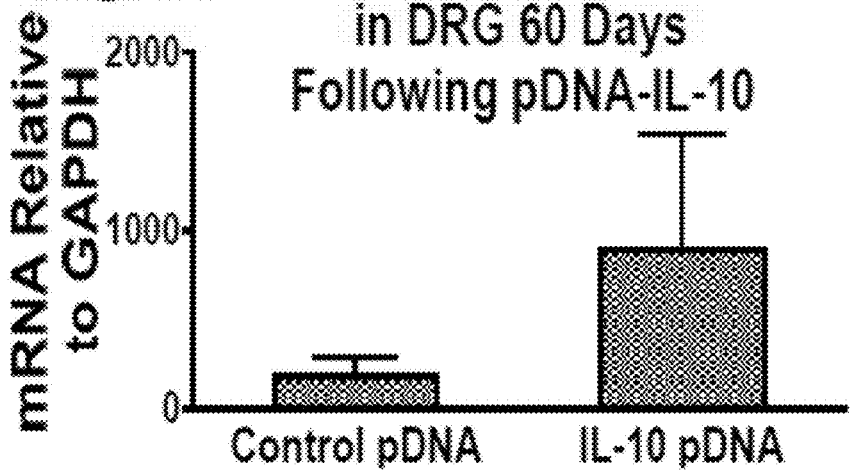

PLGA
Spherical & Smooth

Median Diameter
4.67 ± 0.81 µm

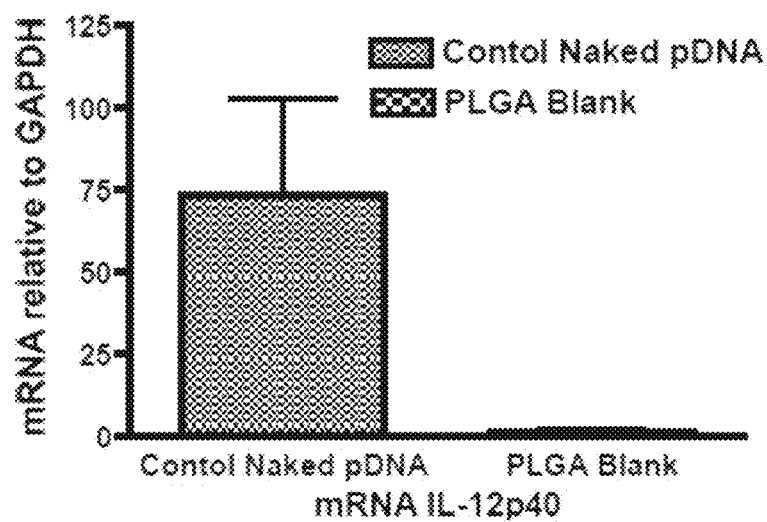
Fig 11
IL-12p40 mRNA Levels are Not Altered After PLGA Treatment
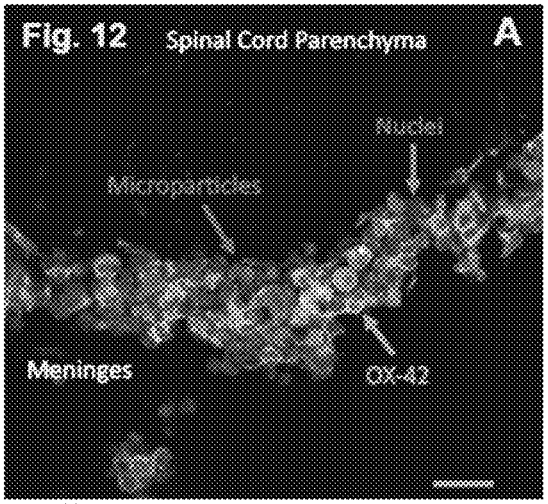
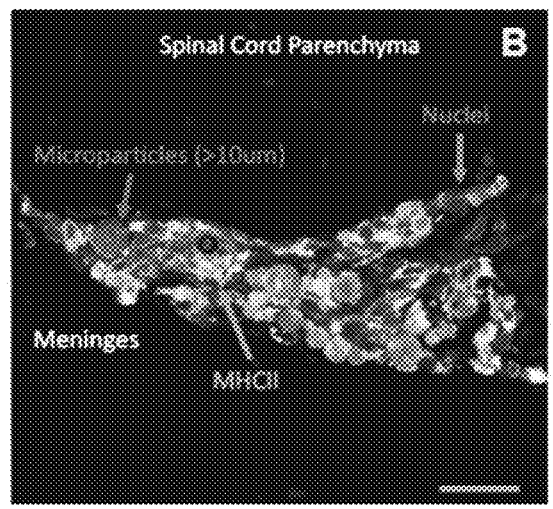

Choice of Transgene Expression Constructs.

NorBIRT inhibits LPS-induced NO production in RAW 264.7 macrophage cells

NorBIRT-attenuates expression of the pro-inflammatory cytokine TNF-α in LPS simulated RAW 264.7 cells NorBIRT inhibits LPS-stimulated expression of IL-1β in RAW 264.7 cells NorBIRT increases the IL-10 production in LPS-stimulated macrophage RAW 264.7 cells NorBIRT does not inhibit LPS-stimulated CCL2 production in RAW 264.7 cells NorBIRT inhibits LPS-stimulated LFA-1 protein expression in RAW 264.7 cells NorBIRT inhibits mouse macrophage cell migration NorBIRT does not affect the viability of RAW 264.7 cells

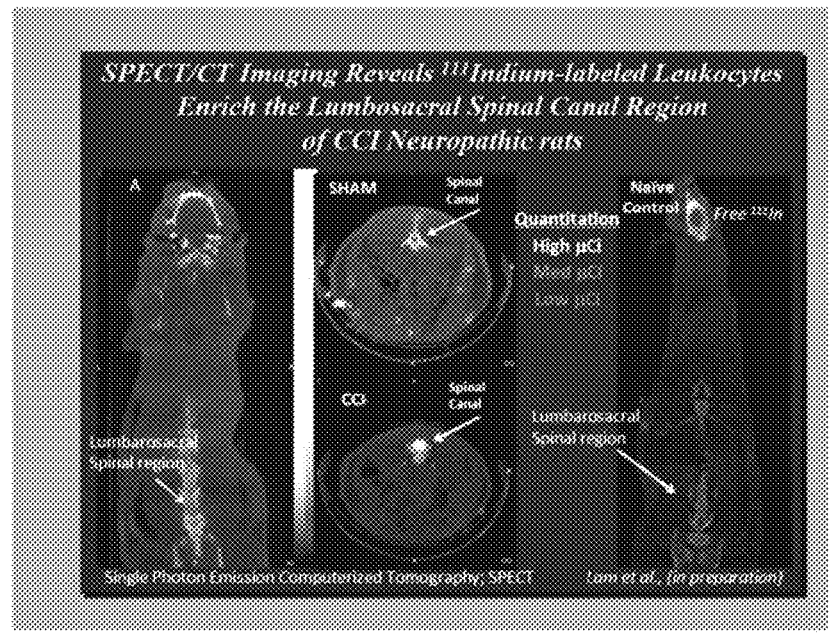
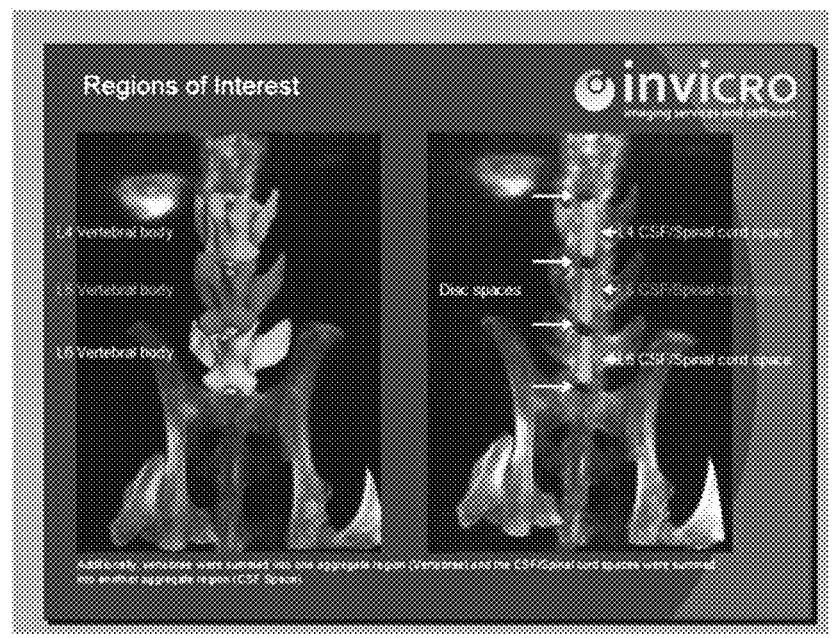
FIGURE 28

FIGURE 39
A
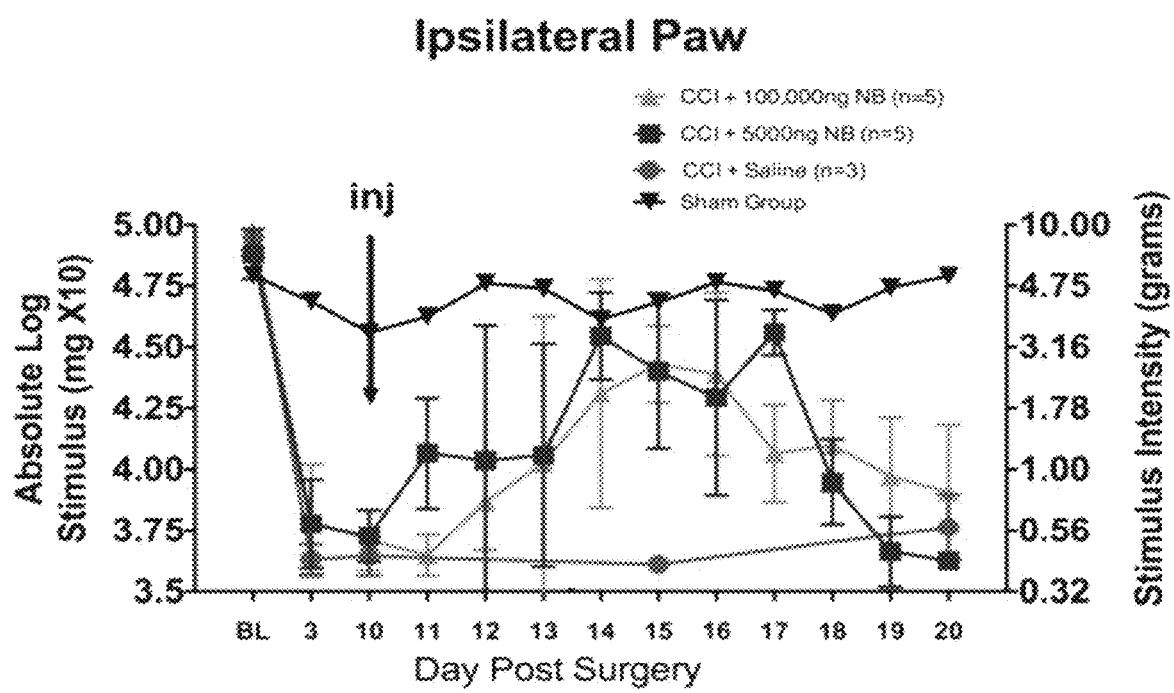
Ipsilateral Paw
B
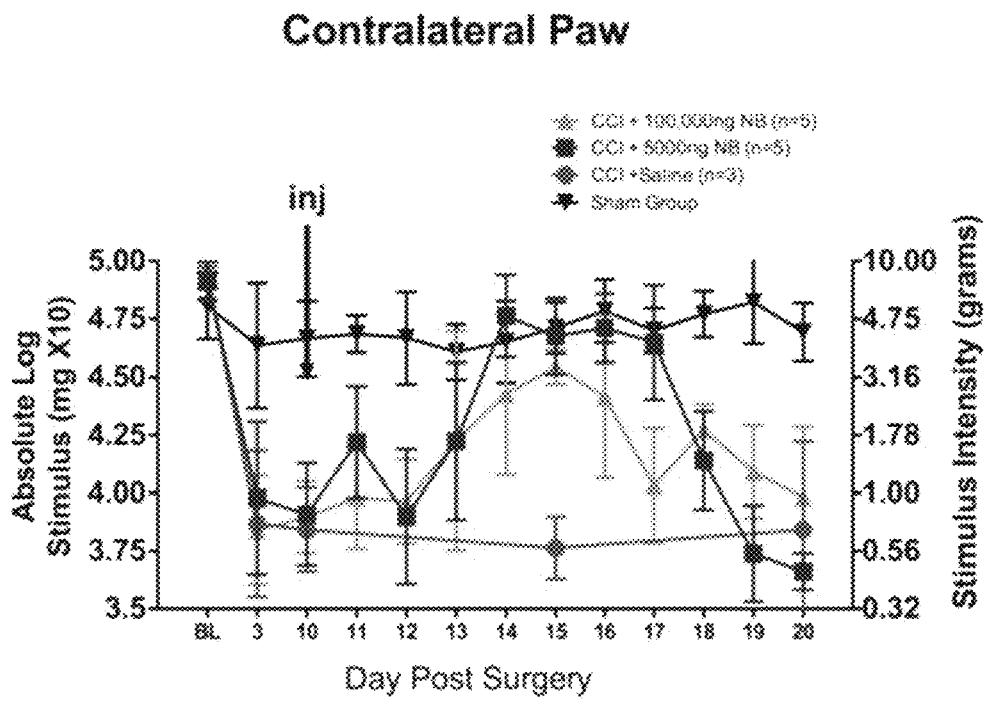
Contralateral Paw

FIGURE 40
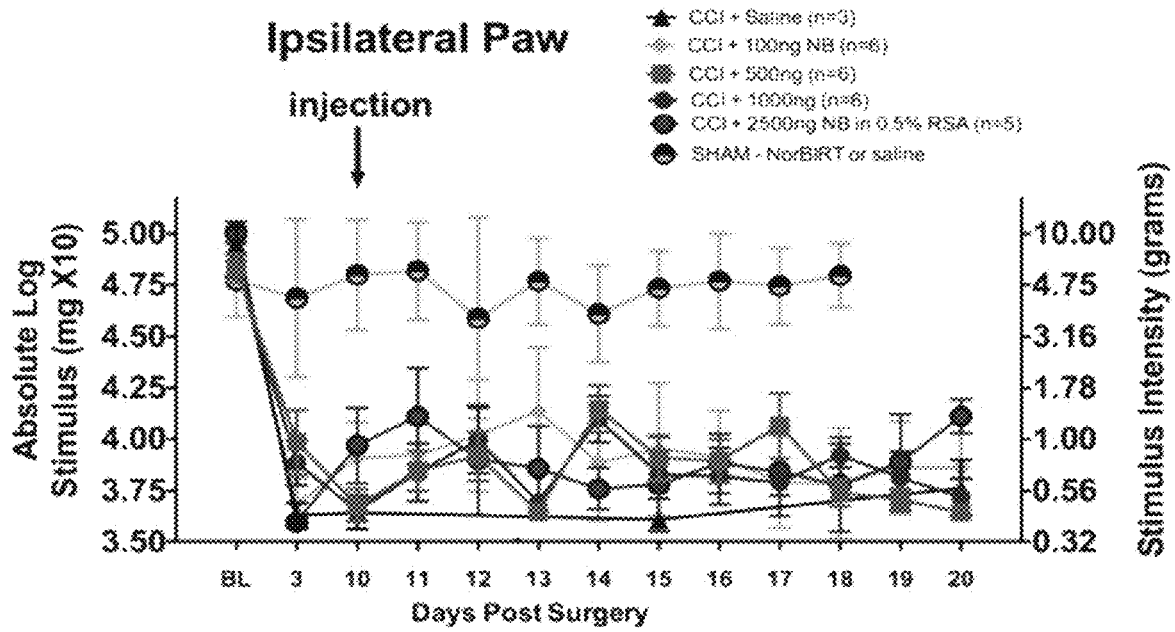
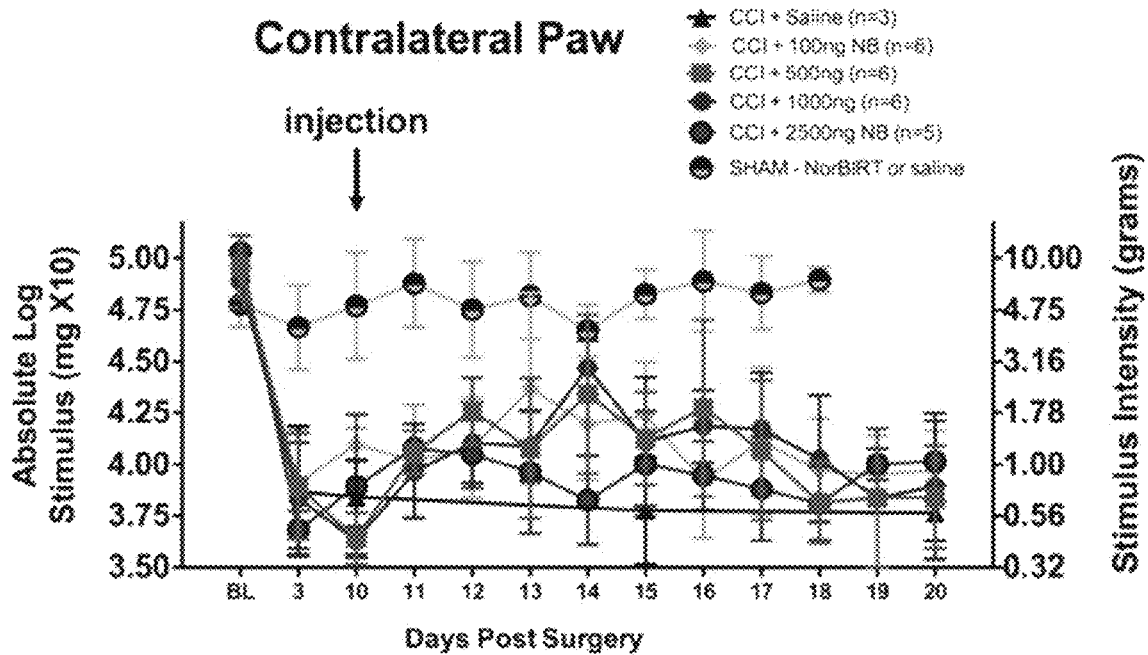

CONTROL OF CHRONIC NEUROPATHIC PAIN AND ALLODYNIA

CROSS REFERENCE TO RELATED APPLICATIONS

This application claims priority from: (1) U.S. Provisional Patent Application No. 61/775,789, filed Mar. 11, 2013 and entitled "Therapies to Control Chronic Neuropathic Pain" (2) U.S. Provisional Patent Application No. 61/875,264, filed Sep. 9, 2013 and entitled "Therapies to Control Chronic Neuropathic Pain"; and (3) U.S. Provisional Patent Application No. 61/901,864, filed Nov. 8, 2013 and entitled "Therapies to Control Chronic Neuropathic Pain". The complete contents of each of the aforementioned three provisional applications are hereby incorporated herein in their entirety.

STATEMENT REGARDING FEDERAL FUNDING

This invention was made with government support under National Institute of Health Grant Nos. R01 DA018156. Consequently, the United States has certain rights in the invention.

FIELD OF THE INVENTION

In one embodiment, the invention provides a method of treating a subject suffering from chronic neuropathic pain and/or allodynia by administering a therapeutically-effective amount of at least one LFA1 antagonist to the subject alone or in combination with at least one additional therapeutic agent which is useful for the treatment of acute or chronic neuropathic pain.

In another embodiment, the invention provides a method of treating a subject suffering from chronic neuropathic pain and/or allodynia by co-administering to the subject a therapeutically-effective amount of: (a) at least one LFA1 antagonist, and (b) at least one additional therapeutic agent selected from the group consisting of (1) a non-viral plasmid DNA vector which expresses an interleukin selected from the group consisting of IL-10, IL-2, IL-4 and TGF-β (2) an IL-1 receptor antagonist, and (3) alpha-melanocyte stimulating hormone (alpha-MSH).

In another embodiment, the invention provides a method of treating a subject suffering from chronic neuropathic pain and/or allodynia, the method comprising administering intrathecally to the subject a therapeutically-effective amount of microparticles comprising a non-viral plasmid DNA vector which (1) expresses an interleukin selected from the group consisting of IL-10, IL-2, IL-4, IL-13, tumor necrosis factor soluble receptor (TNFsr) and TGF-β, and (2) is encapsulated within a biodegradable polymer selected from the group consisting of caprolactone, polylactic acid (PLA), polylactic-co-glycolic acid (PLGA) or polylactic-co-hydroxymethylglycolic acid (PLHMGA). The present invention contemplates coadministering these agents in combination with LFA-1 antagonists described hereunder.

In a preferred embodiment, the invention provides a method of treating a subject suffering from chronic neuropathic pain and/or allodynia, the method comprising administering intrathecally to the subject a therapeutically-effective amount of microparticles comprising PLGA-encapsulated pDNA-IL-10, optionally in combination with a therapeutically-effective amount of intrathecally-administered CpG oligodeoxynucleotide (CpG ODN).

Related pharmaceutical formulations (including microparticle and protocell formulations) are also provided.

BACKGROUND OF THE INVENTION

Neuropathic pain is often associated with peripheral nerve injury, (e.g. sciatic nerve) caused by compression, transection, and/or inflammation (FIG. 1) [34]. When injured or inflamed tissue persists chronically, this leads to ongoing excitation in primary sensory pain neurons located in the dorsal root ganglia (DRG) that communicate to pain transmission neurons in the dorsal horn of the spinal cord. Injured or inflamed tissue in the central nervous system can alter and excessively activate spinal pain transmission neurons in the pain pathway. If these events continue, chronic pain ensues. Pathological pain occurs when abnormal sensory processing occurs in the pain pathway such that non-painful light mechanical touch can become encoded as painful (allodynia). Chronic neuropathic pain (>3 months) is thus no longer the adaptive, protective mechanism that normal pain serves for recuperation and wound healing [19].

Glial (astrocytes, microglia, satellite & Schwann) cells are recognized as contributing to the development and maintenance of neuropathic pain [86]. Glia are well-known to serve a number of housekeeping functions for healthy neuronal communication. However, a number of animal models, including peripheral nerve inflammation and trauma, demonstrate spinal cord glial (astrocytes & microglia) activation is a common underlying mechanism that leads to pathological pain [97]. Glia have receptors for and are activated by invading pathogens, neuropeptides and neurotransmitters [97]. Once activated, glia can contribute to persistent pathological pain by responding to and releasing factors that act on both neurons and surrounding glia. Classic immune signals include the pro-inflammatory cytokines, interleukin-1 (IL-1β) and tumor necrosis factor-alpha (TNF-α), and chemokines such as CCL2 [139, 142]. Chronic constriction injury (CCI) is a well-characterized animal model that involves both inflammation and trauma around one sciatic nerve. Loose sciatic nerve ligation of 4 sutures produces allodynia in hind paws of rodents. Allodynia in rodents is often measured by hind paw responses to low threshold mechanical stimuli (von Frey test). Clinically, allodynia is well-documented as a common problem for neuropathic pain patients [145], and the von Frey test is a highly validated assessment tool for allodynia [17]. Several gene therapy vector approaches for neuropathic pain control are being pursued for directed delivery to the dorsal spinal cord & DRG (the pain compartments) & to specific cell types within those compartments, such as glial cells in the DRG (satellite & Schwann cells) or astrocytes and microglia in the dorsal horn of the spinal cord, with one recent clinical trial underway [84].

No report currently exits that directly links decreased IL-10 gene expression and neuropathic pain in humans. However, several reports have documented that gene polymorphisms of the anti-inflammatory cytokine, IL-10 that lead to decreased IL-10 expression are associated with the incidence of pain in inflammatory bowel disorders, neuropathic pain, and chronic pelvic pain [29, 61, 118]. In addition, several clinical studies document increased circulating IL-1β and TNF-α levels with concurrent decreased circulating IL-10 [132]. Further, pro-inflammatory cytokine polymorphisms have been correlated in chronic pelvic pain syndromes [118], and in patients with neuro-Behcet's disease; an inflammatory disorder with unknown etiology that produces painful immune-mediated meningioencephalitis [37].

Importantly, the potential application of IL10 is not necessarily intended to correct IL-10 function per se. Rather, IL-10 is promising for pathological pain treatment because it exerts powerful anti-inflammatory actions. In numerous animal models, pain mediated by proinflammatory cytokine actions on pain processing neurons is controlled by spinal IL-10 [97, 114]. Because TNF-α and IL-1 are so powerful, immune and glial cells have evolved the means to create negative feedback suppression of their activity. This is achieved via mechanisms that include the production of IL-10 [102]. While spinal cord neurons do not express receptors for nor make IL-10 [73], IL-10 terminates proinflammatory processes by inhibiting a variety of cytokines including TNF-α and IL-1β at multiple levels. IL-10 prevents p38 MAP kinase activation, NFkB activation, translocation & DNA binding; preventing TNF-α and IL-1β transcription, translation & post-translational processing; destabilizing TNF-α and IL-1β mRNA to decrease its half-life; desensitizing responses to TNF-α and IL-1β by increasing IL-1 receptor antagonist & TNF decoy receptors. A comprehensive suppression of TNF-α and IL-1β production and signaling can be achieved through the actions of IL-10. IL-10 is both a natural product of glia (astrocytes & microglia) and innate immune cells like macrophage and dendritic cells & binds to receptors expressed by them ([102] for review).

Prior work on the LFA-1 antagonist molecule, BIRT-377 and its derivatives, NorBIRT and DANBIRT, demonstrated that these small molecules exert antiproliferative and antimigratory properties of leukocytes. Yet, whether BIRT-377, NorBIRT and DANBIRT act to directly inhibit IL-1β, TNF-α, CCL2 and NO actions in the spinal cord leading to suppression of pathological pain was heretofore unknown.

Better understanding of the aforementioned processes will help address the persistent problem of chronic neuropathic pain in the patient population.

SUMMARY OF THE INVENTION

We characterized the direct action of NorBIRT to suppress elevated IL-1β, TNF-α, CCL2 and NO in macrophage cell cultures stimulated with lipopolysaccharide. Our data show that NorBIRT also suppresses classic proinflammatory cytokine levels while also elevating the anti-inflammatory cytokine, interleukin-10 (IL-10). Therefore, NorBIRT is an entirely novel pain therapeutic because it reduces proinflammatory cytokine levels while elevating anti-inflammatory cytokine IL-10. During the course of discovering NorBIRT's mechanism of anti-IL-1β, TNF-α cytokine action, we also determined that leukocytes accumulate in lumbar spinal canal regions in an animal model of sciatic neuropathy that leads to ongoing allodynia. NorBIRT/DANBIRT and their derivatives act not only to suppress leukocyte migration into the lumbosacral spinal region where critical pain processing occurs, but also, act to suppress allodynia by controlling elevated proinflammatory factors while enhancing the anti-inflammatory cytokine, IL-10.

Thus, in one embodiment, the invention provides a method of treating a subject suffering from chronic neuropathic pain and/or allodynia by administering a therapeutically-effective amount of at least one LFA1 antagonist to the subject. In one embodiment, the LFA1 antagonist is selected from the group consisting of:

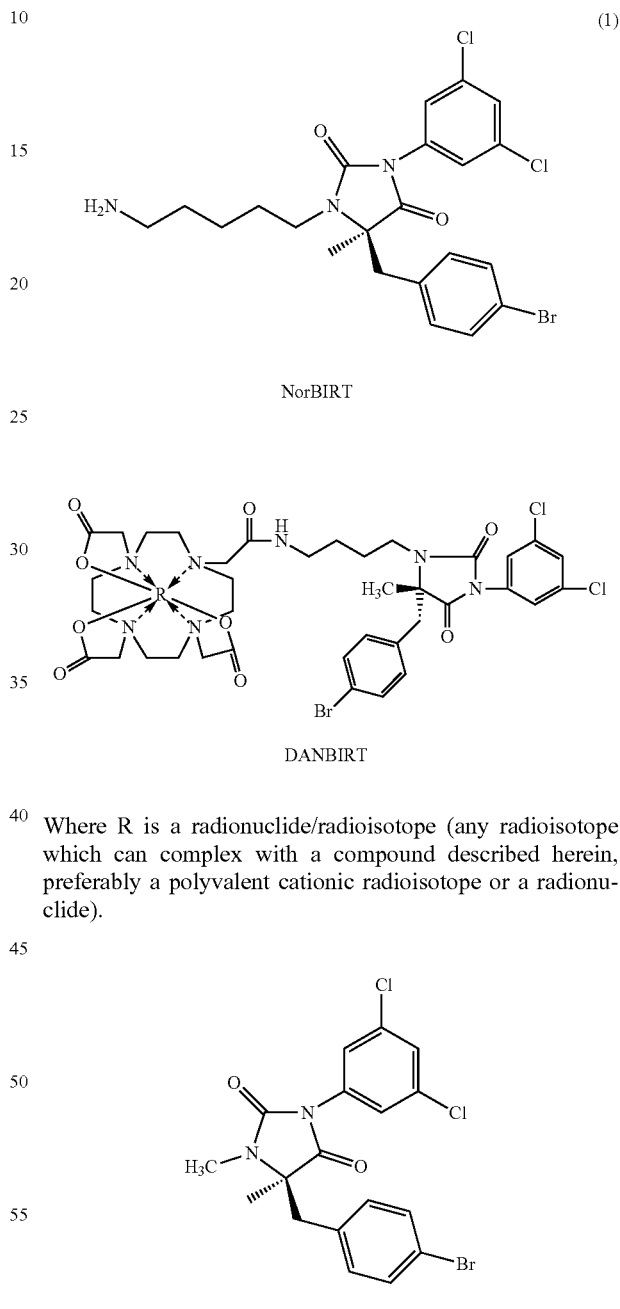

Where R is a radionuclide/radioisotope (any radioisotope which can complex with a compound described herein, preferably a polyvalent cationic radioisotope or a radionuclide).

(2) a pharmaceutically acceptable salt, enantiomer, stereoisomer, solvate or polymorph of NorBIRT, DANBIRT and BIRT-377 or derivative or analogue of NorBIRT, DANBIRT and BIRT-377 disclosed in US20110117014, WO2009151646 and U.S. Pat. No. 6,881,747, each of which is incorporated by reference in its entirety herein;

(3) a compound having the formula I:

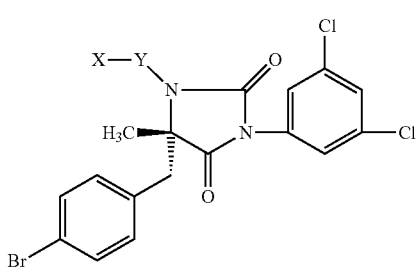

and a pharmaceutically acceptable salt, enantiomer, stereoisomer, solvate or polymorph thereof, wherein:

(a) Y is a hydrocarbyl which is optionally a chemical linker linking the nitrogen to group X, and X is an active group selected from the group consisting of a reporter (fluorescent group), a toxin, a radiolabel (radionuclide) and a chelating group which complexes with a radioisotope or a drug; or (b) Y is a linker comprising a $C_1$-$C_{10}$ hydrocarbyl group containing two amino groups or two sulfur groups which are linked with a chelating moiety X which incorporates or complexes to a radioisotope; and In alternative embodiments of formula I:

(a) Y is a hydrocarbyl which is optionally a chemical linker linking the nitrogen to group X wherein X is an active group, such as a reporter (fluorescent group), a cytotoxic agent such as a toxin, a radiolabel (radionuclide), a moiety such as a chelating group which complexes with a radioisotope or a drug. In preferred aspects of the invention, Y is an optionally substituted $C_1$-$C_{10}$ hydrocarbyl (including an optionally substituted aryl group), preferably an optionally substituted alkyl group, for example a —$(CH_2)_n$Z— group, where n is from 1 to 6 and Z is O, NR or N—$CH_2CH_2$—O, where R is H or a $C_1$-$C_3$ alkyl (preferably H) or Z is a keto (C=O) group, a $S(O)_n$ group where w is from 0 to 4 (i.e., a sulfide, sulfoxide, sulfone, sulfonate or sulfate group), a phosphonate group or a phosphate group and X is a drug, a cytotoxic agent or a chelate group in which a radioisotope is optionally incorporated or complexed. In certain preferred aspects, Y is a —$(CH_2)$—NH— group, where n is from 1 to 6, preferably from 2 to 4, preferably 4 and X is an polyaminocarboxylic macrocycle, including 1,4,7,10-tetraazacyclododecane-1,4,7,10-tetraacetic acid (DOTA) as a chelating agent.

In embodiments of the invention in chemical formula I:

Y is a linker comprising a $C_1$-$C_{10}$, preferably a $C_3$-$C_8$ substituted hydrocarbyl group (which is bonded to the nitrogen of the dioxoimidazolyl group through a keto group) containing two amino groups or two sulfur groups which are linked with a chelating moiety X which incorporates or complexes to the radioisotope. In certain aspects, the preferred linker contains a dithiahexyl group or a diaminohexyl or diaminobutyl group. In another aspect the linker may be derived from lysine (linked to the dioxoimidazolinyl group through the carboxylic acid moiety of lysine). Chemical linkage of the linker to the dioxoimidazolinyl group may be through a carbonyl group, alkylene group or other group capable of being linked to the nitrogen of the dioxoimidazolinyl group; and (4) a compound having the formula:

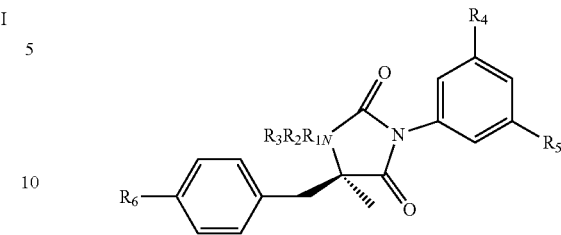

where $R_1$ is an alkyl (alklylene) group having 1 to 12 carbons; $R_2$ is a urea or phosphate group; $R_3$ is an active group, such as a fluorophore such as fluorescein, a toxin, radiolabel (which can include a chelating moiety) or drug; and $R_4$, $R_5$ and $R_6$ are each independently a halide group.

The LFA1 antagonist may be complexed with a chelating moiety, such as a DOTA group or other chelating moiety and/or a radionuclide/radioisotope (any radioisotope which can complex with a compound described herein (preferably a polyvalent cationic radioisotope or a radionuclide preferably selected from the group consisting of $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re and $^{99m}$Tc)).

In certain embodiments of the invention, the compound incorporates or is complexed with a radioisotope as otherwise described herein. In certain aspects of the invention, X (or in some cases $R_3$) includes a chelating moiety such as DOTA (1,4,7,10-tetraazacyclododecane-1,4,7,10-tetraacetic acid), CB-TE2A (4,11-bis(carboxymethyl)-1,4,8,11-tetraazabicyclo [6.6.2]hexadecane), NOTA (1,4,7-triazacyclononane-1,4,7-triacetic acid), DTPA (Diethylenetriaminopentaacetic acid), $MAG_3$ (Mercaptoacetyltriglycine) and 4,5-bis(2-mercaptoacetamido)pentanoic acid. Other chelating moieties that can complex to radioisotopes are otherwise disclosed herein.

In another embodiment, the invention provides a method of treating a subject suffering from chronic neuropathic pain and/or allodynia by co-administering to the subject a therapeutically-effective amount of: (a) at least one LFA1 antagonist (e.g. an LFA1 antagonist described above), and (b) at least one additional neuropathic therapeutic agent (i.e., an agent which can be used for the treatment of neuropathic pain) selected from the group consisting of (1) a non-viral plasmid DNA vector which expresses an interleukin selected from the group consisting of IL-10, IL-2, IL-4 and TGF-β (2) an IL-1 receptor antagonist, and (3) alpha-melanocyte stimulating hormone (alpha-MSH).

Preferably, the LFA1 antagonist and the at least one additional therapeutic agent (e.g. non-viral plasmid DNA vector) are co-administered intrathecally.

In some embodiments, the co-administered LFA1 antagonist, non-viral plasmid DNA vector, IL-1 receptor antagonist and alpha-melanocyte stimulating hormone (alpha-MSH) are optionally combined as active ingredients of microparticulate or nanoparticle (preferably encapsulated with a lipid) formulations described hereinafter. Alternatively, the LFA1 antagonist is co-administered with microparticles or protocells which each comprise a non-viral plasmid DNA vector which expresses an interleukin selected from the group consisting of IL-10 (e.g. PLGA-encapsulated plasmid DNA encoding the IL-10 gene (pDNA-IL-10)), IL-2, IL-4, IL-13, tumor necrosis factor soluble receptor (TNFsr) and TGF-β.

Preferred microparticle formulations are comprised of biodegradable polymers such as poly(lactic-co-glycolic acid)(PLGA)(e.g. as illustrated in Examples 6 and 8).

In another embodiment, the invention provides a method of treating a subject suffering from chronic neuropathic pain and/or allodynia by co-administering to the subject a therapeutically-effective amount of lipid encapsulated nanoparticles comprising:
(a) a porous nanoparticlulate core comprising a non-viral plasmid DNA vector which (1) expresses an interleukin selected from the group consisting of IL-10, IL-2, IL-4, IL-13, tumor necrosis factor soluble receptor (TNFsr) and TGF-β; and
(b) a lipid bilayer which encapsulates the porous nanoparticlulate core. LFA1 antagonists as otherwise described herein are optionally coadministered with these protocells or included in these protocells.

Preferred protocell compositions comprise:
(a) a core comprising a plurality of negatively-charged, nanoporous, nanoparticulate silica cores that are optionally modified with an amine-containing silane and that are interspersed with one or more LFA1 antagonists and, optionally, a non-viral plasmid DNA vector which expresses an interleukin selected from the group consisting of IL-10, IL-2, IL-4 and TGF-β; and
(b) a lipid bilayer which encapsulates the core and which comprises one of more lipids selected from the group consisting of 1,2-dioleoyl-sn-glycero-3-phosphocholine (DOPC), 1,2-dipalmitoyl-sn-glycero-3-phosphocholine (DPPC), dioleylglycero triethyleneglycyl iminodiacetic acid (DOIDA), distearylglycerotriethyleneglycyl iminodiacetic acid (DSIDA), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino]lauroyl]-sn-Glycero-3-Phosphocholine (18:1-12:0 NBD PC), 1-palmitoyl-2-{12-[(7-nitro-2-1,3-benzoxadiazol-4-yl)amino]lauroyl}-sn-glycero-3-phosphocholine (16:0-12:0 NBD PC), cholesterol and mixtures/combinations thereof, wherein the lipid bilayer optionally comprises a cationic lipid and one or more zwitterionic phospholipids and contains on its surface at least one peptide that targets a proinflammatory cytokine. These lipid encapsulated nanoparticles may optionally include at least one LFA1 antagonist as otherwise described herein.

In another embodiment, the invention provides a method of treating a subject suffering from chronic neuropathic pain and/or allodynia, the method comprising administering intrathecally to the subject a non-viral plasmid DNA vector which (1) expresses an interleukin selected from the group consisting of IL-10, IL-2, IL-4, IL-13, tumor necrosis factor soluble receptor (TNFsr) and TGF-β, and (2) is encapsulated within a biodegradable polymer selected from the group consisting of caprolactone, polylactic acid (PLA), polylactic-co-glycolic acid (PLGA) or polylactic-co-hydroxymethylglycolic acid (PLHMGA).

In still another embodiment, the invention provides a method of treating a subject suffering from chronic neuropathic pain and/or allodynia, the method comprising administering intrathecally to the subject a therapeutically-effective amount of microparticles comprising PLGA-encapsulated pDNA-IL-10. In addition to the PLGA-encapsulated pDNA-IL-10, a therapeutically-effective amount of CpG oligodeoxynucleotide (CpG ODN) can be co-administered intrathecally to the subject.

The invention also includes microparticle and protocell pharmaceutical compositions as described above and as disclosed in further detail hereinafter.

These and other aspects of the invention are described further in the Detailed Description of the Invention.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 2: the optimal vector identified for long-duration pain control was determined to be free pDNA encoding the IL-10 gene, as determined in the experiment of Example 1.

FIG. 3: IT pDNA-IL-10 produced substantially greater mRNA IL-10 transgene levels in DRG examined 60 days after IT injection compared to mRNA levels from IT pDNA chronic pain controls, as determined in the experiment of Example 2.

FIG. 4: immune-mediated mechanisms in the lumbar meninges that may be responsible for transgene expression. Macrophage & microglia (stained red) in the pia mater of the meninges, as determined in the experiment of Example 3.

FIG. 5: IT pDNA stimulates local innate immune cell enrichment. Enrichment could be responsible for subsequent IT pDNA-IL10 'uptake' of pDNA-sensitized cells. The time course of cell enrichment measured in CSF from hours to days after IT pDNA-IL-10 injection corresponds to the inter-injection intervals of IT pDNA-IL10 that produces long-duration pain relief, as determined in the experiment of Example 3.

FIG. 9: pDNA-IL-10 induced increased TLR-9 mRNA production in neuropathic rats measured 2 weeks following IT pDNA-IL-10 (FIG. 9A). TLR-9 stimulation in premature macrophage and dendritic cells results in the production of a panel of cytokines and chemokines that direct cell recruitment and differentiation [7, 57]. Indeed, we have now measured increased mRNA levels of the chemokine, CCL2, at day 60 after IT pDNA-IL-10 in behaviorally verified animals. These data support that in animals with enduring pain relief who express robust increases in plasmid-derived IL-10 mRNA at day 60, ongoing CCL2 production occurs simultaneously (FIG. 9B). As determined in the experiment of Example 5.

FIG. 11: IT PLGA does not lead to elevations in the pro-inflammatory cytokine, interleukin-12 (IL-12). As determined in the experiment of Example 6.

FIG. 12: Using confocal microscopy, we identified PLGA rhodamine-labeled (red) microparticles in close association with accumulated innate immune cell nuclei (DAPI; blue) in the meninges. Additionally, microglial cells identified by staining for Cd11b using the classic OX-42 antibody (FITC) interacts with PLGA in the meninges (FIG. 12A). Immune cells were identified using the classic monocyte/macrophage marker, MHC II (FITC; green) (FIG. 12B) two weeks after the second IT pDNA-IL-10 injection. As determined in the experiment of Example 6.

FIG. 19 illustrates 3 PLGA microparticle formulations to be tested that release cargo with: (1) 100% over 72 hr; dashed blue line, and (2) 100% over 1 month; solid blue line, and (3) 45% cargo release within 72 hr with the remainder by 2 months; red line, current formulation. As determined in the experiment of Example 8.

FIG. 28: SPECT/CT Imaging Reveals 111Indium-labeled Leukocytes Enrich the Lumbosacral Spinal Canal Region of CCI Neuropathic rats. As determined in the experiments of Example 10.

Figure 1:
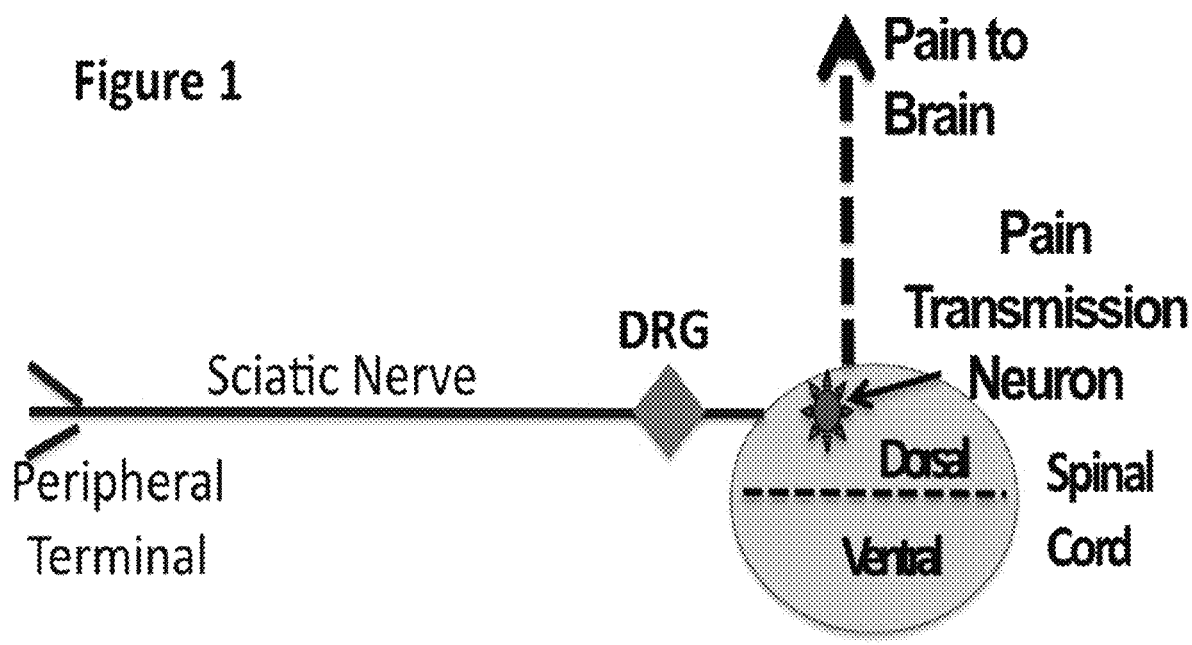
FIG. 1: Neuropathic pain is often associated with peripheral nerve injury, (e.g. sciatic nerve) caused by compression, transection, and/or inflammation, as illustrated in FIG. 1.

FIGS. 39A and B: This figure shows in a first experiment that intravenous injection of NorBIRT also reverses CCI-induced mechanical allodynia in a dose depended manner after 10 days. Figure A shows the effect on the ipsilateral paw and B shows the effect on the contralateral paw.

FIGS. 40A and B: This figure shows in a second experiment that intravenous injection of NorBIRT at low dose did not reverse CCI-induced mechanical allodynia in a dose depended manner after 10 days. Figure A shows the effect on the ipsilateral paw and B shows the effect on the contralateral paw, both of which evidenced that allodynia was not reversed.

DETAILED DESCRIPTION OF THE INVENTION

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "patient" or "subject" is used throughout the specification to describe an animal, preferably a human, to whom treatment, including prophylactic treatment, with the compositions according to the present invention is provided (a patient or subject in need). For treatment of those infections, conditions or disease states which are specific for a specific animal such as a human patient, the term patient refers to that specific animal. In many instances, diagnostic methods are applied to patients or subjects who are suspected of having cancer or a neuroinflammatory disease or who have cancer or a neuroinflammatory disease and the diagnostic method is used to assess the severity of the disease state or disorder.

The term "compound" is used herein to refer to any specific chemical compound disclosed herein. Within its use in context, the term generally refers to a single small molecule as disclosed herein, but in certain instances may also refer to stereoisomers and/or optical isomers (including racemic mixtures) of disclosed compounds. The term compound includes active metabolites of compounds and/or pharmaceutically acceptable salts thereof, where relevant.

The term "effective amount" is used throughout the specification to describe concentrations or amounts of formulations or other components which are used in amounts, within the context of their use, to produce an intended effect according to the present invention. The formulations or component may be used to produce a favorable change in a disease or condition treated, whether that change is a remission, a favorable physiological result, a reversal or attenuation of a disease state or condition treated, the prevention or the reduction in the likelihood of a condition or disease-state occurring, depending upon the disease or condition treated. Where formulations are used in combination, each of the formulations is used in an effective amount, wherein an effective amount may include a synergistic amount. The amount of formulation used in the present invention may vary according to the nature of the formulation, the age and weight of the patient and numerous other factors which may influence the bioavailability and pharmacokinetics of the formulation, the amount of formulation which is administered to a patient generally ranges from about 0.001 mg/kg to about 50 mg/kg or more, about 0.5 mg/kg to about 25 mg/kg, about 0.1 to about 15 mg/kg, about 1 mg to about 10 mg/kg per day and otherwise described herein. The person of ordinary skill may easily recognize variations in dosage schedules or amounts to be made during the course of therapy.

The term "prophylactic" is used to describe the use of a formulation described herein which reduces the likelihood of an occurrence of a condition or disease state in a patient or subject. The term "reducing the likelihood" refers to the fact that in a given population of patients, the present invention may be used to reduce the likelihood of an occurrence, recurrence or metastasis of disease in one or more patients within that population of all patients, rather than prevent, in all patients, the occurrence, recurrence or metastasis of a disease state.

The term "pharmaceutically acceptable" refers to a salt form or other derivative (such as an active metabolite or prodrug form) of the present compounds or a carrier, additive or excipient which is not unacceptably toxic to the subject to which it is administered.

The term "chelate", "chelator", "chelating agent" or "chelating moiety" is used to describe a moiety (as included in X or $R_3$ or otherwise in generic structures) which is functionally capable of complexing or "chelating" a radioisotope as otherwise described herein. Each is appropriately chemically linked (via covalent linkers to LFA-1 moieties as otherwise described herein). Exemplary chelators for use in the present invention, which are well known in the art, include the following:

Polyaminocarboxylates, such as
EDTA: ethylenediaminetetraacetic acid
DTPA: diethylenetriaminepentaacetic acid
Polyaminocarboxylic Macrocycles, such as:
DOTA: 1,4,7,10-tetraazacyclododecane-1,4,7,10-tetraacetic acid
TRITA: 1,4,7,10-tetraazacyclotridecane-1,4,7,10-tetraacetic acid
TETA: triethylenetetramine bridged-cyclam-2a: 1,4,8,11-tetraazabicyclo[6.6.2]hexadecane-1,8-di(methanephosphonic acid)
DO3A: 1,4,7-tris(carboxymethyl)-1,4,7,10-tetraazacyclododecane
DO2A: 1,4,7,10-tetraazacyclododecane-1,7-bis(acetic acid)
Other Chelators, such as:
CB-TE2A (4,11-bis(carboxymethyl)-1,4,8,11-tetraazabicyclo[6.6.2]hexadecane)
NOTA (1,4,7-triazacyclononane-1,4,7-triacetic acid)
$MAG_3$ (Mercaptoacetyltriglycine)
4,5-bis(2-mercaptoacetamido)pentanoic acid.

Chelates, chelators or chelating agents are generally bi- or multidentate ligands which generally produce a binding or complexation (complex) of a metal radioisotope as otherwise described herein. The ligand or chelator forms a chelate complex with the substrate. The term, without limitation, is used to describe complexes in which the metal ion is bound to two or more atoms of the chelating agent by whatever means (e.g., coordinate binding or complexation) occurs when a radioisotope and chelate group complex within each other in compounds according to the present invention. It is noted here that when a chelator is complexed to a radioisotope as used herein, the chelate complex structure is represented in a generic, nonlimiting sense, such that bonds which are represented may occur between a radioistope and the chelating agent, as well as additional bonds (such as between carbonyl/carboxyl groups) which are not specifically represented, but which are understood/determined to be bonded within the context of the chelate complex (to accommodate that different radioisotopes may bind differently to different chelate groups).

The term "DOTA" is used as an abbreviation for 1,4,7,10-tetraazacyclododecane-1,4,7,10-tetraacetic acid, a preferred chelator for use in the present invention, which chemical structure (bonded in compounds according to the present invention) is represented as follows:

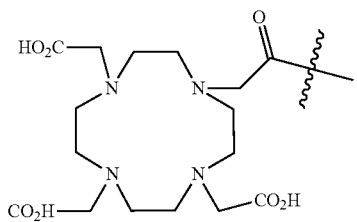

Complexed with radioisotopes according to the present invention, DOTA has the general (note that this general structure also includes the possibility of carbonyl/carboxyl groups also contributing to the complex depending on the radioisotope as in the Danbirt chemical structure identified above and is non-limiting) structure:

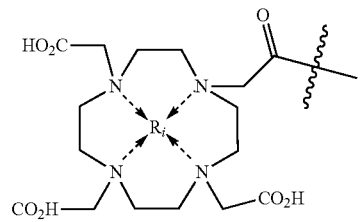

Where Ri is a radioisotope as otherwise disclosed herein.

The term "coadministration" is used to describe the administration of two or more active compounds, in this case a compound according to the present invention, in combination with an additional therapeutic agent which is used to treat neuropathic pain (a therapeutic neuropathic agent) or other biologically active agent, in effective amounts. Although the term coadministration preferably includes the administration of two or more active compounds to the patient at the same time, it is not necessary that the compounds actually be administered at the exact same time, only that amounts of compound will be administered to a patient or subject such that effective concentrations are found in the blood, serum or plasma, or in the pulmonary tissue at the same time. For example, LFA-1 antagonist compounds according to the present invention may be coadministered with (1) a non-viral plasmid DNA vector which expresses an interleukin selected from the group consisting of IL-10, IL-2, IL-4 and TGF-β (2) an IL-1 receptor antagonist, and (3) alpha-melanocyte stimulating hormone (alpha-MSH) ("therapeutic neuropathic agent"). In alternative embodiments, LFA1 antagonists may be combined with the above therapeutic neuropathic agents to provide pharmaceutical compositions as described herein.

The term "chronic neuropathic pain" is used to describe neuropathic pain which lasts for a duration of time and may be cause by nerve damage, resulting in a lengthy and painful condition. Neuropathic pain is pain which results from damage or disease affecting the somatosensory system. It may be associated with abnormal sensations called dyesthesia and pain produced by normally non-painful stimuli (allodynia). Neuropathic pain may have continuous and/or episodic (paroxysmal) components. The latter are likened to an electric shock. Common qualities include burning or coldness, "pins and needles" sensations, numbness and itching. Nociceptive pain, by contrast, is more commonly described as aching pain.

Up to 7% to 8% of the population is affected and in 5% of persons it may be severe. Neuropathic pain may result from disorders of the peripheral nervous system or the central nervous system (brain and spinal cord). Thus, neuropathic pain may be divided into peripheral neuropathic pain, central neuropathic pain, or mixed (peripheral and central) neuropathic pain.

Central neuropathic pain is found in spinal cord injury, multiple sclerosis, and some strokes. Aside from diabetes (diabetic neuropathy) and other metabolic conditions, the common causes of painful peripheral neuropathies are herpex zoster infection, HIV-related neuropathies, nutritional deficiencies, toxins, remote manifestations of malignancies, immune mediated disorders and physical trauma to a nerve trunk. Neuropathic pain is common in cancer as a direct result of cancer on peripheral nerves (e.g., compression by a tumor), or as a side effect of chemotherapy radiation injury or surgery.

Formulations of the invention may include a pharmaceutically acceptable diluent, carrier, solubilizer, emulsifier, preservative and/or adjuvant. Acceptable formulation materials preferably are nontoxic to recipients at the dosages and concentrations employed. The pharmaceutical formulations may contain materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S. PHARMACEUTICAL SCIENCES, 18.sup.th Edition, (A. R. Gennaro, ed.), 1990, Mack Publishing Company.

Optimal pharmaceutical formulations can be determined by one skilled in the art depending upon, for example, the intended route of administration, delivery format and desired dosage. See, for example, REMINGTON'S PHARMACEUTICAL SCIENCES, Id. Such formulations may influence the physical state, stability, rate of in vivo release and rate of in vivo clearance of the antibodies of the invention.

Primary vehicles or carriers in a pharmaceutical formulation can include, but are not limited to, water for injection, physiological saline solution or artificial cerebrospinal fluid, possibly supplemented with other materials common in compositions for parenteral administration, especially intravenous administration. Neutral buffered saline or saline mixed with serum albumin are further exemplary vehicles. Pharmaceutical formulations can comprise Tris buffer of about pH 7.0-8.5, or acetate buffer of about pH 4.0-5.5, which may further include sorbitol or a suitable substitute. Pharmaceutical formulations of the invention may be prepared for storage by mixing the selected composition having the desired degree of purity with optional formulation agents (REMINGTON'S PHARMACEUTICAL SCIENCES, Id.) in the form of a lyophilized cake or an aqueous solution. Further, the formulations may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical formulations of the invention can be delivered parenterally. When parenteral administration is contemplated, the therapeutic formulations for use in this invention may be in the form of a pyrogen-free, parenterally acceptable aqueous solution. Preparation involves the formulation of the desired immunomicelle, which may provide controlled or sustained release of the product which may then be delivered via a depot injection. Formulation with hyaluronic acid has the effect of promoting sustained duration in the circulation.

Formulations may be formulated for inhalation. In these embodiments, a stealth immunomicelle formulation is formulated as a dry powder for inhalation, or inhalation solutions may also be formulated with a propellant for aerosol delivery, such as by nebulization. Pulmonary administration is further described in PCT Application No. PCT/US94/001875, which describes pulmonary delivery of chemically modified proteins and is incorporated by reference.

Formulations of the invention can be delivered through the digestive tract, such as orally. The preparation of such pharmaceutically acceptable compositions is within the skill of the art. Formulations disclosed herein that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized Additional agents can be included to facilitate absorption. Diluents, flavorings, low melting point waxes, vegetable oils, lubricants, suspending agents, tablet disintegrating agents, and binders may also be employed.

A formulation may involve an effective quantity of a micropoarticle containing formulation as a sustained or controlled release composition in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once the formulation of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

Administration routes for formulations of the invention include orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. The pharmaceutical formulations may be administered by bolus injection or continuously by infusion, or by implantation device. The pharmaceutical formulations also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration. Compositions according to the present invention, including those which comprise microparticles are preferably administered by intrathecal administration. LFA1 compounds are often administered parenterally, including when coadministered with at least one therapeutic neuropathic agent, which are often administered intrathecally.

The following descriptions and definitions from U.S. Patent Application Document No. 20130236509, modified as noted below, are applicable with respect to the term "microparticle".

"'[M]icroparticle'" as used herein encompasses 'nanoparticles", "microcapsules", "microbeads", and "microspheres". [Preferably] the microparticle as used herein is a biodegradable particle which is smaller than 3.5 gm and larger than 0.2 gm, preferably smaller than 2 gm and larger than 1 gm. The size of a microparticle as specified herein refers to the mean particle diameter. The size of the microparticle is important because the microparticle must be phagocytosed by phagocytes in order to activate the phagocytes through the release of the small heat shock proteins as indicated herein. Activation of the macrophages becomes apparent from the induction of IL-10 production by the macrophage.

The microparticle may have any form, including a substantially spherical and irregular form. If a microparticle is not spherical, the term diameter refers to the inner diameter of the smallest spherical structure wherein said microparticle would fit. A microparticle can be a homogeneous microparticle. The term "homogeneous microparticle" as used herein refers to a microparticle having its active agent (i.e. alpha-crystallin) dispersed or dissolved throughout the microparticle. Homogeneous microparticles are preferably structurally formed by a matrix of an excipient, usually a polymeric excipient. Preferably, in homogeneous microparticles, said polymeric excipient is a biodegradable polymer. Preferably, said biodegradable polymer is present throughout each homogeneous microparticle, with the active agent captured within the biodegradable polymer molecules. Said polymeric excipient may be of the same polymer or contain a mix of different types of polymers.

Other microparticles which may be used in aspects of the invention are encapsulating microparticles.

The term "biodegradable microparticle" as used herein refers to the capacity of a microparticle to be broken down into smaller fragments or to release an active agent over time under physiological conditions. Degradation may occur, for example, by enzymatic, chemical or physical processes. Biodegradable microparticles typically release their agent via a combination of drug diffusion and polymer erosion. Preferably, such smaller fragments are smaller than 90, 80, 70, 60, 50, 40, 30, 20, 10, 5, 4, 3, 2, 1% of the biodegradable microparticle diameter which the microparticle had before it was exposed to a fluid under physiological conditions. In preferred embodiments of biodegradable microparticles, a smaller fragment refers to fragments smaller than 50, 40, 30, 20, 10 nm.

The term "biodegradable polymer" as used herein refers to a polymer which is degraded over time under physiological conditions as described above. Examples of biodegradable polymers include those having at least some repeating units representative of at least one of the following: an alpha-hydroxycarboxylic acid, a cyclic diester of an alpha-hydroxycarboxylic acid, a dioxanone, a lactone, a cyclic carbonate, a cyclic oxalate, an epoxide, a glycol, and anhydrides. Preferred biodegradable polymers comprise at least some repeating units representative of polymerizing at least one of lactic acid, glycolic acid, lactide, glycolide, ethylene oxide and ethylene glycol.

Preferred biodegradable polymers include poly(lactide)s, poly(glycolide)s, poly(lactic acid)s, poly(glycolic acid)s, polyanhydrides, polyorthoesters, polyetheresters, polycaprolactone, polyesteramides, polycarbonate, polycyanoacrylate, polyurethanes, polyacrylate, blends and copolymers thereof.

The range of molecular weights contemplated for the polymers to be used in the present processes can be readily determined by a person skilled in the art based upon factors such as the desired polymer degradation rate, or preferably the level macrophage activation under (simulated) in vivo conditions, preferably in humans. Typically, the range of molecular weight is between 2000 to 2,000,000 Daltons.

Preferred polymers are selected from ε-caprolactone, polylactic acid (PLA), polylactic-co-glycolic acid (PLGA) and polylactic-co-hydroxymethylglycolic acid (PLHMGA)."

The wide variety of microparticle manufacturing techniques described in U.S. Patent Application Document No. 20130236509 are also applicable to the manufacture of microparticles that can be used in the invention.

Microcapsules according to the present invention include at least one therapeutic neuropathic agent and optionally, at least one LFA1 antagonist. The LFA1 antagonist may be combined in the microcapsule, or alternatively coadministered with microcapsules which comprise the therapeutic neuropathic agent(s).

The term "protocell" is used to describe a porous nanoparticle which is made of a material comprising, e.g. silica, polystyrene, alumina, titania, zirconia, or generally metal oxides, organometallates, organosilicates or mixtures thereof.

In certain embodiments, the porous particle core may be hydrophilic and can be further treated to provide a more hydrophilic surface in order to influence pharmacological result in a particular treatment modality. For example, mesoporous silica particles according to the present invention can be further treated with, for example, ammonium hydroxide or other bases and hydrogen peroxide to provide significant hydrophilicity. The use of amine containing silanes such as 3-[2-(2-aminoethylamino)ethylamino] propyltrimethoxysilane (AEPTMS), among others, may be used to produce negatively charged cores which can markedly influence the cargo loading of the particles. Other agents may be used to produce positively charged cores to influence in the cargo in other instances, depending upon the physicochemical characteristics of the cargo.

Nanoparticules according to the present invention comprise a lipid bilayer which coats its surface to form a structure referred to as a protocell. While numerous lipids and phospholipids may be used to provide a lipid bilayer for use in the present invention, in certain preferred embodiments, the lipid bilayer comprises a phospholipid selected from the group consisting of phosphatidyl choline, 1,2-Dioleoyl-3-Trimethylammonium-propane (DOTAP), 1,2-Dioleoyl-sn-Glycero-3-Phosphocholine (DOPC), 1,2-dioleoyl-sn-glycero-3-phosphoethanolamine-N-[methoxy (polyethylene glycol)-2000, 1,2-dioleoyl-sn-glycero-3-phosphoethanolamine (DOPE) or mixtures thereof. In addition to a phospholipid, including the specific phospholipids as otherwise described herein, the lipid bilayer may also comprise cholesterol (for structural integrity of the lipid bilayer) as well as polyethylene glycol lubricants/solvents (e.g. PEG 2000, etc.) to provide flexibility to the lipid bilayer. In addition to fusing a single phospolipid bilayer, multiple bilayers with opposite charges may be fused onto the porous particles in order to further influence cargo loading, sealing and release of the particle contents in a biological system.

In certain embodiments, the lipid bilayer can be prepared, for example, by extrusion of hydrated lipid films through a filter of varying pore size (e.g., 50, 100, 200 nm) to provide filtered lipid bilayer films, which can be fused with the porous particle cores, for example, by pipette mixing or other standard method.

In various embodiments, the protocell (nanoparticle to which a lipid bilayer covers or is otherwise fused to the particle) can be loaded with and seal macromolecules (siR- NAs and polypeptide toxins) as otherwise described herein, thus creating a loaded protocell useful for cargo delivery across the cell membrane In preferred aspects of the present invention, the nanoparticles (preferably encapsulated with a lipid bilayer) provide a targeted delivery through conjugation of certain targeting peptides onto the protocell surface, preferably by conjugation to the lipid bilayer surface. These peptides include SP94 and H5WYG peptides which may be synthesized with C-terminal cysteine residues and conjugated to one or more of the phospholipids (especially, DOPE, which contains a phosphoethanolamine group) which comprise the lipid bilayer.

As used herein, unless otherwise specified, the term "protocell" is used to refer to a nanostructure having a porous particle and a lipid bilayer surrounding the porous particle. The protocell can mimic bioactive cells (or real cells) that have a supported lipid bilayer membrane. For example, the porous particle can be made of a material including polystyrene, silica, alumina, titania, zirconia, etc. In embodiments, the porous particle can have a controllable average pore size ranging from about 2 nm to about 30 nm, and an average porosity ranging from about 10% to about 70%, for example, ranging from about 25% to about 50%. The porous particle can have an average particle size ranging from about 30 nm to about 3000 nm.

The porous particle, such as porous silica particles, can be surface charged. For example, the surface charge of the porous silica particles can switch from negative to positive at neutral pHs by using amine-modified silane precursors and controlling the percentage of amine groups within the porous silica particles. For example, the porous silica particles can have a composition of about 5% to about 50% amine, such as about 10% to about 50% amine, or about 5% to about 30% amine by weight; and the amine-modified silane precursors can include, for example,

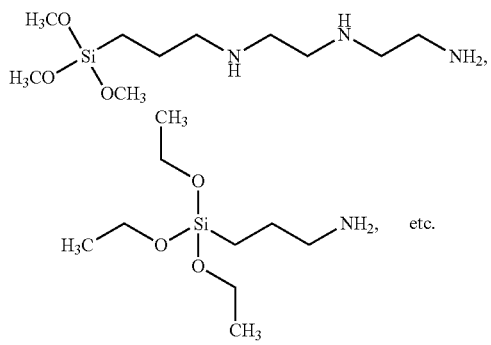

The porous silica particles can be formed by, for example, mixing water, HCl, ethanol, cetyltrimethylamonium bromide (CTAB), and tetraethyl orthosilicate (TEOS), as disclosed in a related International Patent Application No. PCT/US10/20096, entitled "Porous Nanoparticle Supported Lipid Bilayer Nanostructures," which is hereby incorporated by reference in its entirety.

Porous nanoparticulates used in protocells of the invention include mesoporous silica nanoparticles and core-shell nanoparticles.

The porous nanoparticulates can also be biodegradable polymer nanoparticulates comprising one or more compositions selected from the group consisting of aliphatic polyesters, poly (lactic acid) (PLA), poly(glycolic acid) (PGA), co-polymers of lactic acid and glycolic acid (PLGA), polycaprolactone (PCL), polyanhydrides, poly(ortho)esters, polyurethanes, poly(butyric acid), poly(valeric acid), poly (lactide-co-caprolactone), alginate and other polysaccharides, collagen, and chemical derivatives thereof, albumin a hydrophilic protein, zein, a prolamine, a hydrophobic protein, and copolymers and mixtures thereof.

A porous spherical silica nanoparticle is used for the preferred protocells and is surrounded by a supported lipid or polymer bilayer or multilayer. Various embodiments according to the present invention provide nanostructures and methods for constructing and using the nanostructures and providing protocells according to the present invention. Many of the protocells in their most elemental form are known in the art. Porous silica particles of varying sizes ranging in size (diameter) from less than 5 nm to 200 nm or 500 nm or more are readily available in the art or can be readily prepared using methods known in the art (see the examples section) or alternatively, can be purchased from Melorium Technologies, Rochester, N.Y. SkySpring Nanomaterials, Inc., Houston, Tex., USA or from Discovery Scientific, Inc., Vancouver, British Columbia. Multimodal silica nanoparticles may be readily prepared using the procedure of Carroll, et al., *Langmuir,* 25, 13540-13544 (2009). Protocells can be readily obtained using methodologies known in the art. The examples section of the present application provides certain methodology for obtaining protocells which are useful in the present invention. Protocells according to the present invention may be readily prepared, including protocells comprising lipids which are fused to the surface of the silica nanoparticle. See, for example, Liu, et al., *Chem. Comm.,* 5100-5102 (2009), Liu, et al., *J. Amer. Chem. Soc.,* 131, 1354-1355 (2009), Liu, et al., J. Amer. Chem. Soc., 131, 7567-7569 (2009) Lu, et al., *Nature,* 398, 223-226 (1999), Preferred protocells for use in the present invention are prepared according to the procedures which are presented in Ashley, et al., *Nature Materials,* 2011, May; 10(5):389-97, Lu, et al., *Nature,* 398, 223-226 (1999), Caroll, et al., *Langmuir,* 25, 13540-13544 (2009), and as otherwise presented in the experimental section which follows. A recent publication which details the incorporation and delivery of therapeutic neuropathic pain agents as described herein (as DNA cargbo) which may be delivered to the spinal column of a patient intrathecally is Dengler, et al., *Journal of Controlled Release,* 168, pp. 209-224 (2013), the teachings of which are incorporated by reference herein.

The terms "nanoparticulate" and "porous nanoparticulate" are used interchangeably herein and such particles may exist in a crystalline phase, an amorphous phase, a semi-crystalline phase, a semi amorphous phase, or a mixture thereof.

A nanoparticle may have a variety of shapes and cross-sectional geometries that may depend, in part, upon the process used to produce the particles. In one embodiment, a nanoparticle may have a shape that is a sphere, a rod, a tube, a flake, a fiber, a plate, a wire, a cube, or a whisker. A nanoparticle may include particles having two or more of the aforementioned shapes. In one embodiment, a cross-sectional geometry of the particle may be one or more of circular, ellipsoidal, triangular, rectangular, or polygonal. In one embodiment, a nanoparticle may consist essentially of non-spherical particles. For example, such particles may have the form of ellipsoids, which may have all three principal axes of differing lengths, or may be oblate or prelate ellipsoids of revolution. Non-spherical nanoparticles alternatively may be laminar in form, wherein laminar refers to particles in which the maximum dimension along one axis is substantially less than the maximum dimension along each of the other two axes. Non-spherical nanoparticles may also have the shape of frusta of pyramids or cones, or of elongated rods. In one embodiment, the nanoparticles may be irregular in shape. In one embodiment, a plurality of nanoparticles may consist essentially of spherical nanoparticles.

The phrase "effective average particle size" as used herein to describe a multiparticulate (e.g., a porous nanoparticulate) means that at least 50% of the particles therein are of a specified size. Accordingly, "effective average particle size of less than about 2,000 nm in diameter" means that at least 50% of the particles therein are less than about 2000 nm in diameter. In certain embodiments, nanoparticulates have an effective average particle size of less than about 2,000 nm (i.e., 2 microns), less than about 1,900 nm, less than about 1,800 nm, less than about 1,700 nm, less than about 1,600 nm, less than about 1,500 nm, less than about 1,400 nm, less than about 1,300 nm, less than about 1,200 nm, less than about 1,100 nm, less than about 1,000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods. "$D_{50}$" refers to the particle size below which 50% of the particles in a multiparticulate fall. Similarly, "$D_{90}$" is the particle size below which 90% of the particles in a multiparticulate fall.

In certain embodiments, the porous nanoparticulates are comprised of one or more compositions selected from the group consisting of silica, a biodegradable polymer, a solgel, a metal and a metal oxide.

In an embodiment of the present invention, the nanostructures include a core-shell structure which comprises a porous particle core surrounded by a shell of lipid preferably a bilayer, but possibly a monolayer or multilayer (see Liu, et al., *JAGS*, 2009, Id). The porous particle core can include, for example, a porous nanoparticle made of an inorganic and/or organic material as set forth above surrounded by a lipid bilayer. In the present invention, these lipid bilayer surrounded nanostructures are referred to as "protocells" or "functional protocells," since they have a supported lipid bilayer membrane structure. In embodiments according to the present invention, the porous particle core of the protocells can be loaded with various desired species ("cargo"), including small molecules (e.g. anticancer agents as otherwise described herein), large molecules (e.g. including macromolecules such as RNA, including small interfering RNA or siRNA or small hairpin RNA or shRNA or a polypeptide which may include a polypeptide toxin such as a ricin toxin A-chain or other toxic polypeptide such as diphtheria toxin A-chain DTx, among others) or a reporter polypeptide (e.g. fluorescent green protein, among others) or semiconductor quantum dots, or metallic nanparticles, or metal oxide nanoparticles or combinations thereof. In certain preferred aspects of the invention, the protocells are loaded with super-coiled plasmid DNA, which can be used to deliver a therapeutic and/or diagnostic peptide(s) or a small hairpin RNA/shRNA or small interfering RNA/siRNA which can be used to inhibit expression of proteins.

In certain embodiments, the cargo components can include, but are not limited to, chemical small molecules (e.g. a LFA1 antagonist), nucleic acids (DNA and RNA, including siRNA and shRNA and plasmids which, after delivery to a cell, express one or more polypeptides or RNA molecules), such as for a particular purpose, such as a therapeutic application or a diagnostic application as otherwise disclosed herein.

In embodiments, the lipid bilayer of the protocells can provide biocompatibility and can be modified to possess targeting species including, for example, targeting peptides including antibodies, aptamers, and PEG (polyethylene glycol) to allow, for example, further stability of the protocells and/or a targeted delivery into a bioactive cell.

The protocells particle size distribution, according to the present invention, depending on the application, may be monodisperse or polydisperse. The silica cores can be rather monodisperse (i.e., a uniform sized population varying no more than about 5% in diameter e.g., ±10-nm for a 200 nm diameter protocell especially if they are prepared using solution techniques) or rather polydisperse (i.e., a polydisperse population can vary widely from a mean or medium diameter, e.g., up to ±200-nm or more if prepared by aerosol. Polydisperse populations can be sized into monodisperse populations. All of these are suitable for protocell formation. In the present invention, preferred protocells are preferably no more than about 500 nm in diameter, preferably no more than about 200 nm in diameter in order to afford delivery to a patient or subject and produce an intended therapeutic effect.

In one example, a high surface area (i.e., greater than about 600 m$^2$/g, preferably about 600 to about 1,000-1,250 mg$^2$/g), preferably monodisperse spherical silica or other biocompatible material nanoparticles having diameters falling within the range of about 0.05 to 50 µm, preferably about 1,000 nm or less, more preferably about 100 nm or less, 10-20 nm in diameter, a multimodal pore morphology comprising large (about 1-100 nm, preferably about 2-50 nm, more preferably about 10-35 nm, about 20-30 nm) surface-accessible pores interconnected by smaller internal pores (about 2-20 nm, preferably about 5-15 nm, more preferably about 6-12 nm) volume, each nanoparticle comprising a lipid bilayer (preferably a phospholipid bilayer) supported by said nanoparticles (the phospholipic bilayer and silica nanoparticles together are labeled "protocells" as otherwise described herein), to which is bound at least one antigen which binds to a targeting polypeptide or protein on a cell to which the protocells are to be targeted, wherein the protocells further comprise (are loaded) with a LFA1 antagonist, a non-viral plasmid DNA vector which expresses an interleukin selected from the group consisting of IL-10, IL-2, IL-4 and TGF-β and/or a macromolecule selected from the group consisting of a small interfering RNA (siRNA) or a polypeptide toxin (e.g. ricin toxin A-chain or other toxic polypeptide).

The term "monodisperse" is used as a standard definition established by the National Institute of Standards and Technology (NIST) (*Particle Size Characterization, Special Publication* 960-1, January 2001) to describe a distribution of particle size within a population of particles, in this case nanoparticles, which particle distribution may be considered monodisperse if at least 90% of the distribution lies within 5% of the median size. See Takeuchi, et al., *Advanced Materials,* 2005, 17, No. 8, 1067-1072.

In certain embodiments, protocells according to the present invention generally range in size from greater than about 8-10 nm to about 5 μm in diameter, preferably about 20-nm-3 μm in diameter, about 10 nm to about 500 nm, more preferably about 20-200-nm (including about 150 nm, which may be a mean or median diameter). As discussed above, the protocell population may be considered monodisperse or polydisperse based upon the mean or median diameter of the population of protocells. Size is very important to therapeutic and diagnostic aspects of the present invention as particles smaller than about 8-nm diameter are excreted through kidneys, and those particles larger than about 200 nm are trapped by the liver and spleen. Thus, an embodiment of the present invention focuses in smaller sized protocells for drug delivery and diagnostics in the patient or subject.

In certain embodiments, protocells according the present invention are characterized by containing mesopores, preferably pores which are found in the nanostructure material. These pores (at least one, but often a large plurality) may be found intersecting the surface of the nanoparticle (by having one or both ends of the pore appearing on the surface of the nanoparticle) or internal to the nanostructure with at least one or more mesopore interconnecting with the surface mesopores of the nanoparticle. Interconnecting pores of smaller size are often found internal to the surface mesopores. The overall range of pore size of the mesopores can be 0.03-50-nm in diameter. Preferred pore sizes of mesopores range from about 2-30 nm; they can be monosized or bimodal or graded—they can be ordered or disordered (essentially randomly disposed or worm-like).

Mesopores (IUPAC definition 2-50-nm in diameter) are 'molded' by templating agents including surfactants, block copolymers, molecules, macromolecules, emulsions, latex beads, or nanoparticles. In addition, processes could also lead to micropores (IUPAC definition less than 2-nm in diameter) all the way down to about 0.03-nm e.g. if a templating moiety in the aerosol process is not used. They could also be enlarged to macropores, i.e., 50-nm in diameter.

Pore surface chemistry of the nanoparticle material can be very diverse—all organosilanes yielding cationic, anionic, hydrophilic, hydrophobic, reactive groups—pore surface chemistry, especially charge and hydrohobicity, affect loading capacity. See FIG. 3, attached. Attractive electrostatic interactions or hydrophobic interactions control/enhance loading capacity and control release rates. Higher surface areas can lead to higher loadings of drugs/cargos through these attractive interactions. See below.

In certain embodiments, the surface area of nanoparticles, as measured by the N2 BET method, ranges from about 100 m2/g to > about 1200 m2/g. In general, the larger the pore size, the smaller the surface area. See table FIG. 2A. The surface area theoretically could be reduced to essentially zero, if one does not remove the templating agent or if the pores are sub-0.5-nm and therefore not measurable by N2 sorption at 77K due to kinetic effects. However, in this case, they could be measured by CO2 or water sorption, but would probably be considered non-porous. This would apply if biomolecules are encapsulated directly in the silica cores prepared without templates, in which case particles (internal cargo) would be released by dissolution of the silica matrix after delivery to the cell.

Typically the protocells according to the present invention are loaded with cargo to a capacity up to about 50 weight %: defined as (cargo weight/weight of loaded protocell)×100. The optimal loading of cargo is often about 0.01 to 10% but this depends on the drug or drug combination which is incorporated as cargo into the protocell. This is generally expressed in µM per $10^{10}$ particles where we have values ranging from 2000-100 µM per $10^{10}$ particles. Preferred protocells according to the present invention exhibit release of cargo at pH about 5.5, which is that of the endosome, but are stable at physiological pH of 7 or higher (7.4).

The surface area of the internal space for loading is the pore volume whose optimal value ranges from about 1.1 to 0.5 cubic centimeters per gram (cc/g). Note that in the protocells according to one embodiment of the present invention, the surface area is mainly internal as opposed to the external geometric surface area of the nanoparticle.

The lipid bilayer supported on the porous particle according to one embodiment of the present invention has a lower melting transition temperature, i.e. is more fluid than a lipid bilayer supported on a non-porous support or the lipid bilayer in a liposome. This is sometimes important in achieving high affinity binding of targeting ligands at low peptide densities, as it is the bilayer fluidity that allows lateral diffusion and recruitment of peptides by target cell surface receptors. One embodiment provides for peptides to cluster, which facilitates binding to a complementary target.

In the present invention, the lipid bilayer may vary significantly in composition. Ordinarily, any lipid or polymer which is may be used in liposomes may also be used in protocells. Preferred lipids are as otherwise described herein. Particularly preferred lipid bilayers for use in protocells according to the present invention comprise a mixtures of lipids (as otherwise described herein) at a weight ratio of 5% DOPE, 5% PEG, 30% cholesterol, 60% DOPC or DPPC (by weight).

The charge of the mesoporous silica NP core as measured by the Zeta potential may be varied monotonically from −50 to +50 mV by modification with the amine silane, 2-(aminoethyl) propyltrimethoxy-silane (AEPTMS) or other organosilanes. This charge modification, in turn, varies the loading of the drug within the cargo of the protocell. Generally, after fusion of the supported lipid bilayer, the zeta-potential is reduced to between about −10 mV and +5 mV, which is important for maximizing circulation time in the blood and avoiding non-specific interactions.

Depending on how the surfactant template is removed, e.g. calcination at high temperature (500° C.) versus extraction in acidic ethanol, and on the amount of AEPTMS incorporated in the silica framework, the silica dissolution rates can be varied widely. This in turn controls the release rate of the internal cargo. This occurs because molecules that are strongly attracted to the internal surface area of the pores diffuse slowly out of the particle cores, so dissolution of the particle cores controls in part the release rate.

In one illustrative embodiment, a protocell used in the methods of treatment and pharmaceutical compositions of the invention comprises:

(a) a core comprising a plurality of negatively-charged, nanoporous, nanoparticulate silica cores that are optionally modified with an amine-containing silane and that are interspersed with one or more LFA1 antagonists and, optionally, a non-viral plasmid DNA vector which expresses an interleukin selected from the group consisting of IL-10, IL-2, IL-4 and TGF-β; and (b) a lipid bilayer which encapsulates the core and which comprises one of more lipids selected from the group consisting of 1,2-dioleoyl-sn-glycero-3-phosphocholine (DOPC), 1,2-dipalmitoyl-sn-glycero-3-phosphocholine (DPPC), dioleylglycero triethyleneglycyl iminodiacetic acid (DOIDA), distearylglycerotriethyleneglycyl iminodiacetic acid (DSIDA), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3- phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino]lauroyl]-sn-Glycero-3-Phosphocholine (18:1-12:0 NBD PC), 1-palmitoyl-2-{12-[(7-nitro-2-1,3-benzoxadiazol-4-yl)amino]lauroyl}-sn-glycero-3-phosphocholine (16:0-12:0 NBD PC), cholesterol and mixtures/combinations thereof, wherein the lipid bilayer optionally comprises a cationic lipid and one or more zwitterionic phospholipids and contains on its surface at least one peptide that targets a proinflammatory cytokine. Protocells may optionally comprise at least one LFA1 antagonist as described herein.

These and other aspects of the invention are described further in the following illustrative examples.

Example 1

Vector Screening, to Deliver the IL-10 Gene to the Spinal Cord for Chronic Spinal Delivery of Protein IL-10 to Target the Function of Glia Rather than Neurons.

We sought to identify the best vector system, either of the viral-based adeno-associated virus (AAV) or the non-viral DNA-based vector (plasmid DNA; pDNA), to achieve therapeutic pain control when delivered to the spinal subarachnoid space (IT). Diverse pathological pain models were successfully prevented and reversed for up to a maximum of 2 weeks by using either replication defective Adenoviral or Adeno-Associated viral vectors encoding IL-10. Several doses that produced pain relief also revealed IL-10 gene expression as measured by protein release into the surrounding CSF [89, 93]. While successful, the viral vectors were short-lived in their effects when one considers clinical neuropathic pain control. Studies comparing spinal transgene expression from various AAV strains (AAV4, AAV5 & AAV6), as examined by techniques for immunohistochemistry (IHC) and pain assessment, was comparable to that observed with AAV2. While continued progress toward designing improved viral vector systems may be worthy of future exploration [6], the optimal vector identified for long-duration pain control during the current grant period was determined to be free pDNA encoding the IL-10 gene (FIG. 2). Behavioral pain assessment is conducted as previously described [90]. Briefly, rats are placed in a quite, dimly lit room and allowed to habituate to the testing environment for 4 consecutive days, 1 hr/day. Baseline (BL) responses are assessed with a series of graded calibrated filaments (0.4 g-15.0 g) applied to the plantar surface of the hindpaws for 6 sec, which elicits a reliable paw withdrawal response [17]. The pDNA-based vector used in data described here and in 'Preliminary Data' contains inverted terminal repeat (ITRs) palindromic nucleotide sequences that are residual components from the original AAV vector and provide additional promoter activity, albeit, somewhat weak. [38]. Therefore ITRs would only serve to augment the transcription driven by the expression cassette. The transcriptional cassette contains the cytomegalovirus enhancer/chicken b-actin promoter (CB-actin promoter), an intronic region, the rat IL-10 gene with a spontaneous point mutation (F129S) and the SV40 polyadenylation signal region.

Further, we sought to determine the best promoters from a pre-selected set that show promise for robust gene expression. We found that the CB-actin promoter produced longer lasting effects than the cytomegalovirus (CMV) promoter. Given the high degree of success observed with the non-viral pDNA vector, we did not continue to screen other promoters.

Example 2

IT pDNA-IL-10 Produced Substantially Greater mRNA IL-10 Transgene Levels in DRG Examined 60 Days after IT Injection Compared to mRNA Levels from IT pDNA Chronic Pain Controls IT pDNA-IL-10 produced substantially greater mRNA IL-10 transgene levels in DRG examined 60 days after IT injection compared to mRNA levels from IT pDNA chronic pain controls (FIG. 3; pilot data). In support of long duration IT pDNA transgene expression, we recently reported pDNA encoding the reporter gene, humansecreted alkaline phosphatase, was produced and released into CSF surrounding the IT injection site though 84 days compared to corresponding controls. Virtually undetectable levels were measured from cervical CSF & serum [50]. We will extend these studies to examine long-duration pain-relief and transgene expression by utilizing pDNA that encodes both the IL-10 & the reporter gene, RFP in Aims II & III (Research Design, FIG. 18). Interestingly, IT pDNA-IL10 in healthy, non-neuropathic control groups resulted in only small increases in IL-10 transgene expression in the meninges and DRG [74]. This observation is critical because it suggests that conditions in non-pathological spinal cord are not sufficient for substantial pDNA-based IL-10 transgene expression. Indeed, pain was minimally alleviated when IT pDNA-IL-10 was injected prior to full Taxol®-induced allodynia [74]. In addition, pre-treatment with IT pDNA-IL10 two weeks prior to induction of CCI failed to prevent neuropathic pain (pilot data not shown). We speculate that pre-emptive IT pDNA-IL10 is ineffective because the local environment may not be permissive for non-viral gene uptake & subsequent expression. Clinically, gene delivery-based therapeutics will be applicable to people who have persistent pain, and not for prophylactic pain treatment.

Example 3

Discovery of Discrete Components that Make Up the Sensitization Period

Macrophages and dendritic cells are the predominant immune cells found in the meninges. Other immune cells (neutrophils & mast cells) infiltrate meninges & DRGs during neuropathic conditions [22, 148]. Thus, we began to focus on immune-mediated mechanisms in the lumbar meninges that may be responsible for transgene expression. Macrophage & microglia (stained red) in the pia mater of the meninges (FIG. 4) appeared remarkably similar to findings in a recent report identifying increases in these cell types in meninges after chronic neuropathic pain produced by partial sciatic nerve ligation [148]. Zhang and colleagues demonstrated that ~20% of these macrophage/microglia infiltrated lumbar meninges & derived from bone marrow. Also note microglial processes in spinal cord that surround blue- (DAPI) stained cell nuclei. In combination, the data suggest a local innate immune response is provoked by peripheral neuropathy.

Figure 6:
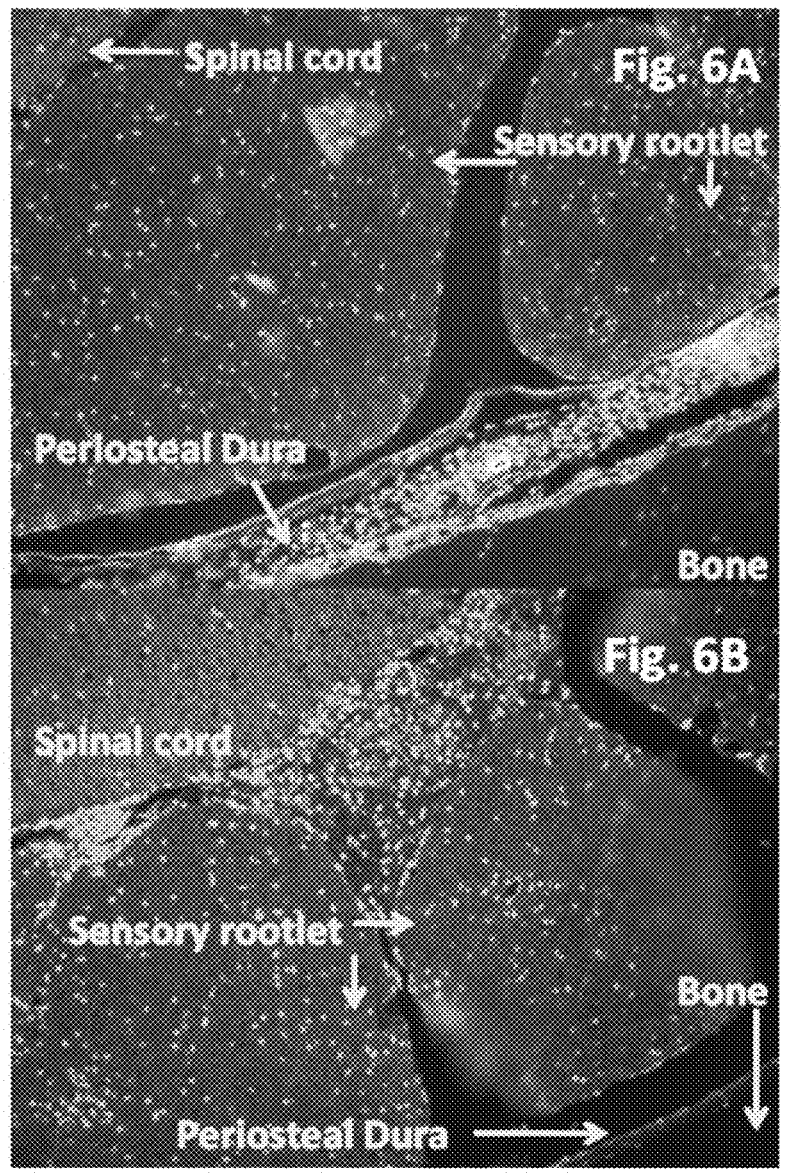
FIG. 6: the pattern of cellular nuclei present using the nuclear-specific stain, DAPI, following IT pDNA between non-neuropathic sham- and neuropathic CCI-treated rats. We observed a differential cellular distribution in the lumbosacral peri-spinal region. A high number of cells were present in the periosteal dura, a fibrous tissue layer that adjoins the vertebral bone in non-neuropathic rats (FIG. 6A; 10×). The spinal sensory rootlets and spinal cord were surrounded by normal (non-pathologic) numbers of cellular nuclei. Conversely, significant increases in DAPI-stained cellular nuclei were clustered between the spinal sensory rootlets and adjacent spinal cord. The thickness of cellular nuclei present in the periosteal dura was dramatically reduced (FIG. 6B; 10×). As determined in the experiment of Example 3.

Cell Enrichment. We discovered IT pDNA stimulates local innate immune cell enrichment. Enrichment could be responsible for subsequent IT pDNA-IL10 'uptake' of pDNA-sensitized cells. The time course of cell enrichment measured in CSF from hours to days after IT pDNA-IL-10 injection corresponds to the inter-injection intervals of IT pDNA-IL10 that produces long-duration pain relief (FIG. 5) [119]. We next examined whether the anatomical location of cellular enrichment could be identified 24 hr following a single IT pDNA injection, and if the presence of an ongoing neuropathy altered the local cellular pattern. We compared the pattern of cellular nuclei present using the nuclear-specific stain, DAPI, following IT pDNA between non-neuropathic sham- and neuropathic CCI-treated rats (FIG. 6). We observed a differential cellular distribution in the lumbosacral pen-spinal region. A high number of cells were present in the periosteal dura, a fibrous tissue layer that adjoins the vertebral bone in non-neuropathic rats (FIG. 6A; 10×). The spinal sensory rootlets and spinal cord were surrounded by normal (non-pathologic) numbers of cellular nuclei. Conversely, significant increases in DAPI-stained cellular nuclei were clustered between the spinal sensory rootlets and adjacent spinal cord. Intriguingly, the thickness of cellular nuclei present in the periosteal dura was dramatically reduced (FIG. 6B; 10×) (for review [39, 133]. This is the first demonstration showing distinct subanatomical differences in cellular enrichment of the spinal subarachnoid compartment.

Phenotypic Shift. Further, the characteristics of the population of cells in lumbar CSF shifts over a short period of time after a single IT pDNA-IL-10 injection. Prior to & at 2 hrs after IT pDNA-IL-10, a mix (~50%) of macrophages/dendritic cells were measured with either a pro-inflammatory-like or anti-inflammatory-like profile, using cell surface specific markers (EDI; pro-inflammatory & ED2; anti-inflammatory) [120]. The accumulation and phenotypic switch of cells within CSF only occurs following IT pDNA-IL-10 injection but not following control PBS injections [120]. To extend these data, we have proposed studies to determine if cell enrichment includes the population of pDNA-responsive and pDNA-sensitized cells that are also critical for transgene expression Example 4

Preventing Cell Enrichment after IT pDNA.

We postulate that cell enrichment is be required for effective IT pDNA-IL10 gene transfer and pain relief. In support of this position, IT IL-10 protein (without transgene) 4 hr prior to IT pDNA-IL10 prevented increased cellular enrichment in surrounding CSF as well as the long duration pain relief that normally occurs following IT pDNA-IL-10 injections [120]. These data further support that IT pDNA-IL-10, under permissive conditions, lead to prolonged non-viral mediated gene expression. This is an entirely novel approach for chronic pain control. These data are intriguing and the functional properties of these cells with regard to pDNA-IL10 gene expression are examined in studies described in Aim IA, B & IIA&B.

Figure 7:
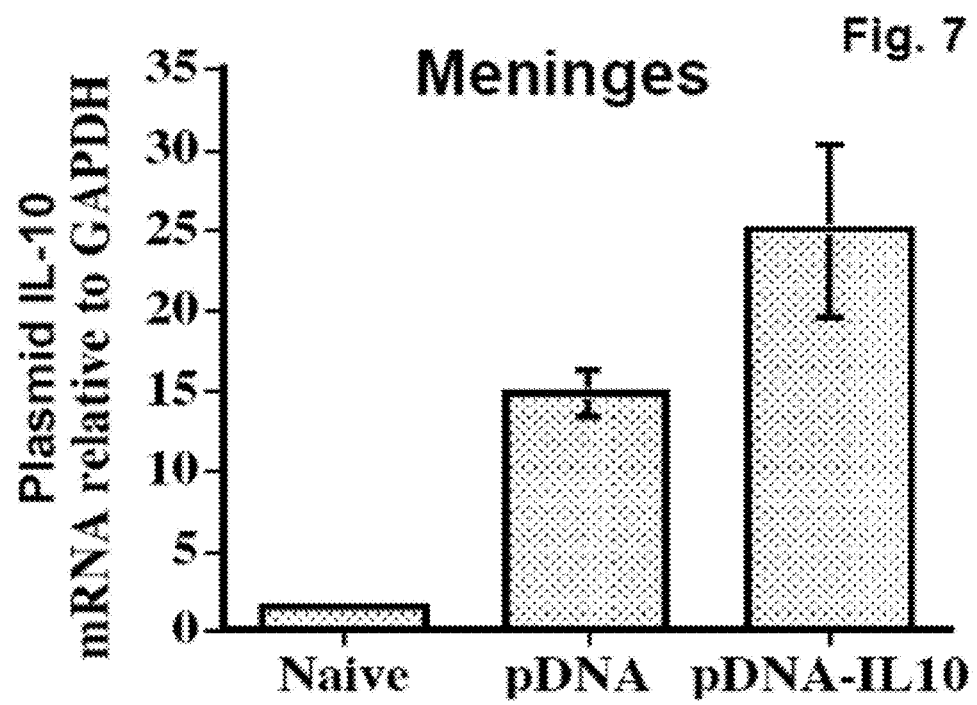
FIG. 7: IT pDNA-Control given as an initial Sensitization injection followed by IT pDNA-IL10 leads to the same pain relief profile as two IT pDNA-IL10 injections. Indeed, our pilot data show transient increases (~5 days) in endogenous mRNA IL-10 production are present after a single IT pDNA-Control injection. As determined in the experiment of Example 4.

The Sensitization Period. Macrophage and dendritic cells often respond to pro-inflammatory signaling by releasing anti-inflammatory cytokines like IL-10. In our recent report, we show that accumulation and activation of 'pro-inflammatory-like' (ED1-positive)' innate immune cells within CSF occurs within 6 hr following an initial pDNA-IL-10 injection [120]. We speculate that these cells respond to the stimulatory properties of CpG sequences in naked pDNA that leads to sensitization of the local environment. Hence, we predicted that a first IT pDNA injection not encoding IL-10 (an empty pDNA; pDNA-Control) would lead to a cellular response profile such that: (1) cell enrichment occurs, and (2) enhanced subsequent uptake of the second IT pDNAIL10 would result. If this were true, then long-duration pain reversal should ensue. Indeed, IT pDNA-Control given as an initial Sensitization injection followed by IT pDNA-IL10 leads to the same pain relief profile as two IT pDNA-IL10 injections. Indeed, our pilot data show transient increases (~5 days) in endogenous mRNA IL-10 production are present after a single IT pDNA-Control injection (FIG. 7). IL-10 can itself 'prime' cells in the meninges to augment macrophage & dendritic cell phagocytosis [87, 125, 126]. Importantly, the second injection must contain the IL-10 gene for long-duration IL-10 transgene expression and apin relief. This phenomenon is referred to as the *Sensitization Period*. We propose to examine IL-10 transgene expression in specific cell types and anatomical regions shortly following and long after the Sensitization Period. IL-10 Signaling During Sensitization We have additionally determined that disruption of IL-10 signaling during the Sensitization Period by an IT IL-10 neutralizing antibody (e.g. 24 hrs after the first IT pDNA-Control) leads to a rapid and sustained return of pain despite the second IT pDNA-IL-10 injection [120]. These data suggest active, and ongoing cellular processes during the Sensitization Period impact continuous transgene expression and anti-inflammatory signaling are necessary for enduring duration pain relief ([119]).

Example 5

Ongoing Pain Relief is Due to IL-10 Protein Signaling.

In support that IT pDNA-IL10 is responsible for long duration pain relief by spinal cord IL-10 protein actions, an IT IL-10 neutralizing antibody blocks spinal IL-10 actions 1 month after ongoing pain relief and subsequently returns animals to pain [120]. Control antibodies (IT IgG) did not alter pain relief; rats remained stably reversed from pain ([120]). These data further support that ongoing cellular processes are not only important during the period of sensitization, but also long after. Chemotaxis is a possible mechanism for initial gene delivery & longduration transgene expression. Additional work was conducted to determine whether the sensitization period was initiated in response to plasmid DNA specifically, or to DNA in general. Short synthetic stimulatory DNA sequences (8-12 oligonucleotides; ODN) are characterized to activate TLR-9 on macrophage & dendritic cells [1, 2, 135]. In lieu of pDNA-control, a 1st IT injection of stimulatory sequences TCGTA and TCGA (2 ug) prior to a subsequent pDNA-IL-10 injection was given. A 30-day pain relief profile resulted [120]. Data suggest that ODNs can, to a lesser extent, sensitize the subarachnoid environment, as does pDNA.

Figure 8A:
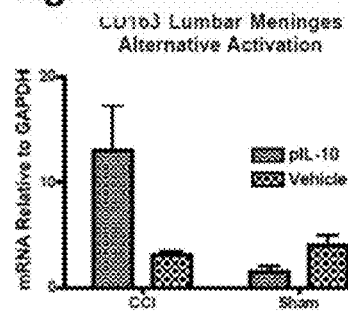
FIG. 8: innate immune cell profiles change in response to IT pDNA-IL-10 in chronic neuropathic (CCI) vs. non-neuropathic rats (Sham). CD163 mRNA, a hallmark surface receptor of the alternative phenotype on macrophage/dendritic cell [115], is strongly upregulated in the lumbar subarachnoid compartment during neuropathic conditions 2 weeks following IT pDNA-IL-10 (FIG. 8A). We also measured robust increases in mRNA levels of macrophage (FIG. 8B) and dendritic (FIG. 8C) cell markers 2 weeks after IT pDNA-IL-10 in behaviorally verified rats. Plasmid-derived mRNA IL-10 production in meninges was simultaneously increased (data not shown). As determined in the experiment of Example 5.
Figure 8B:
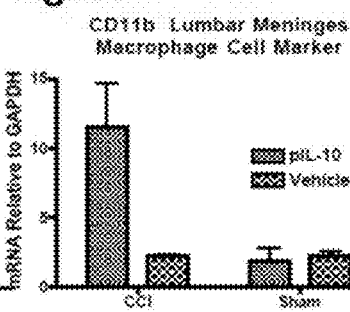
Figure 8C:
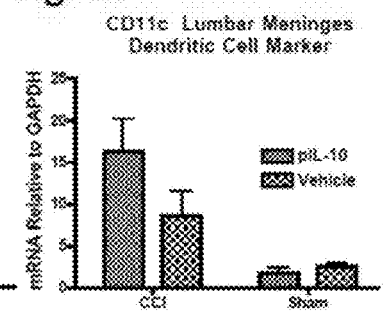

We show that innate immune cell profiles change in response to IT pDNA-IL-10 in chronic neuropathic (CCI) vs. non-neuropathic rats (Sham) (FIG. 8; pilot). CD163 mRNA, a hallmark surface receptor of the alternative phenotype on macrophage/dendritic cell [115], is strongly upregulated in the lumbar subarachnoid compartment during neuropathic conditions 2 weeks following IT pDNA-IL-10 (FIG. 8A). We also measured robust increases in mRNA levels of macrophage (FIG. 8B) and dendritic (FIG. 8C) cell markers 2 weeks after IT pDNA-IL-10 in behaviorally verified rats. Plasmid-derived mRNA IL-10 production in meninges was simultaneously increased (data not shown). TLR-9 activation in monocytes ultimately results in an anti-inflammatory response including the production of IL-10 [30, 75] with decreased production of TNF-α and IL-1 [30, 74]. Whether IT naked pDNA or control alters the cellular phenotypes of innate immune cells during sensitization that is critical for long-duration pain relief & gene expression remains unknown. Related studies are described in the Research Design examine a potential TLR receptor-mediated mechanism for IT immune cell accumulation & sensitization to optimize IL-10 transgene uptake. Our preliminary data reveal pDNA-IL-10 induced increased TLR-9 mRNA production in neuropathic rats measured 2 weeks following IT pDNA-IL-10 (FIG. 9A, pilot). TLR-9 stimulation in premature macrophage and dendritic cells results in the production of a panel of cytokines and chemokines that direct cell recruitment and differentiation [7, 57]. Indeed, we have now measured increased mRNA levels of the chemokine, CCL2, at day 60 after IT pDNA-IL-10 in behaviorally verified animals. These data support that in animals with enduring pain relief who express robust increases in plasmid-derived IL-10 mRNA at day 60, ongoing CCL2 production occurs simultaneously (FIG. 9B, pilot).

Example 6

PLGA Encapsulation of pDNA-IL-10 Improves Spinal Gene Transfer

Figure 10A:
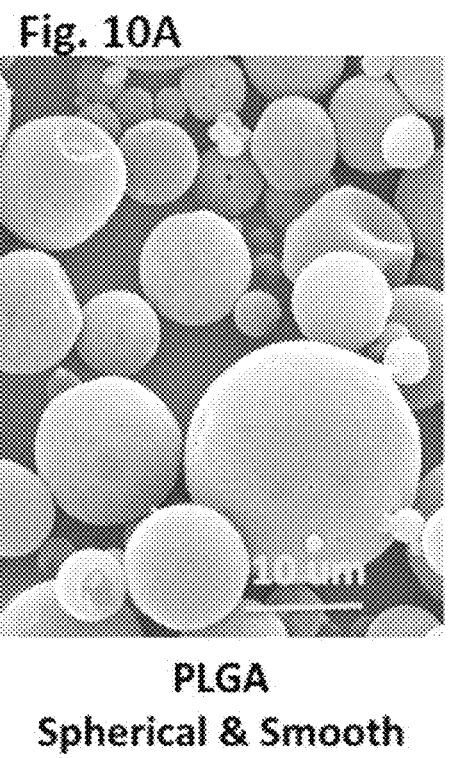
FIG. 10: PLGA is spherical with a smooth surface (FIG. 10A), with a resultant size most frequently observed at ~4.6 um (FIG. 10B). As determined in the experiment of Example 6.
Figure 10B:
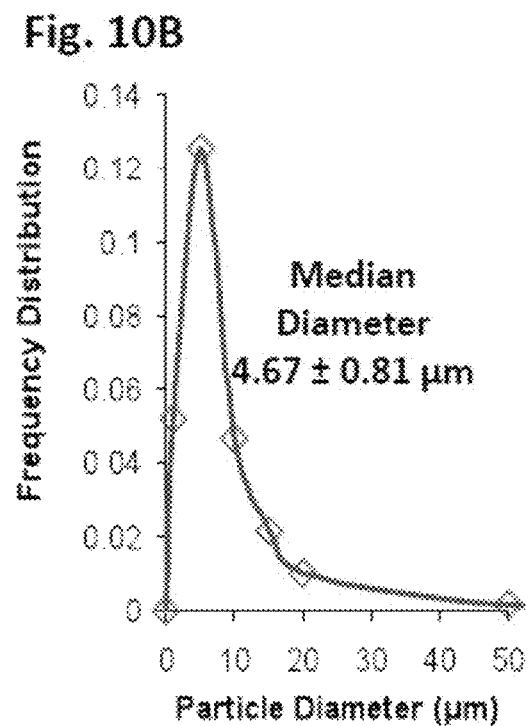

We began to examine methods that might significantly decrease the required pDNA-IL-10 dose, and more importantly, achieve long-duration pain relief upon a single injection. These two goals are critical for clinical utility. The co-polymer, PLGA (50:50), was next examined because it is shown to have a broad safety profile and exploits the function of phagocytosis (<10 um) by innate immune cell for gene transfer [42, 43]. Our preliminary data show that PLGA is spherical with a smooth surface (FIG. 10A), with a resultant size most frequently observed at ~4.6 um (FIG. 10B) ([123], submitted). Additionally, IT PLGA does not lead to elevations in the pro-inflammatory cytokine, interleukin-12 (IL-12) (FIG. 11; pilot), which is often observed with many biodegradable polymers [81]. Phagocytosis-mediated PLGA 'uptake' is particularly attractive for spinal ITpDNA-IL10 gene therapy because of an existing permissive meningeal environment for enhanced IL-10 gene phagocytosis. In collaboration with Dr. Melissa Mahoney (co-Investigator), we have been developing methods to optimize pDNA-IL-10 uptake within the spinal cord for pain relief by microencapsulating pDNA-IL10 within PLGA [95].

Figure 13:
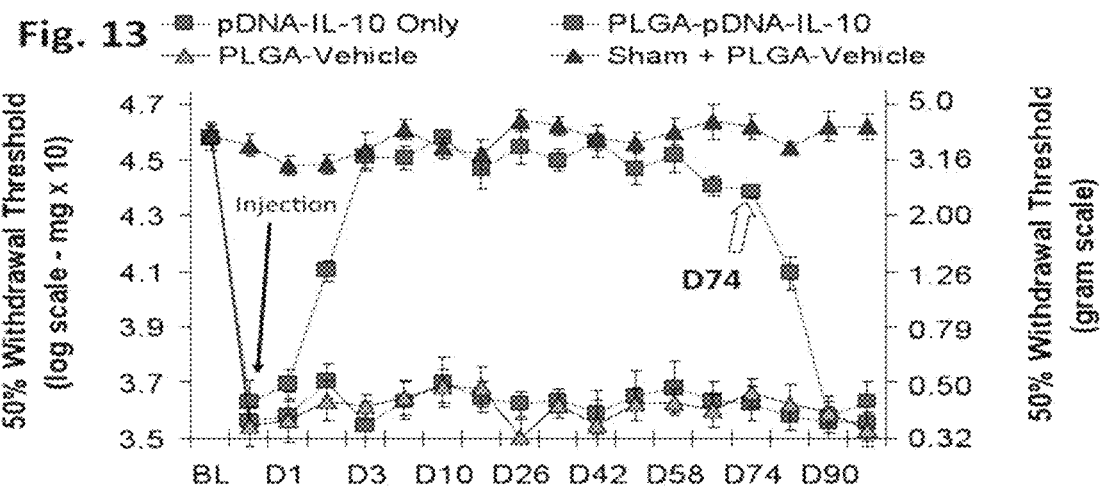
FIG. 13: an IT single injection of 8.7 ug pDNA in 1 mg PLGA (with a 20 ul injection volume) produces full pain relief in neuropathic rats for up to ~74 days thereafter. As determined in the experiment of Example 6.
Figure 14:
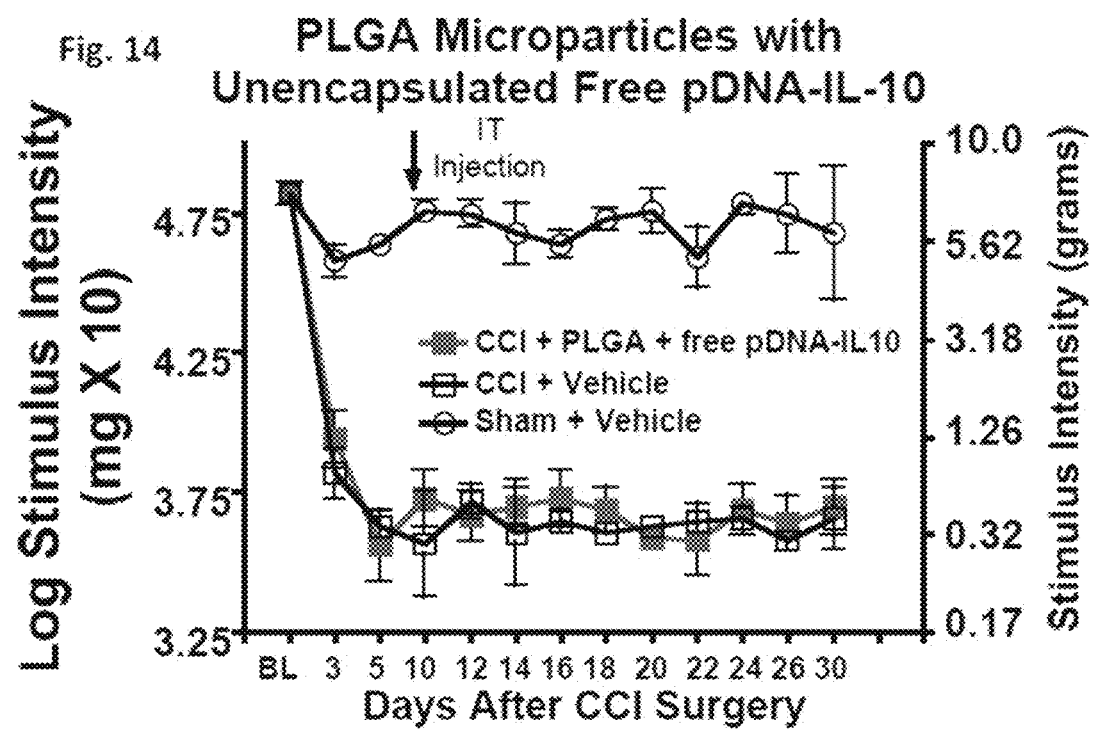
FIG. 14: pDNA must be microencapsulated in PLGA microparticles for pain reversal. As determined in the experiment of Example 6.
Figure 15:
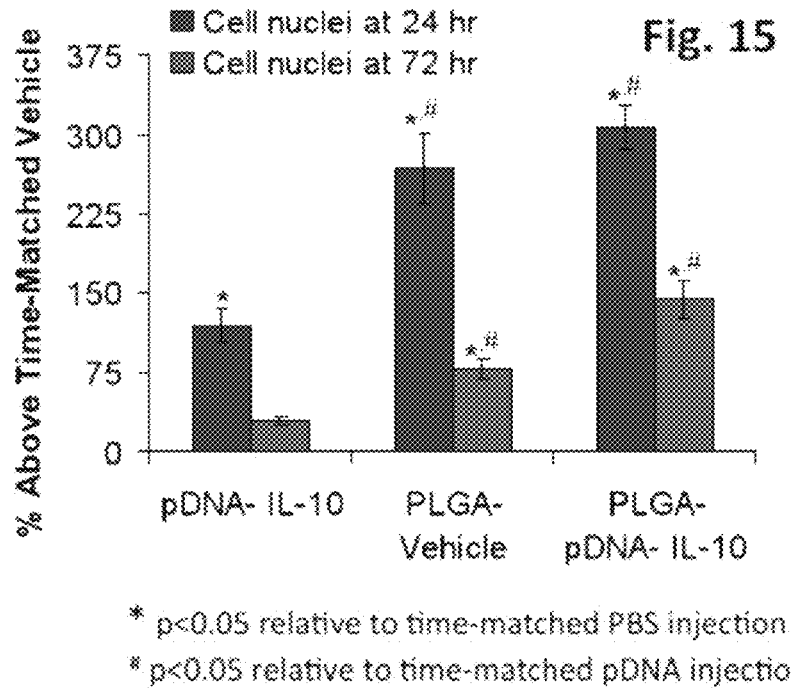
FIG. 15: PLGA initiates macrophage and/or dendritic cell enrichment in the meninges by 24 hr. As determined in the experiment of Example 6.

Using confocal microscopy, we identified PLGA rhodamine-labeled (red) microparticles in close association with accumulated innate immune cell nuclei (DAPI; blue) in the meninges. Additionally, microglial cells identified by staining for Cd11b using the classic OX-42 antibody (FITC) interacts with PLGA in the meninges (FIG. 12A) Immune cells were identified using the classic monocyte/macrophage marker, MHC II (FITC; green) (FIG. 12B) two weeks after the second IT pDNA-IL-10 injection ([123] submitted). Note the large-sized particles (>10 um) embedded in meninges that remain intact for over 2 weeks. This may be particular to PLGA aggregation that occurs in vivo. We have analyzed the PLGA size population in spinal cord meninges from 3-10 days and observed the percentage of smaller-sized particles (<1-5 um) dropped to less than 10% within 24 hr following IT PLGA injection. These observations suggest that larger microparticles are present to release their contents extracellularly at much later time points. We propose to utilize this property of our PLGA formulation to manipulate a decrease in phagocytosis while its cargo is simultaneously slowly released to contact extracellular surface receptors. We have made significant progress since our initial work. We have increased the encapsulation efficiency from 1 ug pDNA-IL-10/mg PLGA to ~8.7 ug pDNA-IL-10/mg PLGA by simply increasing the pDNA-IL-10 concentration (20 mg/ml) prior to encapsulation with PLGA (50:50). A IT single injection of 8.7 ug pDNA in 1 mg PLGA (with a 20 ul injection volume) produces full pain relief in neuropathic rats for up to ~74 days after (FIG. 13, submitted, [123]). We have additionally learned that pDNA must be microencapsulated in PLGA microparticles for pain reversal (FIG. 14, submitted, Soderquist, 2009#855]). At these later time points, the long-duration PLGA pain relief is due to IL-10 spinal signaling because IT neutralizing IL-10 antibody produces a transient return to allodynia submitted, Soderquist, 2009#855]. In addition, PLGA initiates macrophage and/or dendritic cell enrichment in the meninges by 24 hr (FIG. 15). Like that observed following naked IT pDNA-IL-10, we have characterized these cells to undergo a phenotypic shift from the classical (ED1 expression) to alternative (ED2 expression) phenotype (data not shown). Together, these data suggest physiological responses to naked pDNA are similar to those induced by PLGA, which produces a Sensitization Period following IT injection.

Figure 16:
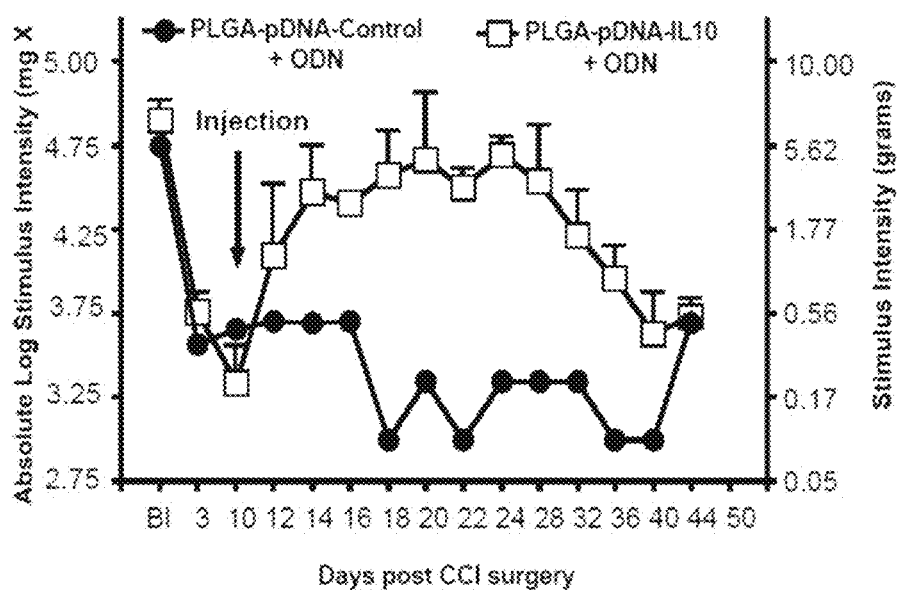
FIG. 16: A single IT injection composed of encapsulated ODNs used to stimulate surrounding macrophage aided PLGA-encapsulated pDNA-IL-10 gene delivery, as measured by a ~30 day pain relief profile. As determined in the experiment of Example 6.

One critical question that stands out is whether PLGA microparticles that encapsulate pDNA-IL-10 can exploit cellular processes that are functionally necessary for IL-10 transgene expression & pain relief. This goal can be achieved by manipulating release rates of pDNA-IL-10 or co-factors from PLGA during and after sensitization. Indeed, our recent pilot data strongly suggest that enhancing TLR-9 activation with a co-delivery of ODN (2 ug) significantly improves the required dose for PLGA-mediated gene transfer to the spinal cord. A single IT injection composed of encapsulated ODNs used to stimulate surrounding macrophage aided PLGA-encapsulated pDNA-IL-10 gene delivery, as measured by a ~30 day pain relief profile (FIG. 16). Therapeutic efficacy of pDNA-IL-10 was achieved with a 10-fold dose improvement; only ~800 ng in 100 ug PLGA was required. This is the first demonstration of non-viral spinal cord IL-10 gene transfer using <1 ug doses that produces significant pain relief. Through a better understanding of the Sensitization Period, we postulate significant improvement of PLGA, as a therapeutic gene delivery device, is feasible, and is a part of our planned studies in this proposal. These data are highly promising as we progress toward a clinical application.

Example 7

Understanding "Sensitization" to Achieve Greater Pain Control.

Figure 17:
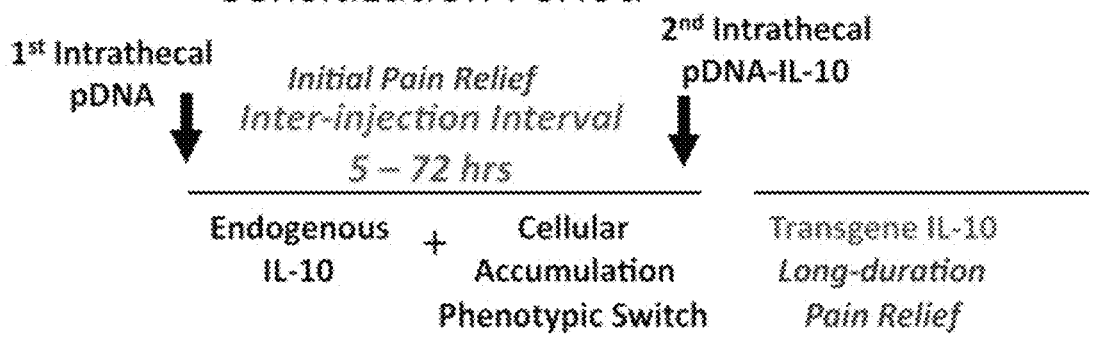
FIG. 17: several novel findings from a gene therapy protocol that established a period of sensitization between 2 sequential, subarachnoid (IT) injections of non-viral plasmid vectors, where the $2^{nd}$ injection must encode the IL-10 gene. As determined in the experiment of Example 7.

Several novel findings from a gene therapy protocol that established a period of sensitization between 2 sequential, subarachnoid (IT) injections of non-viral plamid vectors, where the $2^{nd}$ injection must encode the IL-10 gene (FIG. 17). (A), the initial IT injection of an empty plasmid vector (pDNAControl) 'sensitizes' the subarachnoid site that enables the second, necessary pDNA-IL-10 injection to produce enduring pain relief (3+ months). (B), the sensitization period is discrete (inter-injection intervals; 5 hr to 3 day). (C), a robust accumulation of innate immune cells occurs during the period of sensitization that involves phenotypic changes in these immune cells within this period. IL-10 signaling is necessary during the sensitization period for accumulation of innate immune cells & enduring pain relief that follows the sensitization period. (D), substantial transgenederived IL-10 production is measured in spinal meninges, spinal dorsal horn, and associated DRG for as long as 84 days.

Figure 18:
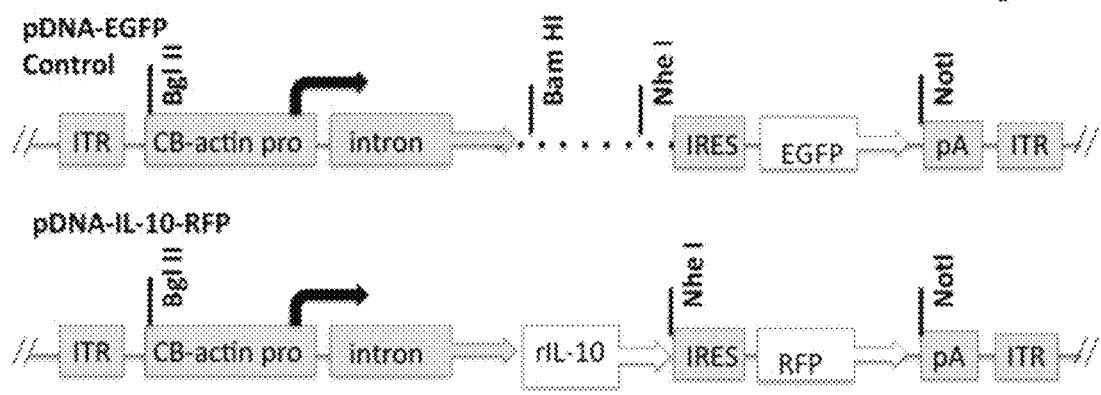
FIG. 18: IRES allows a single promoter to drive the simultaneous production of 2 genes (IL10 and the reporter gene, red fluorescent protein; RFP), yielding predicted stoichiometric expression. The pDNA-Control encodes the reporter gene, enhanced green fluorescent protein (EGFP) and is designated as pDNA-Reporter-Control. As determined in the experiment of Example 7.

To maintain consistency from our prior work with future studies, our current pDNA consists of all the identical properties in addition to an internal ribosomal entry site (IRES) sequence that is routinely applied. IRES allows a single promoter to drive the simultaneous production of 2 genes (IL10 and the reporter gene, red fluorescent protein; RFP), yielding predicted stoichiometric expression. The pDNA-Control encodes the reporter gene, enhanced green fluorescent protein (EGFP) and is designated as pDNA-Reporter-Control (FIG. 18). The plasmid that contains IRES-RFP will also encode rat IL-10 and is designated as pDNA-IL10-RFP. Studies during the current grant period verify that both pDNA-Control-EGFP and pDNA-IL10-RFP induces reporter gene expression & pain relief[120]). For experiments using 2 sequential injections, the established protocol is: 1st IT pDNA-Control-EGFP injection followed by the 2nd IT pDNA-IL10-RFP.

Example 8

PLGA Microparticles

Figure 19:
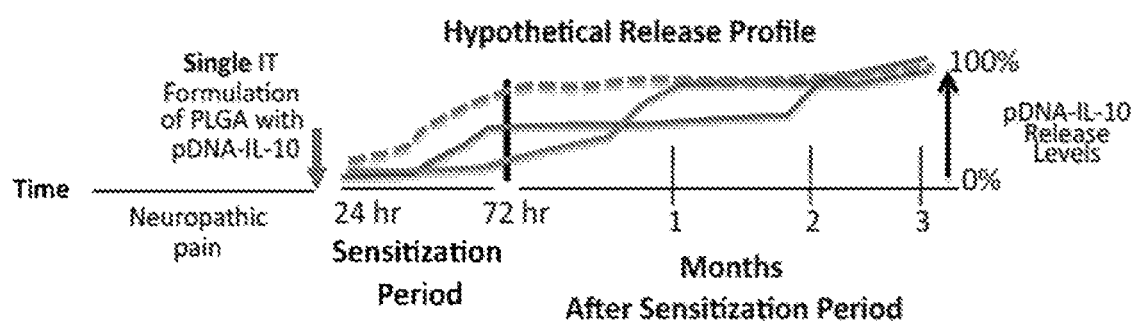
FIG. 19 shows that the current copolymer is prepared with 50:50 PLGA with a number-average molecular weight (MW) of 75,000 (n=0.63), which degrades & releases ~45% its cargo by 72 hr, with the remaining pDNA payload over the course of 60 days. Pain relief following IT PLGA-IL-10 reflects this release profile (FIG. 13).

An advantage of PLGA is its flexibility to control the time-scale over which cargo is released such that full release occurs within or after the sensitization period. That is, we will alter either the ratio of lactic acid to glycolic acid within the PLGA copolymer and/or the molecular weight of PLGA to achieve release 100% of microparticle cargo over a short time-scale (~72 hr), and 1 or 2 months. Our current copolymer is prepared with 50:50 PLGA with a number-average molecular weight (MW) of 75,000 (n=0.63), which degrades & releases ~45% its cargo by 72 hr, with the remaining pDNA payload over the course of 60 days. Pain relief following IT PLGA-IL-10 reflects this release profile (FIG. 13). FIG. 19 illustrates 3 PLGA microparticle formulations to be tested that release cargo with: (1) 100% over 72 hr; dashed blue line, and (2) 100% over 1 month; solid blue line, and (3) 45% cargo release within 72 hr with the remainder by 2 months; red line, current formulation. These time-scales are chosen because (1) significant cell enrichment occurs within 72 hr following an IT naked pDNA injection, (2) cell enrichment and alternative phenotype profiles are observed by 72 hr, and (3) sustained cellular processes may continue long after the sensitization period that produces enduring transgene expression.

Experiment Design. We will develop and test 3 PLGA formulations with time-scale controlled cargo release of: (1) 100% over 72 hr and (2) 100% over 1 month, (3) ~100% over 2 months. By decreasing the molecular weight of the PLGA preparation to 10,000 MW (number ave.=0.17), we can achieve more rapid release (~100% in <72 hr). Further, we expect to be able to achieve 100% release by 1 month by varying the MW of PLGA between 10,000 and 75,000. These 3 copolymers will be used to control the duration of pDNA delivery. FIG. 19, Table IIIA1 summarizes the 3 copolymers to be tested with pDNA-IL-10 and/or co-factor. 'X' in the table represents the intermediate MW that will be empirically determined to release its contents by 1 month. Only a single pDNA-IL-10 loading dose will be used because our prior reports and pilot data show that a min ~10% loading dose is required for therapeutic gene transfer. The dose of co-factor will be determined from Aims I and II. Based on our pilot data, we predict 2 ug of less will be sufficient for each co-factor delivered either naked or PLGA encapsulated.

It is important to note that co-factors, CCL2 and IL-10, bind receptors expressed on the extracellular surface. Cell surface receptors would be most efficiently targeted by encapsulation of PLGA microparticles more than 10-20 um in size because larger microparticles embed in tissue and are not phagocytosed. Our pilot data show 40% of 10-20 urn-sized PLGA microparticles remain intact 2 wk after IT PLGA-IL-10 injection (FIG. 12). Therefore, co-factors intended to target cell-surface receptors will be delivered naked or encapsulated in 10-20 μm-sized microparticles. We will empirically alter the manufacturing steps to identify a protocol that results in larger microparitcles. One possibility is to attempt to gently settle out larger microparitcles by exposing to low speed centrifugation. Another possibility is to control the intensity of duration of vortexing steps during fabrication.

References for Background of the Invention and Examples 1-8

1. Agrawal, S. and E. R. Kandimalla, *Modulation of Toll-like Receptor 9 Responses through SyntheticImmunostimulatory Motifs of DNA*. Ann N Y Acad Sci, 2003. 1002: p. 30-42.
2. Agrawal, S. and E. R. Kandimalla, *Synthetic agonists of Toll-like receptors 7, 8 and 9*. Biochem Soc Trans, 2007. 35(Pt 6): p. 1461-7.
3. Amiji, M. M., *Polymeric Gene Delivery: Principles and Applications*. 2005, Boca Raton: CRC Press.
4. Asensio, V. C. and I. L. Campbell, *Chemokines in the CNS: plurifunctional mediators in diverse states*. Trends in Neuroscience, 1999. 22: p. 504-512.
5. Beletskii, A., et al., *High-throughput phagocytosis assay utilizing a pH-sensitive fluorescent dye*. Biotechniques 2005. 39(6): p. 894-7.
6. Beutler, A. S., et al., *Intrathecal gene transger by adeno-associated virus for pain*. Current Opinion in Molecular therapeutics, 2005. 7(5): p. 431-39.
7. Beutler, B. and H. Wagner, *Toll-Like Receptor Family Members and Their Ligands*. Current Topics in Microbiology and Immunology, ed. R. W. Compans, et al. Vol. 270. 2002, New York: Springer.
8. Brandhonneur, N., et al., *Specific and non-specific phagocytosis of ligand-grafted PLGA microspheres by macrophages*. Eur J Pharm Sci, 2009. 36(4-5): p. 474-485.
9. Braun, J. S., et al., *Cellular components of the immune barrier in the spinal meninges and dorsal root ganglia of the normal rat: immunohistochemical (MHC class II) and electron-microscopic observations*. Cell Tissue Res, 1993. 273: p. 209-217.
10. Bruijns, R. H. and H. Bult, *Effects of local cytochalasin D delivery on smooth muscle cell migration and on collar-induced intimal hyperplasia in the rabbit carotid artery*. Br J Pharmacol, 2001. 134(3): p. 473-83.
11. Buechler, C., et al., *Regulation of scavenger receptor CD163 expression in human monocytes and macrophages by pro-and antiinflammatory stimuli*. J Leukoc Biol, 2000. 67(1): p. 97-103.
12. Busha, D., et al. *Spinal cord gene transfer using naked plasmid DNA coding the anti-inflammatory gene, Interleukin-10 (IL10) leads to long-term reversal of thermal hyperalgesia in chronic constrictioninjury (CCI) rats*. in 25th Annual Scientific Meeting of the American Pain Society. 2006. San Antonio, Tex.: Elsevier.
13. Carter, P. H., et al., *Capped diaminopropionamideglycine dipeptides are inhibitors of CC chemokinereceptor 2 (CCR2)*. Bioorg Med Chem Lett, 2007. 17(19): p. 5455-61.
14. Chacur, M., et al., *Snake venom components enhance pain upon subcutaneous injection: an initialexamination of spinal cord mediators*. Pain, 2004. 111: p. 65-76.
15. Chacur, M., et al., *Snake venom phospholipase A2s (Asp49 and Lys49) induce mechanical allodyniaupon peri-sciatic administration: involvement of spinal cord glia, proinflammatory cytokines and nitricoxide*. Pain, 2004. 108: p. 180-191.

16. Chao, C. C., et al., *Interleukin-1 and tumor necrosis factor-alpha synergistically mediate neurotoxicity: involvement of nitric oxide and N-methyl-D-apartate receptors.* Brain Behav Immunol, 1995. 9: p. 355-365.
17. Chaplan, S. R., et al., *Quantitative assessment of tactile allodynia in the rat paw.* J. Neurosci. Meth., 1994. 53: p. 55-63.
18. Cherney, R. J., et al., *Discovery of trisubstituted cyclohexanes as potent CC chemokine receptor 2 (CCR2) antagonists.* Bioorg Med Chem Lett, 2009. 19(3): p. 597-601.
19. Costigan, M., J. Scholz, and C. J. Woolf, *Neuropathic pain: a maladaptive response of the nervous system to damage.* Annu Rev Neurosci, 2009. 32: p. 1-32.
20. Cotten, M., et al., *Lipopolysaccharide is a frequent contaminant of plasmid DNA preparation and can be toxic to primary human cells in the presence of adenovirus.* Gene Therapy, 1994. 1: p. 239-246.
21. Dansereau, M. A., et al., *Spinal CCL2 pronociceptive action is no longer effective in CCR2 receptor antagonist-treated rats.* J Neurochem, 2008. 106(2): p. 757-69.
22. DeLeo, J. A., L. S. Sorkin, and L. R. Watkins, eds. *Immune and Glial Regulation of Pain.* 2007, IASP Press: Seattle.
23. Diez, S. and C. Tros de Ilarduya, *Versatility of biodegradable poly(D,L-lactic-co-glycolic acid) microspheres for plasmid DNA delivery.* Eur J Pharm Biopharm, 2006. 63(2): p. 188-97.
24. Dougherty, P. M., et al., *Taxol-induced sensory disturbance is characterized by preferential impairment of myelinated fiber function in cancer patients.* Pain, 2004. 109(1-2): p. 132-42.
25. Dromard, C., et al., *Adult human spinal cord harbors neural precursor cells that generate neurons and glial cells in vitro.* J Neurosci Res, 2008. 86(9): p. 1916-26.
26. Dubovy, P., et al., *Increased invasion of ED-1 positive macrophages in both ipsi-and contralateral dorsal root ganglia following unilateral nerve injuries.* Neurosci Lett, 2007. 427(2): p. 88-93.
27. Edelstein, M. L., et al., *Gene therapy clinical trials worldwide: 1989-2004—an overview.* Journal of Gene Medicine, 2004. 6: p. 597-602.
28. Fonnum, F., A. Johnsen, and B. Hassel, *Use of fluorocitrate and fluoroacetate in the study of brain metabolism.* Glia, 1997. 21: p. 106-113.
29. Frieling, T., *[Functional and inflammatory bowel disorders].* Med Klin (Munich), 2006. 101 Suppl 1: p. 139-42.
30. Ghosh, T. K., et al., *Toll-like receptor (TLR) 2-9 agonists-induced cytokines and chemokines: I. Comparison with T cell receptor-induced responses.* Cell Immunol, 2006. 243(1): p. 48-57.
31. Glover, D. J., H. J. Lipps, and D. A. Jans, *Towards safe, non-viral therapeutic gene expression in humans.* Nat Reviews Genetics, 2005. 6: p. 299-310.
32. Gordon, S., *Alternative activation of macrophages.* Nat. Rev., 2003. 3: p. 23-35.
33. Goss, J. R., W. F. Goins, and J. C. Glorioso, *Gene therapy applications for the treatment of neuropathic pain.* Expert Rev. Neurotherapeutics, 2007. 7(5): p. 487-506.
34. Goss, J. R., et al., *Antinociceptive effect of a genomic herpes simplex virus-based vector expressing human proenkephalin in rat dorsal root ganglion.* Gene Ther., 2001. 8: p. 551-556.
35. Gratchev, A., et al., *Alternatively activated antigen-presenting cells: molecular repertoire, immune regulation, and healing.* Skin Pharmacol Appl Skin Physiol, 2001. 14(5): p. 272-9.
36. Hacker, H., et al., *Specificity in Toll-like receptor signalling through distinct effector functions of TRAF3 and TRAF6.* Nature, 2006. 439(7073): p. 204-7.
37. Haghighi, A. B., et al., *CSF levels of cytokines in neuro-Behcet's disease.* Clin Neurol Neurosurg, 2009. 111(6): p. 507-10.
38. Hagihara, Y., et al., *Long-term functional assessment of encapsulated cells transfected with Tet-On system.* Cell Transplant., 1999. 8: p. 431-434.
39. Haines, D. E., H. L. Harkey, and O. al-Mefty, *The "subdural" space: a new look at an outdated concept.* Neurosurgery, 1993. 32(1): p. 111-20.
40. Hassel, B., et al., *Selective inhibition of glial cell metabolism by fluorocitrate.* Brain Res, 1992. 249: p. 120-124.
41. Haydon, P. G., *GLIA: Listening and talking to the synapse.* Nat Rev Neurosci, 2001. 2: p. 185-193.
42. Hedley, M. L., *Formulations containing poly-lactide-co-glycolide) and plasmid DNA expression vectors.* Exper Opin Biol Ther, 2003. 3(6): p. 903-10.
43. Hedley, M. L., *Gene delivery using Poly(lactide-co-glycolide) microspheres,* in *Polymeric Gene Delivery,* M. M. Amiji, Editor. 2005, CRC Press: New York. p. 451-466.
44. Homer, P. J., et al., *Proliferation and differentiation of progenitor cells throughout the intact adult rat spinal cord.* J Neurosci, 2000. 20(6): p. 2218-28.
45. http://www.wiley.co.uk/genetherapy/clinical/. *The Journal of Gene Medicine Clinical Trial site.*
46. Hu, P. and E. M. McLachlan, *Macrophage and lymphocyte invasion of dorsal root ganglia after peripheral nerve lesions in the rat.* Neuroscience, 2002. 112(1): p. 23-38.
47. Hua, X.-Y., et al., *Intrathecal minocycline attenuates peripheral inflammation-induced hyperalgesia by inhibiting p38 MAPK in spinal microglia.* Eur J Neurosci, 2005.22: p. 2431-2440.
48. Huang, D., et al., *The neural chemokine CX3CL1/fractalkine selectively recruits NK cells that modify experimental autoimmune encephalomyelitis within the central nervous system.* FASEB J, 2006. 20: p. 896-905.
49. Huang, L., M.-C. Hung, and E. Wagner, *Nonviral vectors for gene therapy.* 1999, San Diego: Academic Press.
50. Hughes, T. S., et al., *Intrathecal injection of naked plasmid DNA provides long-term expression of secreted proteins.* Mol Ther, 2009. 17(1): p. 88-94.
51. Hughes, T. S., et al., *Immunogenicity of intrathecal plasmid gene delivery: cytokine release and effectson transgene expression.* J Gene Med, 2009. 11(9): p. 782-90.
52. Hutchinson, M. R., et al., *Minocycline supresses morphine-induced respiratory depression, suppresses morphine-induced reward, and enhances systemic morphine-induced analgesia.* Brain Behav Immun, 2008. in press.
53. Jung, H., et al., *Monocyte chemoattractant protein-1 functions as a neuromodulator in dorsal rootganglia neurons.* J Neurochem, 2008. 104(1): p. 254-63.
54. Katakura, T., et al., *CCL17 and IL-10 as effectors that enable alternatively activated macrophages to inhibit the generation of classically activated macrophages.* Journal of Immunology, 2004. 172: p. 1407-1413.
55. Keilhoff, G., et al., *Inhibiting effect of minocycline on the regeneration of peripheral nerves.* Dev. Neurobiol., 2007. 67(10): p. 1382-95.

56. Khalil, I. A., et al., *Uptake pathways and subsequent intracellular trafficking in nonviral gene delivery*. Pharmacol Rev, 2006. 58(1): p. 32-45.
57. Kim, S. Y., et al., *Activation of p38 MAP kinase in the rat dorsal root ganglia and spinal cord following peripheral inflammation and nerve injury*. Neuroreport, 2002. 13(18): p. 2483-6.
58. Kohane, D. S., et al., *Biodegradable polymeric microspheres and nanospheres for drug delivery in the peritoneum*. J Biomed Mater Res, 2006. 77A(2): p. 351-61.
59. Kojima, A. and C. H. Tator, *Epidermal growth factor and fibroblast growth factor 2 cause proliferation of ependymal precursor cells in the adult rat spinal cord in vivo*. Journal Neuropathology and Experimental Neurology, 2000. 59(8): p. 687-697.
60. Kolka, J. A., A. P. Vreede, and B. J. Roessler, *Lipopolysaccharide recognition protein, MD-2, facilitates cellular uptake of E. coli-derived plasmid DNA in synovium*. J Gene Med, 2005. 7(7): p. 956-64.
61. Kolla, V. K., et al., *Association of tumor necrosis factor alpha, interferon gamma and interleukin 10 gene polymorphisms with peripheral neuropathy in South Indian patients with type 2 diabetes*. Cytokine, 2009. 47(3): p. 173-7.
62. Komohara, Y., et al., *Possible involvement of the M2 anti-inflammatory macrophage phenotype in growth of human gliomas*. J Pathol, 2008. 216(1): p. 15-24.
63. Kreutzberg, G. W., *Microglia: a sensor for pathological events in the CNS*. Trends Neurosci., 1996. 19: p. 312-8.
64. Krieg, A. M., *CpG motifs in bacterial DNA and thier immune effects*. Annu. Rev. Immunol., 2002. 20: p. 709-760.
65. Ladeby, R., et al., *Microglial cell population dynamics in the injured adult central nervous system*. Brain Res Brain Res Rev, 2005. 48(2): p. 196-206.
66. Lai, A. Y. and K. G. Todd, *Hypoxia-activated microglial mediators of neuronal survival are differentially regulated by tetracyclines*. Glia, 2006. 53(8): p. 809-16.
67. Lan, Y. Y., et al., *"Alternatively activated" dendritic cells preferentially secrete IL-10, expand Foxp3+CD4+ T cells, and induce long-term organ allograft survival in combination with CTLA4-Ig*, J Immunol, 2006. 177(9): p. 5868-77.
68. Latz, E., et al., *TLR9 signals after translocating from the ER to CpG DNA in the lysosome*. Nature Immunology, 2004. 5: p. 190-198.
69. Lautermilch, N. J. and N. C. Spitzer, *Regulation of calcineurin by growth cone calcium waves controlsneurite extension*. J Neurosci, 2000. 20(1): p. 315-25.
70. Ledeboer, A., et al., *Minocycline attenuates mechanical allodynia and proinflammatory cytokine expression in rat models of pain facilitation*. Pain, 2005. 115: p. 71-83.
71. Ledeboer, A., et al., *Paclitaxel-induced mechanical allodynia in rats is inhibited by spinal delivery of plasmid DNA encoding interleukin-10, in Proceedings of the 11th World Congress on Pain, Progress in Pain Research and Management*, F. H., E. Kalso, and J. O. Dostrovsky, Editors. 2006, IASP Press: Seattle.
72. Ledeboer, A., et al. *Paclitaxel-induced mechanical allodynia in rats is inhibited by spinal delivery of plasmid DNA encoding interleukin-10. in Proceedings of the 11th World Congress on Pain*. 2006. Sydney, Australia: International Association for the Study of Pain.
73. Ledeboer, A., et al., *Regional and temporal expression patterns of interleukin-10, interleukin-10 receptor and adhesion molecules in the rat spinal cord during chronic relapsing EAE*. J. Neuroimmunol., 2003. 136: p. 94-103.
74. Ledeboer, A. M., et al., *Intrathecal interleukin-10 gene therapy attenuates paclitaxel-induced mechanical allodynia and proinflammatory cytokine expression in dorsal root ganglia in rats*. Brain Behavior and Immunity, 2007. 21(5): p. 686-698.
75. Lenert, P., et al., *TLR-9 activation of marginal zone B cells in lupus mice regulates immunity through increased IL-10 production*. J Clin Immunol, 2005. 25(1): p. 29-40.
76. Lenz, F. A., *Neurosurgical treatment of pain, in Handbook of Clinical Neurology; Pain*, F. Cervero and T. S. Jensen, Editors. 2006, *Elsevier B. V*. p. 869-885.
77. Lingnau, M., et al., *Interleukin-10 enhances the CD14-dependent phagocytosis of bacteria and apoptotic cells by human monocytes*. Hum Immunol, 2007. 68(9): p. 730-8.
78. Liu, J., et al., *Electrostatically mediated liposome fusion and lipid exchange with a nanoparticlesupported bilayer for control of surface charge, drug containment, and delivery*. J Am Chem Soc, 2009.131(22): p. 7567-9.
79. Lunsford, L., et al, *Tissue distribution and persistence in mice of plasmid DNA encapsulated in a PLGAbased microsphere delivery vehicle*. J Drug Target, 2000. 8(1): p. 39-50.
80. Madsen, M., et al., *Molecular characterization of the haptoglobin. hemoglobin receptor CD163. Ligandbinding properties of the scavenger receptor cysteine-rich domain region*. J Biol Chem, 2004. 279(49): p. 51561-7.
81. Maheshwari, A., et al., *Biodegradable polymer-based interleukin-12 gene delivery: role of induced cytokines, tumor infiltrating cells and nitric oxide in anti-tumor activity*. Gene Therapy, 2002. 9: p. 1075-1084.
82. Mantovani, A., et al., *Macrophage polarization: tumor-associated macrophages as a paradigm for polarized M2 mononuclear phagocytes*. Trends Immunol, 2002. 23(11): p. 549-55.
83. Martinez, F. O., L. Helming, and S. Gordon, *Alternative activation of macrophages: an immunologic functional perspective*. Annu Rev Immunol, 2009. 27: p. 451-83.
84. Mata, M., S. Hao, and D. J. Fink, *Gene therapy directed at the neuroimmune component of chronic pain with particular attention to the role of TNF alpha*. Neurosci Lett, 2008. 437(3): p. 209-13.
85. McMahon, S. B., W. B. J. Cafferty, and F. Marchand, *Immune and glial cell factors as pain mediators and modulators*. Experimental Neurology, 2005. 192: p. 444-462.
86. McMahon, S. B. and M. Malcangio, *Current challenges in glia-pain biology*. Cell, 2009. 64.
87. McMenamin, P. G., et al., *Macrophages and dendritic cells in the rat meninges and choroid plexus:three-dimentional localisation by environmental scanning electron microscopy and confocalmicroscopy*. Cell Tissue Res, 2003. 313: p. 259-269.
88. Medzhitov, R. and C. A. Janeway, Jr., *Decoding the patterns of self and nonself by the innate immunesystem*. Science, 2002. 296(5566): p. 298-300.
89. Milligan, E. D., et al., *Controlling pathological pain by adenovirally driven spinal production of the anti-inflammatory cytokine, Interleukin-10*. European Journal Neuroscience, 2005. 21: p. 2136-2148.
90. Milligan, E. D., et al., *Thermal hyperalgesia and mechanical allodynia produced by intrathecaladministration of the Human Immunodeficiency Virus-1 (HIV-1) envelope glycoprotein, gp120*. BrainRes., 2000. 861: p. 105-116.
91. Milligan, E. D., et al., *Systemic administration of CNI-1493, a p38 mitogen-activated protein kinaseinhibitor,* blocks intrathecal human immunodeficiency virus-1 gp120-induced enhanced pain states in rats. J Pain, 2001b. 2(6): p. 326-333.
92. Milligan, E. D., et al.; Intrathecal HIV-1 envelope glycoprotein gp120 enhanced pain states mediated by spinal cord proinflammatory cytokines. J Neurosci, 2001a. 21: p. 2808-2819.
93. Milligan, E. D., et al., Controlling neuropathic pain by adeno-associated virus driven production of the anti-inflammatory cytokine, interleukin-10. Molecular Pain, 2005. 1: p. 9-22.
94. Milligan, E. D., et al., Repeated intrathecal injections of plasmid DNA encoding interleukin-10 produce prolonged reversal of neuropathic pain. Pain, 2006. 126: p. 294-308.
95. Milligan, E. D., et al., Intrathecal polymer-based interleukin-10* gene delivery for neuropathic pain. Neuron Glia Biology, 2006. 2: p. 293-308.
96. Milligan, E. D., et al., Spinal glia and proinflammatory cytokines mediate mirror-image neuropathic pain in rats. J Neuroscience, 2003. 23: p. 1026-1040.
97. Milligan, E. D. and L. R. Watkins, Pathological and protective roles of glia in chronic pain. Nat Rev Neurosci, 2009. 10(1): p. 23-36.
98. Milligan, E. D., et al., Evidence that exogenous and endogenous fractalkine can induce spinal nociceptive facilitation in rats. Eur J Neurosci, 2004. 20: p. 2294-2302.
99. Milligan, E. D., et al., An initial investigation of spinal mechanisms underlying pain enhancement induced by fractalkine, a neuronally released chemokine. Eur J Neurosci, 2005. 22: p. 2775-2782.
100. Milligan, E. M., et al., Glially driven enhancement of pain and its control by anti-inflammatory cytokines, in Immune and Glial Regulation of Pain, J. A. De Leo, L. S. Sorkin, and L. R. Watkins, Editors. 2007, ASP Press: Seattle.
101. Mirzadegan, T., et al., Identification of the binding site for a novel class of CCR2b chemokine receptor antagonists: binding to a common chemokine receptor motif within the helical bundle. J Biol Chem, 2000. 275(33): p. 25562-71.
102. Moore, K. W., et al., Interleukin-10 and the interleukin-10 receptor. Annu Rev Immunol, 2001. 19: p. 683-765.
103. Morin, N., et al., Neutrophils invade lumbar dorsal root ganglia after chronic constriction injury of the sciatic nerve. J Neuroimmunol, 2007. 184(1-2): p. 164-71.
104. Muskhelishvili, L., et al., Evaluation of cell proliferation in rat tissues with BrdU, PCNA, Ki-67(MIB-5) immunohistochemistry and in situ hybridization for histone mRNA. J Histochem Cytochem, 2003. 51(12): p. 1681-8.
105. Nutile-McMenemy, N., A. Elfenbein, and J. A. DeLeo, Minocycline decreases in vitro microglial motility, B1-integrin, and Kv1.3 channel expression. J Neurochem, 2007. 10.1111/j.1471-4159.2007.04889.x.
106. Pack, D. W., et al., Design and development of polymers for gene delivey. Nature Rev Drug Discovery, 2005.4: p. 581-593.
107. Papadopoulos, N. G., et al., An improved fluorescence assay for the determination of lymphocyte mediated cytotoxicity using flow cytometry. J Immunol Methods, 1994. 177(1-2): p. 101-11.
108. Paulsen, R. E., et al., An in vivo model for studying function of brain tissue temporarily devoid of glial cell metabolism: the use of fluorocitrate. J Neurochem, 1987. 48(5): p. 1377-85.
109. Planck, S. R., et al., Characterizing extravascular neutrophil migration in vivo in the iris. Inflammation, 2008. 31(2): p. 105-11.
110. Ponomarev, E. D., et al., CNS-derived interleukin-4 is essential for the regulation of autoimmune inflammation and induces a state of alternative activation in microglial cells. J Neurosci, 2007. 27(40): p. 10714-21.
111. Porcheray, F., et al., Macrophage activation switching: an asset for the resolution of inflammation. Clin Exp Immunol, 2005. 142(3): p. 481-9.
112. Ribes, S., et al., Toll-like receptor prestimulation increases phagocytosis of Escherichia coli DH5alpha and Escherichia coli K1 strains by murine microglial cells. Infect Immun, 2009. 77(1): p. 557-64.
113. Rossi, D. and A. Zlotnik, The biology of chemokines and their receptors. Annu Rev Immunol, 2000. 18: p. 217-42.
114. Samad, T. A., et al. Central neuroimmune interactions after peripheral inflammation: interleukin-1b potentiates synaptic transmission in the spinal cord. in Proc Soc Neurosci. 2004.
115. Sarrias, M. R., et al., The Scavenger Receptor Cysteine-Rich (SRCR) domain: an ancient and highly conserved protein module of the innate immune system. Crit Rev Immunol, 2004. 24(1): p. 1-37.
116. Schwach, G., et al., Biodegradable microparticles for sustained release of a new GnRH antagonist-partI: Screening commercial PLGA and formulation technologies. Eur J Pharm Biopharm, 2003. 56(3): p. 327-36.
117. Sendil, D., et al., Antinociceptive effects of hydromorphone, bupivacaine and biphalin released from PLGA polymer after intrathecal implantation in rats. Biomaterials, 2003. 24: p. 1969-1976.
118. Shoskes, D. A., et al., Cytokine polymorphisms in men with chronic prostatitis/chronic pelvic pain syndrome: association with diagnosis and treatment response. J Urol, 2002. 168(1): p. 331-5.
119. Sloane, E., et al., Anti-inflammatory cytokine gene therapy decreases sensory and motor dysfunction in experimental Multiple Sclerosis: MOG-EAE behavioral and anatomical symptom treatment with cytokine gene therapy. Brain Behav Immun, 2009. 23(1): p. 92-100.
120. Sloane, E. M., et al., Immunological priming potentiates non-viral anti-inflammatory gene therapy treatment of neuropathic pain. Gene Therapy, 2009(1): p. 1-13.
121. Sloane, E. M., et al., Long term control of neuropathic pain in a non-viral gene therapy paradigm. Gene Therapy, 2009. 16(4): p. 470-5.
122. Sloane, E. M., et al., Long-term control of neuropathic pain in a non-viral gene therapy paradigm. GeneTher, 2009. 16(4): p. 470-5.
123. Soderquist, R. G., et al., Release of plasmid DNA encoding IL-10 from PLGA microparticles facilitates long-term reversal of neuropathic pain following a single intrathecal administration. J Controlled Release, 2009. submitted.
124. Soderquist, R. G., et al. Sustained resolution of neuropathic pain following microparticle-mediated intrathecal delivery of anti-inflammatory interleukin-10 plasmid DNA. in Rocky Mountain Regional Neuroscience 2008. Fort Collins.
125. Spittler, A., et al., Immunomodulatory effects of glycine on LPS-treated monocytes: reduced TNF-alpha production and accelerated IL-10 expression. FASEB J, 1999. 13(3): p. 563-71.
126. Spittler, A., et al., IL-10 augments CD23 expression on U937 cells and down-regulates IL-4-driven CD23 expression on cultured human blood monocytes: effects of IL-10 and other cytokines on cellphenotype and phagocytosis. Immunology, 1995. 85(2): p. 311-7.

127. Stevens, S. L., et al., *Toll-like receptor 9: a new target of ischemic preconditioning in the brain.* J Cereb Blood Flow Metab, 2008. 28(5): p. 1040-7.

128. Sulahian, T. H., et al., *Human monocytes express CD163, which is upregulated by IL-10 and identical to p155.* Cytokine, 2000. 12(9): p. 1312-21.

129. Sweitzer, S. M., et al., *Focal peripheral nerve injury induces leukocyte trafficking into the central nervous system: potential relationship to neuropathic pain.* Pain, 2002. 100: p. 163-170.

130. Tikka, T. M. and J. E. Koistinaho, *Minocycline provides neuroprotection against N-methyl-D-aspartate neurotoxicity by inhibiting microglia.* J Immunology, 2001. 166: p. 7527-7533.

131. Tsai, E. C., et al., *A novel method for simultaneous anterograde and retrograde labeling of spinal cordmotor tracts in the same animal.* J Histochemistry & Cytochemistry, 2001. 49(9): p. 1111-21.

132. Uceyler, N., et al., *Reduced levels of antiinflammatory cytokines in patients with chronic widespread pain.* Arthritis and Rheumatism, 2006. 54: p. 2656-2664.

133. Vandenabeele, F., J. Creemers, and I. Lambrichts, *Ultra structure of the human spinal arachnoid mater and dura mater.* J Anat, 1996. 189 (Pt 2): p. 417-30.

134. Vollmer, J., et al., *Impact of modifications of heterocyclic bases in CpG dinucleotides on their immune modulatory activity.* J Leukoc Biol, 2004. 76(3): p. 585-93.

135. Wagner, H., *The immunobiology of the TLR9 subfamily.* Trends Immunol, 2004. 25(7): p. 381-6.

136. Wang, D., et al., *Oligodeoxyribonucleotide-based antagonists for Toll-like receptors 7 and 9.* J Med Chem, 2009. 52(2): p. 551-8.

137. Wang, Y., et al., *The Toll-like receptor 7 (TLR7) agonist, imiquimod, and the TLR9 agonist, CpG ODN, induce antiviral cytokines and chemokines but do not prevent vaginal transmission of simian immunodeficiency virus when applied intravaginally to rhesus macaques.* J Virol, 2005. 79(22): p. 14355-70.

138. Watkins, L. R. and S. F. Maier, Glia: *A novel drug discovery target for clinical pain.* Nat Rev Drug Discov, 2003. 2: p. 973-985.

139. Watkins, L. R., E. D. Milligan, and S. F. Maier, *Spinal cord glia: new players in pain.* Pain, 2001. 93: p. 201-205.

140. Watson, J. D., *Molecular Biology of the Gene.* 4th ed. 1997, Menlo Park, Calif.: Benjamin/Cummings.

141. White, F. A., S. K. bhangoo, and R. D. Miller, *Chemokines: Integrators of pain and inflammation.* Nature Rev, 2005. 4: p. 834-844.

142. White, F. A., H. Jung, and R. J. Miller, *Chemokines and the pathophysiology of neuropathic pain.* Proc Natl Acad Sci USA, 2007. 104(51): p. 20151-8.

143. White, F. A., et al., *Excitatory monocyte chemoattractant protein-1 signaling is up-regulated in sensory neurons after chronic compression of the dorsal root ganglion.* Proc Natl Acad Sci USA, 2005. 102(39): p. 14092-7.

144. Wicks, I. P., et al., *Bacterial Lipopolysaccharide copurifies with plasmid DNA: implications for animal models and human gene therapy.* Human Gene Therapy, 1995. 6: p. 317-323.

145. Willis, W. D. J., *Hyperalgesia and Allodynia.* Hyperalgesia and Allodynia, ed. W. Willis. 1992, New York: Raven Press.

146. Yew, N. S. and S. H. Cheng, *Reducing the immunostimulatory activity of CpG-containing plasmid DNA vectors for non-viral gene therapy.* Expert Opin Drug Deliv, 2004. 1(1): p. 115-25.

147. Yi, A.-K., et al., *Role of mitogen-activated protein kinases in CpG DNA-mediated IL-10 and IL-12 production: Central role of extracellular signal-regulated kinase in the negative feedback loop of the CpG DNA-mediated Th1 response.* J Immunol, 2002. 168: p. 4711-20.

148. Zhang, J., et al., *Expression of CCR2 in both resident and bone marrow-derived microglia plays a critical role in neuropathic pain.* J Neurosci, 2007. 27(45): p. 12396-406.

149. Zhang, R. X., et al., *Spinal glial activation in a new rat model of bone cancer pain produced by prostate cancer cell inoculation of the tibia.* Pain, 2005. 118: p. 125-136.

150. Zhao, H., et al., *Contribution of Toll-like receptor9 signaling to the acute inflammatory response to nonviral vectors.* Mol Ther, 2004. 9(2): p. 241-8.

Example 9

The Effect of NorBIRT on RAW 264.7Macrophage Cells

As explained above, using NorBIRT and DANBIRT to treat chronic neuropathic pain is an entirely novel therapeutic approach. In the experiments of this example, we explored various processes implicated by such therapeutic efficacy.

Figure 20:
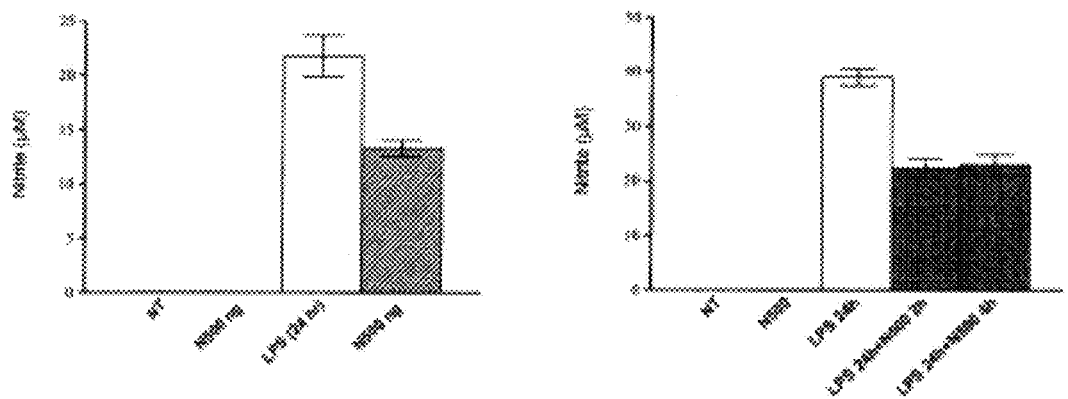
FIG. 20: NorBIRT inhibits LPS-induced NO production in RAW 264.7 macrophage cells. As determined in the experiment of Example 9.

The ability of NorBIRT to inhibit LPS-induced NO production in RAW 264.7macrophage cells was tested. Cells were pre-treated with NorBIRT (500 ng/ml) for 1, 2, and 4 h then exposed to LPS (500 ng/ml) for 24 h. As shown in FIG. 20, NorBIRT inhibits LPS-induced NO production in RAW 264.7macrophage cells.

Figure 21:
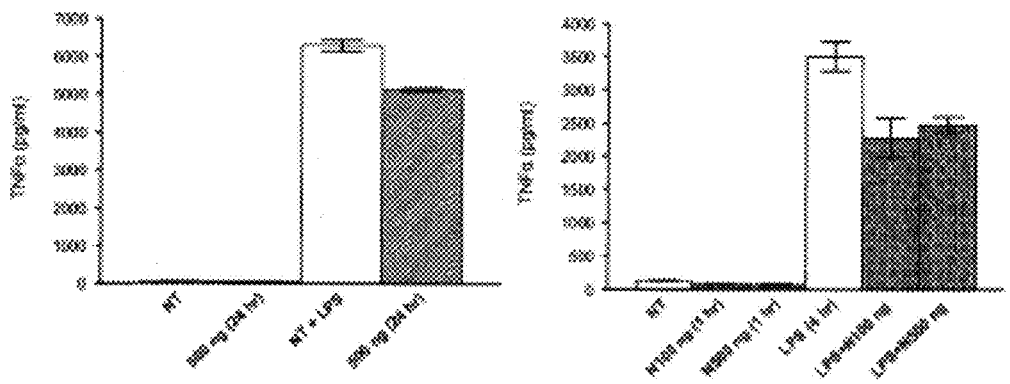
FIG. 21: NorBIRT attenuates expression of the pro-inflammatory cytokine TNF-α in LPS simulated RAW 264.7 cells. As determined in the experiment of Example 9.

As shown in FIG. 21, NorBIRT attenuates expression of the pro-inflammatory cytokine TNF-α in LPS simulated RAW 264.7 cells. In this experiment, cells were incubated with NorBIRT (500 ng/ml; 1 h) and after treatment with LPS (500 ng/ml; 4 and 24 h) the protein levels of TNF-α was evaluated by ELISA.

Figure 22:
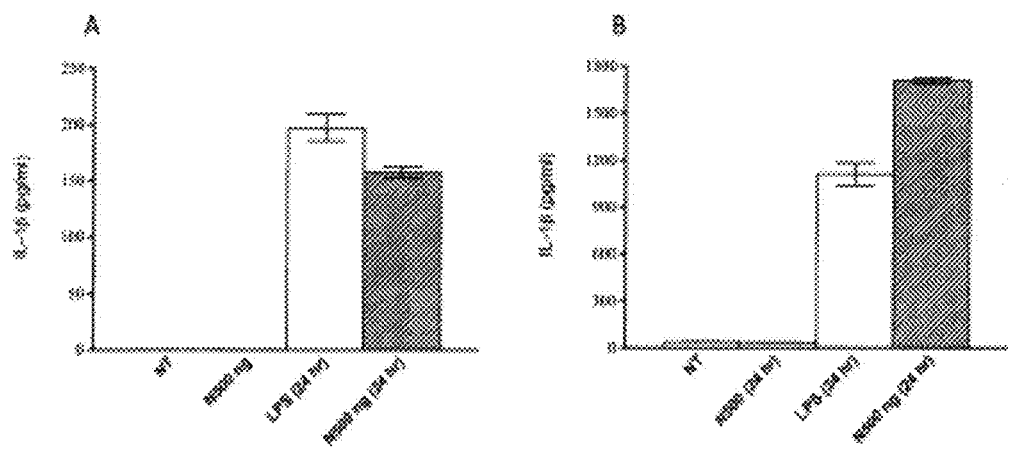
FIG. 22: NorBIRT inhibits LPS-stimulated expression of IL-1β in RAW 264.7 cells. As determined in the experiment of Example 9.

Additionally, RAW 264.7 cells were pretreated with 500 ng/ml of NorBIRT and were stimulated with LPS (500 ng/ml). The levels of IL-1β were measured by ELISA, (A) supernatants and (B) celllysates. While IL-1β release is reduced, intracellular IL-1β I increased, which suggests the pro-active form of IL-1β is not cleaved to its mature, active form for release. FIG. 22 illustrates that NorBIRT inhibits LPS-stimulated expression of IL-1β in RAW 264.7 cells.

Figure 23:
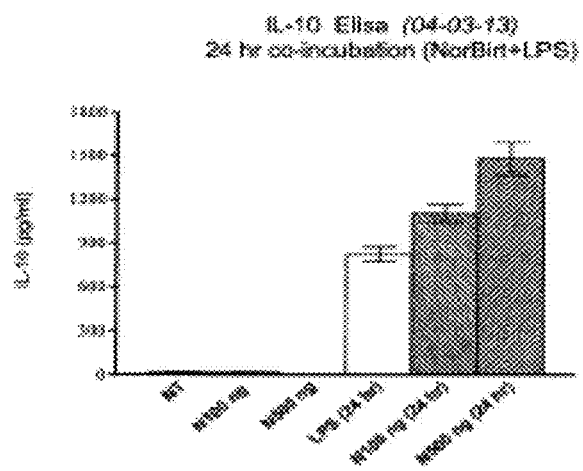
FIG. 23: NorBIRT increases the IL-10 production in LPS-stimulated macrophage RAW 264.7 cells. As determined in the experiment of Example 9.

We also determined that co-incubation with NorBIRT and LPS (500 ng/ml) resulted in increased levels of Il-10, as shown in FIG. 23. Protein levels of Il-10 were evaluated using ELISA.

Figure 24:
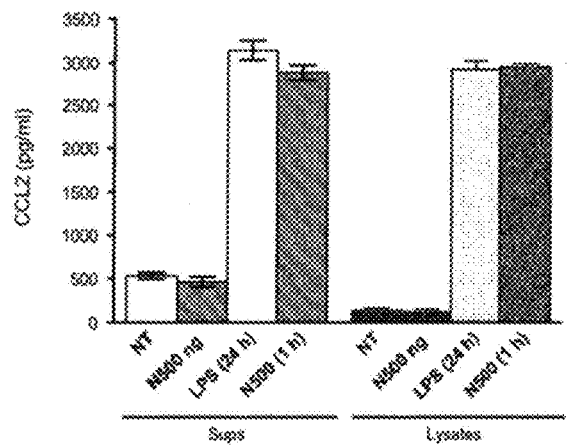
FIG. 24: NorBIRT does not inhibit LPS-stimulated CCL2 production in RAW 264.7 cells. As determined in the experiment of Example 9.

RAW 264.7 cells were also pretreated with NorBIRT (500 ng/ml) for 1 h before being incubated with LPS (500 ng/ml) for 24 h. The culture supernatant was analyzed for CCL2 production in both, supernatants and celllysates. As illustrated in FIG. 24, it was determined that NorBIRT does not inhibit LPS-stimulated CCL2 production in RAW 264.7 cells.

Figure 25:
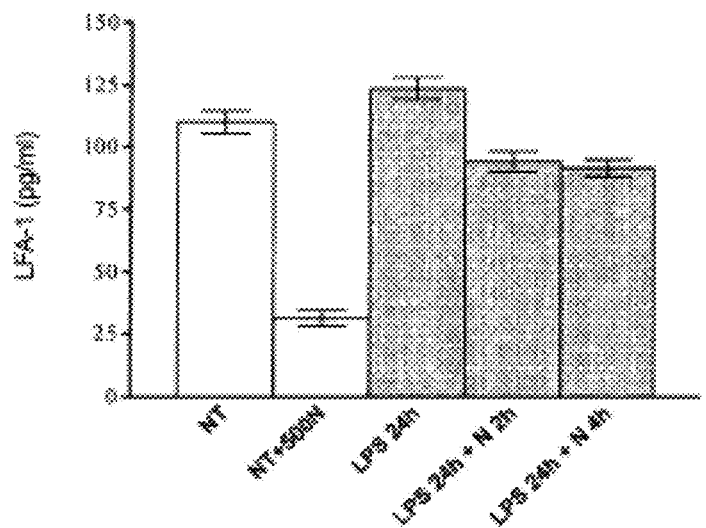
FIG. 25: NorBIRT inhibits LPS-stimulated LFA-1 protein expression in RAW 264.7 cells. As determined in the experiment of Example 9.

Further, RAW 264.7 cells were pretreated with NorBIRT (500 ng/ml) for 2 and 4 h before being incubated with LPS (500 ng/ml). After 24 h of incubation, LFA-1 was measured in celllysates by ELISA. We found that NorBIRT inhibits LPS-stimulated LFA-1 protein expression in RAW 264.7 cells, as indicated in FIG. 25.

Figure 26:
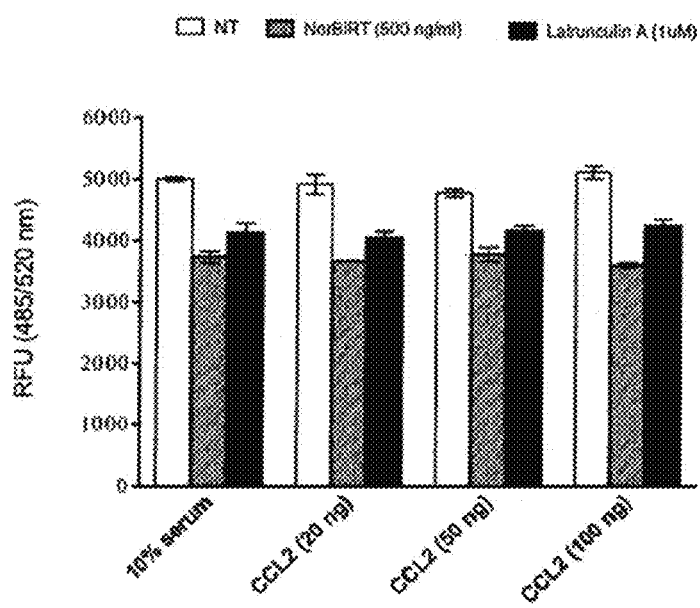
FIG. 26: NorBIRT inhibits mouse macrophage cell migration. As determined in the experiment of Example 9.

Mouse macrophages cell migration in response to CCL2 was assessed with recombinant mouse CCL2 (2D-100 ng/ml) in RAW 264.7 cells. Latrunculin was used as a positive control to inhibit cell migration. As shown in FIG. 26, NorBIRT was found to inhibit mouse macrophage cell migration.

Figure 27:
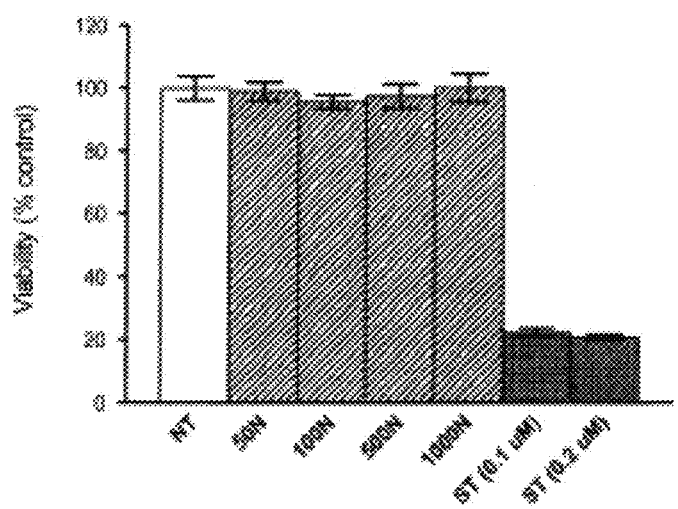
FIG. 27: NorBIRT does not affect the viability of RAW 264.7 cells. As determined in the experiment of Example 9.
Figure 29:
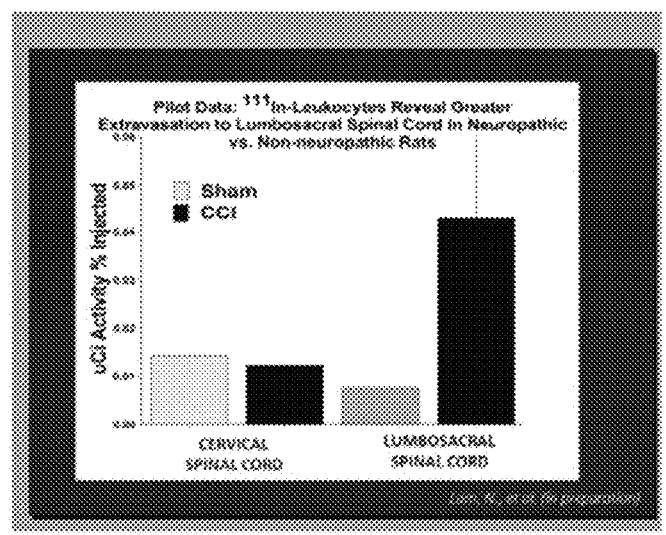
FIG. 29: $^{111}$In lueokocytes reveal greater extravasation, as determined in the experiments of Example 10.
Figure 30:
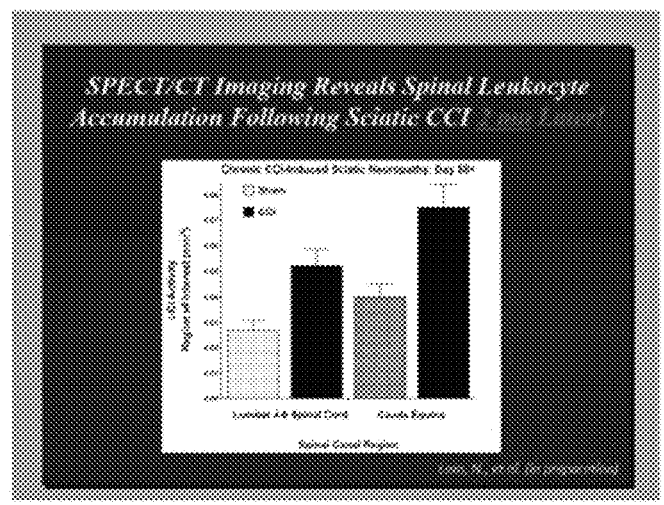
FIG. 30: SPECT/CT imaging reveals spinal leukocyte accumulation two months after sciatic CCI. As determined in the experiments of Example 10.

RAW 264.7 cells were treated with NorBIRT for the indicated concentrations (50, 100, SOO, and 1000 ng/ml) for 24 h. Cytotoxicity was analyzed using an WST-1 assay. The WST-1 conversion assay was based on the mitochondrial function of intact cells. It was determined that NorBIRT does not affect the viability of RAW 264.7 cells, as shown by FIG. 27.

Example 10

LFA-1 is a Therapeutic Target for Sustained Pain Control

The experimental results described in this example demonstrate that glial activation and associated proinflammatory cytokine actions, and possibly actions resulting from spinal leukocyte accumulation, drive peripheral neuropathic pain. Under conditions that lead to pathological pain, the glia are triggered, proinflammatory cytokine and chemokine actions result, and signaling to b-integrins occurs producing leukocyte accumulation. However, the actions of b-integrins themselves, like LFA-1, may be significant contributors to enduring pain outcomes, as targeting LFA-1 activation suppresses leukocyte accumulation, proinflammatory cytokine secretion, and ongoing pain. Intriguingly, we show that blocking LFA-1 increases IL-10 secretion. Thus, these data suggest that LFA-1 may be a new therapeutic target for sustained pain control.

Initially, we determined that peripheral leukocytes accumulate in spinal regions that are necessary for pain signaling. We used a small animal SPECT/CT imaging system (single-photon emission computerized tomography) which was very similar to PET imaging, but which had better resolution. We found that if we blocked the actions of factors expressed on the surface of leukocytes that increase their 'stickiness' (which helps them migrate into specific tissue regions), we robustly controlled neuropathic pain, with concurrent diminished spinal leukocyte accumulation. Blocking spinal leukocyte accumulation may be a novel therapeutic target promising for future clinical applications.

Activated glia release a whole family of proinflammatory cytokines—namely TNF, IL1, and chemokines. Neurons as well as glia express receptors for many of these. Pain transmission neurons are exposed to PICs leading to their activation. And PIC actions are able to create ongoing pain changes because each family member stimulates the release of all the others.

The animal models used in the experiments of this example extend to the well characterized & widely used model of peripheral neuropathy—sciatic nerve chronic constriction injury which combines both direct trauma plus inflammation to the sciatic nerve. When the peripheral nerves become unhealthy, neuropathic pain often ensues. This model combines both inflammation from loosely tied chromic gut ligatures that leads to a localized inflammation followed by slight constriction. In this model, spinal cord glia are activated, PICs are produced and blocking the actions of glia & PICs prevents and reverses neuropathic pain.

Figure 34:
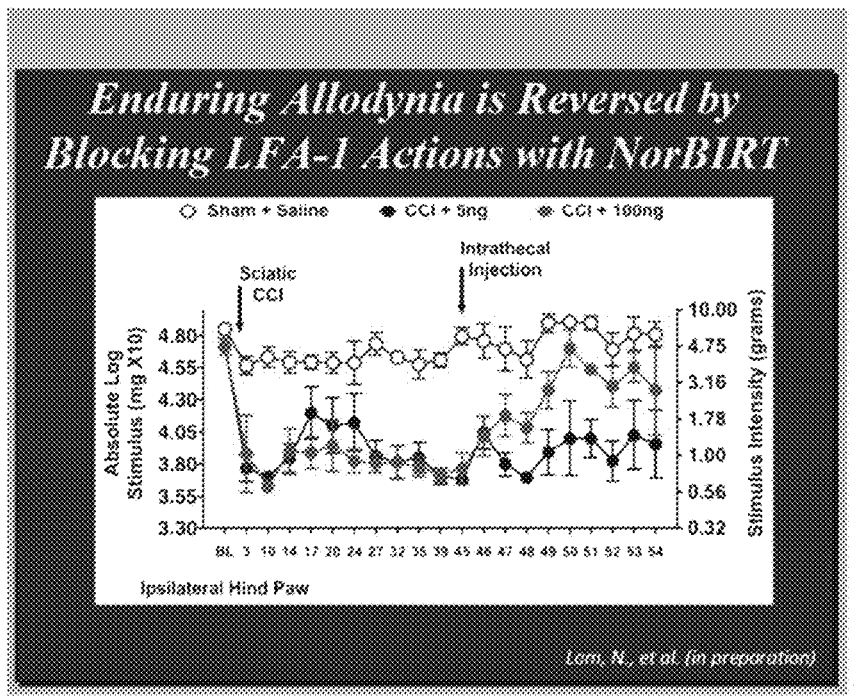
FIG. 34: Enduring allodynia is reversed by blocking LFA-1 actions with NorBIRT. As determined in the experiments of Example 10.

As shown in FIG. 34, hindpaw withdrawal responses to calibrated light touch pressure applied to the hindpaws. This stimulus elicits a paw withdrawal response. Under normal conditions, rats respond to about 10 g of pressure. However, under pathological conditions—when pain is amplified, rats will respond to less than 1 g of pressure. This increased sensitivity to light touch is referred to as allodynia. Clinically, allodynia is a very serious problem for chronic pain patients because even clothing on their skin is coded as very painful.

Figure 35:
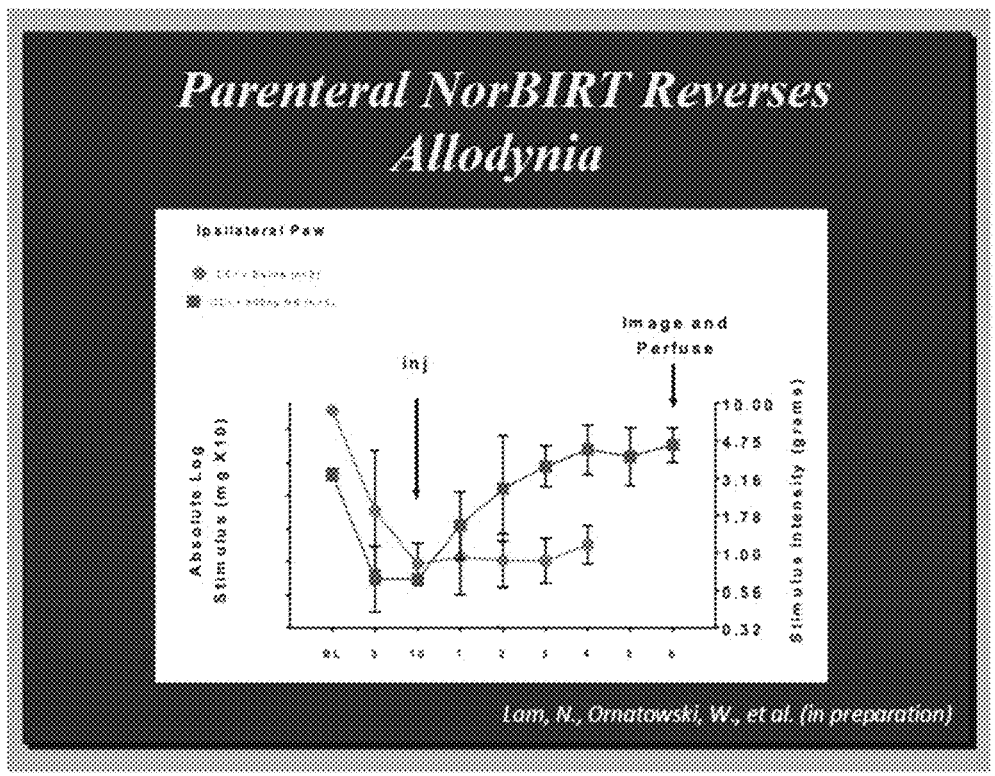
FIG. 35: Parenteral NorBIRT reverses allodynia, as determined in the experiments of Example 10.

In FIG. 35, the y-axis represents stimulus intensity, in grams, and the X-axis represents time. At baseline, rats respond normally, at ~10 grams. (A) after sciatic nerve injury from CCI, a clear allodynia develops, as measured 3 and 10 days later. Rats now respond to <1 gram of touch-pressure. (B) In rats given a control intrathecal injection, that is an injection into the subarachnoid matrix and cerebrospinal fluid surrounding the spinal cord, this intrathecal vehicle injection does alter ongoing allodynia—it remains stable and unchanged. In contrast, as shown in red, (C) blocking the spinal cord actions of IL1 with IL-1 receptor antagonist completely abolishes allodynia, with allodynia returning by 24 hr in keeping with the short half-life of this drug. Importantly, if this same experiment was conducted 2 months later, and IL1 actions were blocked in the spinal cord, the identical profile would emerge. This suggests that proinflammatory cytokines are critically important in the maintenance of neuropathic pain, as well as in its initiation.

We next investigated whether peripheral immune cells in addition to spinal glia could participate in ongoing pain changes. First, it was determined whether leukocytes could extravasate into the lumbosacral region during ongoing neuropathy. Peritoneal leukocytes from same-strain donor rats were collected and labeled with a gamma-emitting radio-isotope INDIUM-11 and injected i.v. into either CCI or sham treated rats. Biodistributions were examined using a small animal SPECT/.

While the radiolabeled leukocytes migrated to other filtering organs, we observed a clear and robust accumulation of leukocytes to the lumbosacral spinal region in CCI neuropathic rats. The left panel of FIG. 27 is a SPECT/CT image of a whole rat with unilateral sciatic nerved with clear allodynia. We see clear signal emerging from the lumbosacral spinal region because leukocytes have accumulated there. The top right panel is a cross section of the lumbosacral region from a sham-treated non-neuropathic rat that was also injected with Indium-labeled leukocytes. The bottom panel is a cross-section of the lumbar region shown in the left panel. Importantly, free indium—not with cells-reveals no accumulation in any region at the time of imaging. This scale showing yellow (lightened) indicates greater isotope signal—pink, moderate and deep violet is virtually background. Much greater leukocyte accumulation is present in the spinal canal in this neuropathic rat compared to the sham rat.

We quantified radioactivity—in uCis—in very discrete spinal regions of interest related to incoming sciatic pain information. We determined discrete differences in the levels of uCi activity within specific Lumbar vertebra and from the underlying L4-L6 spinal canal, even the associated intervertebral disc regions. We analyzed the L4-L6 spinal canal The images of FIG. 28 were captured under physiological conditions, day 10 of CCI. We compared lumbar vs. the C2-C4 cervical spinal regions. Here, the Y-axis indicates magnitude of radioisotope activity in uCi. We observed that, compared to sham-control-treated rats, leukocyte accumulation is dramatically increased specifically in the lumbosacral spinal canal region of neuropathic rats, but not in the cervical region. This pattern is logical because incoming pain signaling in this model occurs at the lumbar spinal level, and not at the cervical level.

We next examined whether leukocyte accumulation is present following enduring neuropathy, not only in the early phases od developing neuropathy. Upon SPECT/CT imaging of rats following their standard i.v. leukocyte-Induimu injection, 2 months later—and compared to sham-operated control rats, we again observed a clearly robust profile of leukocyte accumulation. This observation indicated that there is an active, ongoing neuro-immune process that could contribute to enduring neuropathic pain.

The underlying mechanism for the observed leukocyte accumulation was next considered. The β2-integrin family. β2-integrins—in a conformational state—are directly involved in adhesion of leukocytes that interact with specific adhesion molecules expressed on blood vessel walls and ultimately leads to transendothelial migration into tissue parenchyma. If β2-integrins play a role, their increased expression in lumbar tissue of neuropathic rats should be observable.

Figure 31:
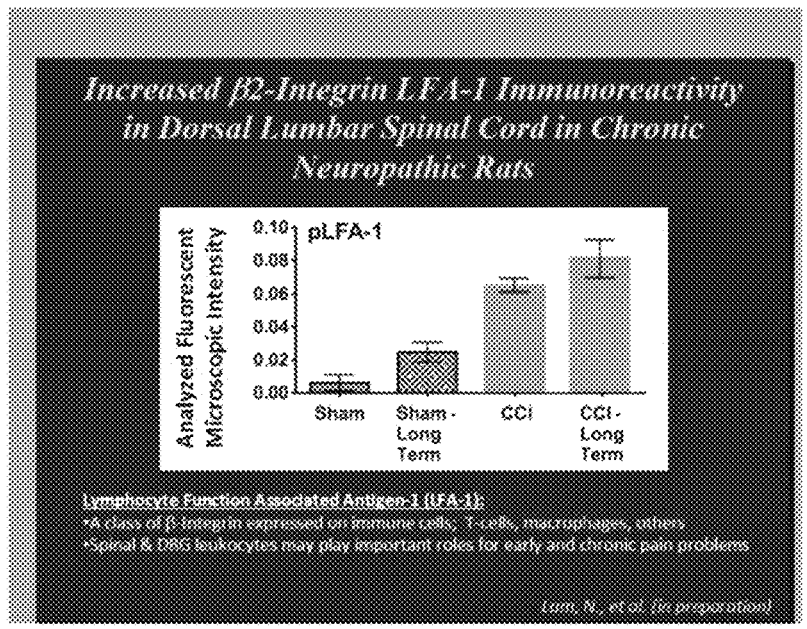
FIG. 31: Increased b2-integrin LFA-1 immunoreactivity in dorsal lumbar spinal cord in chronic neuropathic rats. As determined in the experiments of Example 10.

We examined the specific β2-integrin, lymphocyte function-associated antigen-1 (LFA-1) under the microscope in the dorsal spinal cord region by staining for the activated conformational states of LFA-1 using standard immunefluorescent techniques. We then quantitatively analyzed fluorescent intensity. In FIG. 31, the Y-axis represents fluorescence intensity. The data demonstrate that compared to non-neuropathic controls, rats with short and long-duration CCI neuropathy show significantly greater activated LFA-1 expression in the dorsal horn spinal cord. These data suggest that LFA-1 may be involved in spinal leukocyte accumulation in early and chronic pain problems.

Figure 32:
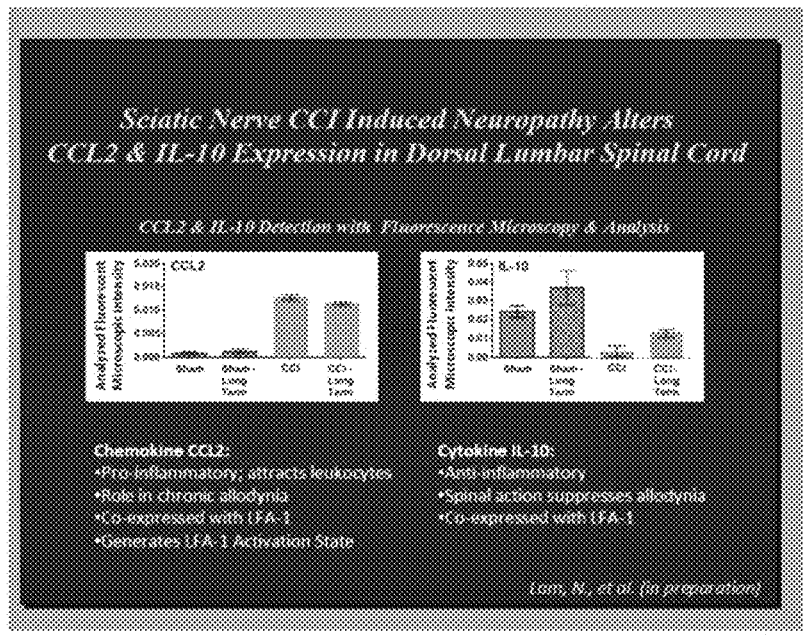
FIG. 32: Sciatic nerve CCI induced neuropathy alters CCL2 & IL-10 expression in dorsal lumbar spinal cord. As determined in the experiments of Example 10.
Figure 33:
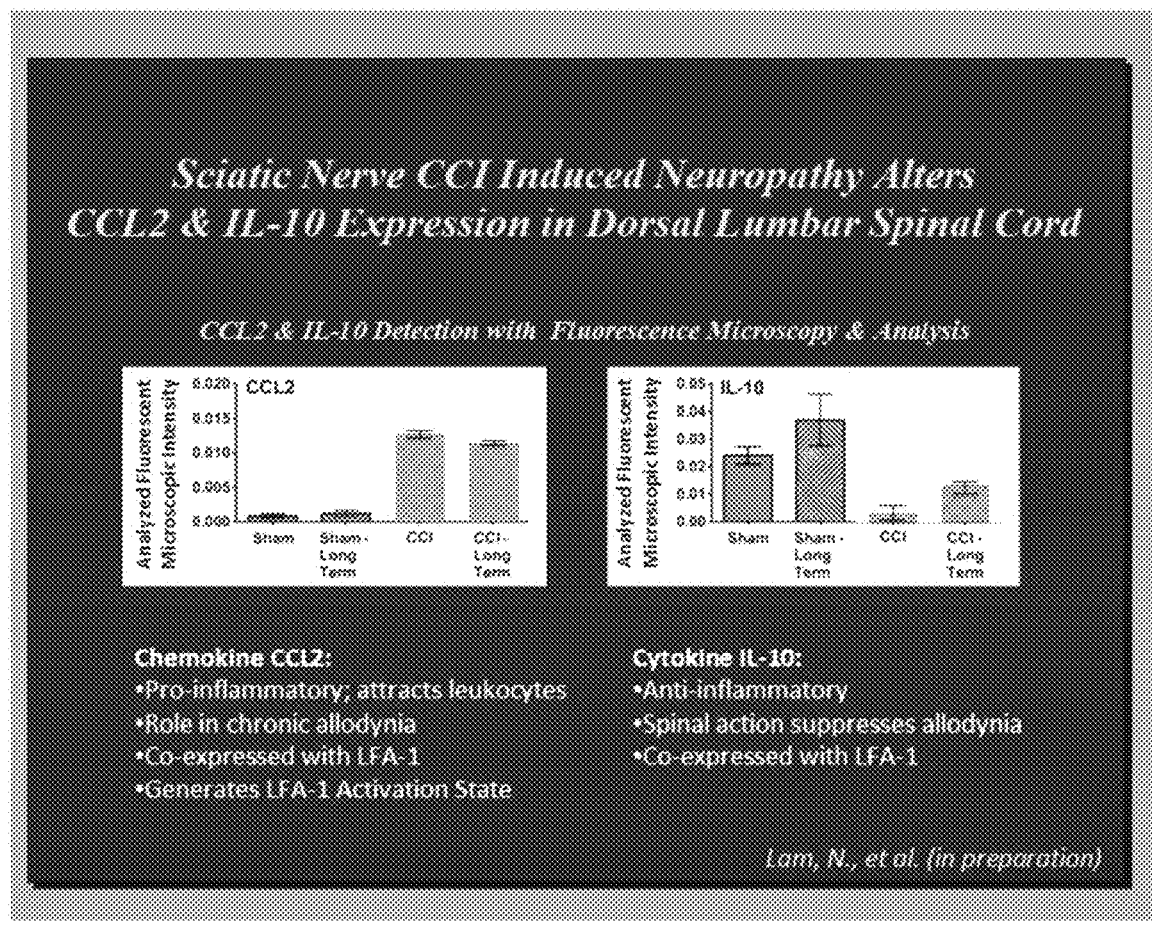
FIG. 33: Allodynia is substantially reversed after spinal blockade of LFA-1, as determined in the experiments of Example 10.

We considered whether CCL2 induces the conformational activation state of LFA-1 via its CCR2 receptor coexpressed on cells with LFA-1. Under immunofluorescent microscopy, and compared to sham control, we observed (as shown with the red bars in FIG. 31), that both short and long-duration sciatic nerve damage leads to a robust increase in CCL2 expression in the dorsal spinal cord. The data of FIG. 32 also indicate that, compared to non-neuropathic sham-treated animals, again as shown in red, IL-10 immunoreactive levels are significantly reduced in the early and ongoing neuropathy. When IL-10 is elevated, pain is controlled.

Based on this overall profile of spinal leukocyte accumulation and increased spinal cord LFA-1 activation, we investigated whether blocking spinal LFA-1 activation could reduce leukocyte accumulation, and in doing so, suppress neuropathic pain. We used the LFA-1 specific antagonist, NorBIRT to prevent LFA-1 conformational changes, and we administered it intrathecally—around the spinal cord. BL responses occurred at 5 grams of touch stimuli, and CCI led to clear allodynia by day. An i.t injection of NorBIRT was administered, and compared to saline injected animals, as shown in the black symbols of FIG. 34, 5 ng NorBIRT very modestly reversed allodynia by day. However, as shown FIG. 35, a 10-fold higherdose of NorBIRT resulted in a substantial reversal of allodynia, with allodynia returning by day 9. We also observed that blocking leukocyte accumulation with i.t. NorBIRT reversed a 45-day enduring allodynia. Compared to sham controls, as shown in blue, and a low dose of NorBIRT when given i.t. on Day 45, a higher dose of i.t. NorBIRT on day 45, as shown in red, again substantially reversed ongoing allodynia. Together, these data suggest that active and ongoing leukocyte actions are occurring within the intrathecal region.

We also determined that an intravenous NorBIRT could alter ongoing allodynia. Following BL responses, and CCI, rats received either saline or 500 ng i.v. NorBIRT. Compared to the saline injected rats, by 48 and 72 hrs later, a significant change in allodynia was observed as shown in FIG. 35. We then SPECT imaged all of the rats (for minor technical reasons, saline-injected rats were not tested though day 6 when they were SPECT imaged). A subsequent group of CCI saline injected rats show no change from allodynia.

Figure 36:
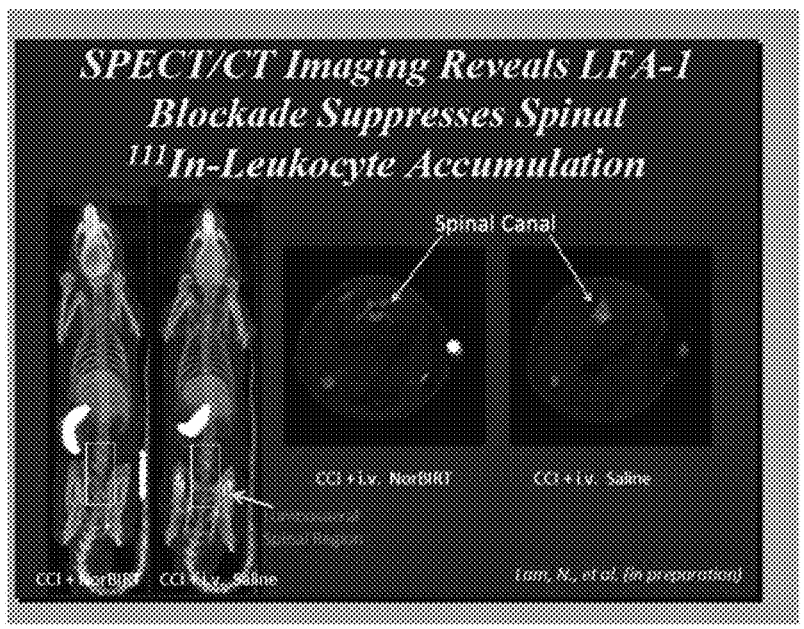
FIG. 36: SPECT/CT imaging reveals LFA-1 blockade suppresses spinal $^{111}$In-leukocyte accumulation, as determined in the experiments of Example 10.
Figure 37:
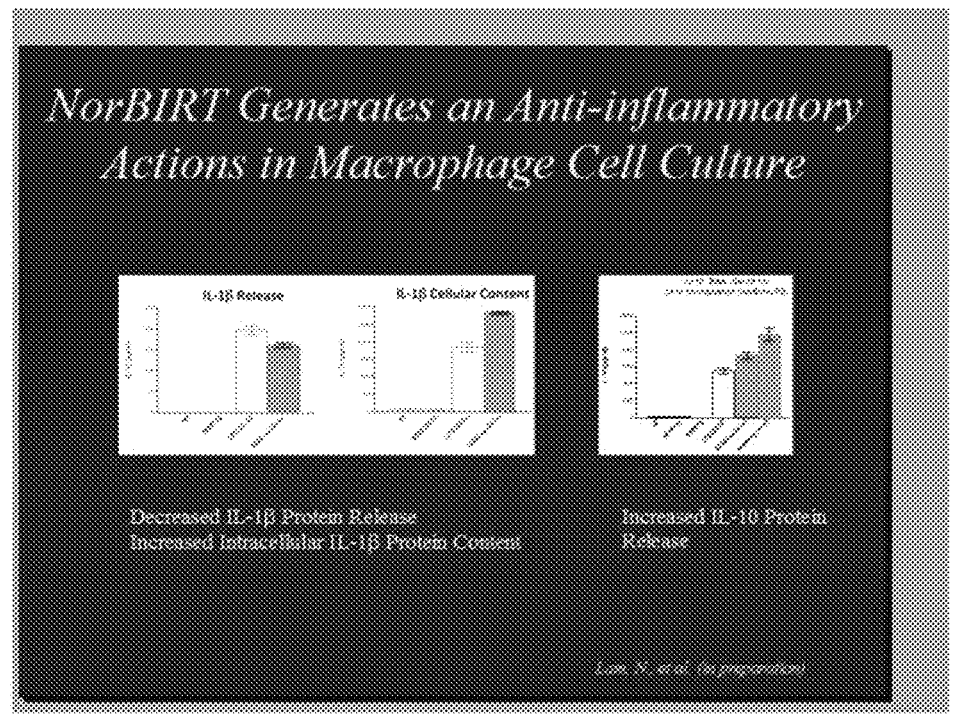
FIG. 37: NorBIRT generates anti-inflammatory actions in macrophage cell culture, as determined in the experiments of Example 10.

In behaviorally verified rats, in the lumbosacral spinal canal region of CCI+ saline injected rats, it was observed that substantially greater leukocyte accumulation is present compared to the NorBIRT injected rats. The right panels of FIG. 36 are the corresponding cross-section from these whole body images, which clearly identify that uCi signal is present in the saline controls from the canal and not of the surrounding tissues, while no signal is present from the NorBIRT treatment. Collectively, these data suggest an active neuroimmune interaction both early and long after initial peripheral nerve damage.

Given the intriguing profile of NorBIRT's actions on reversing allodynia, we examined whether NorBIRT additionally altered proinflammatory cytokine levels. Using RAW264.7 macrophage cell cultures, we found that, compared to various control treatments, LPS stimulation (gram negative bacterial cell wall particles) induced a robust increase in IL-1b release, while treatment with NorBIRT attenuated this increase. Intracellular IL-1b requires enzymatic cleavage to produce the mature released form. Here, we see intracellular IL-1b is substantially increased with NorBIRT treatment. Thus NorBIRT is blocking the release of mature IL-1b. We also found that compared to control treatments, NorBIRT dose-dependently increased IL-10 protein release following LPS stimulation. So, NorBIRT may additionally have anti-inflammatory properties.

Example 11

Enduring Involvement of Immune Cell Leukocytes in the Lumbar Spinal Region During Chronic Peripheral Neuropathy in Rats Data Analysis Psychometric behavioral analysis was performed as previously described [55] to compute the log stiffness that would have resulted in the 50% paw withdrawal rate. Briefly, thresholds were estimated by fitting a Gaussian integral psychometric function to the observed withdrawal rates for each of the tested von Frey hairs, using a maximum-likelihood fitting method [90].

All statistical comparisons were computed using Prism v6.0c (GraphPad Software Inc., San Diego, Calif.) for Macintosh. Data from the von Frey test were analyzed as the interpoloated 50% threshold (absolute threshold) in log base 10 of stimulus intensity (monofilament stiffness in milligrams X 10). Pre-surgery baseline (BL) measures were analyzed by one-way ANOVA. Post-surgery and post-drug time course measures were analyzed by repeated measures two-way ANOVAs followed by Fisher's protected least significant difference or Holm-Sidak multiple t-test for post-hoc comparisons, where noted. All data is expressed as mean+/−SEM. Mean differences from SPECT/CT scans revealing microcurie activity, microscopy analysis and biological samples from cell culture and were analyzed using one-way ANOVA.

Results

Intrathecal Injection of NorBIRT

The LFA-1 antagonist, NorBIRT, reverses a 10-day allodynia produced by CCI. Prior to surgical manipulation, all groups exhibited similar bilateral (ipsilateral and contralateral) BL behavioral thresholds (ipsilateral hindpaw ANOVA, $F_{(3,18)}$=1.166, p>0.35; contralateral hindpaw ANOVA, $F_{(3,18)}$=0.2473, p=0.8622). Following CCI, clear bilateral allodynia developed by Day 3 and continued through to Day 10 compared to sham-operated rats (ipsilateral hindpaw ANOVA, $F_{(3,18)}=43.77$, $p<0.0001$; contralateral hindpaw ANOVA, $F_{(3,18)}=13.26$, $p<0.0001$). Compared to sham-operated rats, i.t. vehicle-injected rats remained allodynic (ipsilateral hindpaw ANOVA, $F_{(1,8)}=216.6$, $p<0.0001$; contralateral hindpaw ANOVA, $F_{(1,8)}=49.74$, $p=0.0001$) without significant change through the 10 days post injection (ipsilateral hindpaw ANOVA, $F_{(10,80)}=1.088$, $p=0.3816$; contralateral hindpaw ANOVA, $F_{(10,80)}=13.26$, $p=0.8450$).

Figure 38:
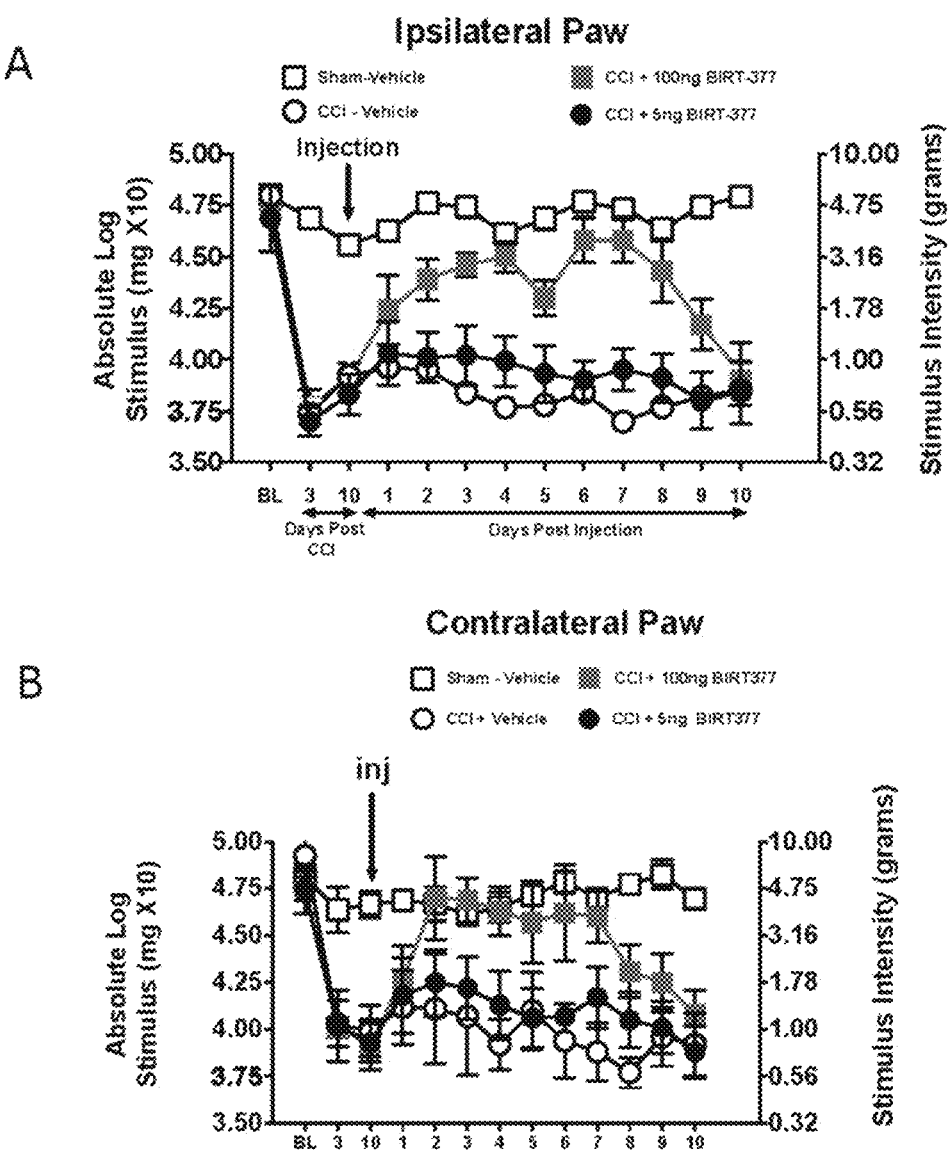
FIGS. 38A and B: This shows that intrathecal (peri-spinal/subarachnoid) injection of NorBIRT reverses CCI-induced mechanical allodynia in a dose depended manner after 10 days. Figure A shows the effect on the ipsilateral paw and B shows the effect on the contralateral paw.

Following i.t. treatment, overall analysis revealed that compared to i.t. vehicle, rats given i.t. NorBIRT reversed from bilateral allodynia (ipsilateral hindpaw ANOVA, $F_{(20,130)}=1.873$, $p=0.0194$; contralateral hindpaw ANOVA, $F_{(20,130)}=1.771$, $p=0.0303$), with allodynia fully returned by Day 10 (ipsilateral hindpaw ANOVA, $F_{(2,13)}=0.3835$, $p=0.6889$ FIG. 38A; contralateral hindpaw ANOVA, $F_{(2,13)}=3.060$, $p=0.0815$) compared to sham controls (ipsilateral hindpaw ANOVA, $F_{(3,18)}=28.49$, $p<0.0001$; contralateral hindpaw ANOVA, $F_{(3,18)}=36.67$, $p<0.0001$) FIG. 38B.

NorBIRT dose-dependently altered allodynia, with the low dose of NorBIRT (5 ng) lacking effects compared to vehicle injected rats (ipsilateral hindpaw ANOVA, $F_{(1,8)}=0.9237$; $p=0.3646$; contralateral hindpaw ANOVA, $F_{(1,8)}=0.4524$; $p=0.5201$), while the higher dose of NorBIRT (100 ng) produced a dramatic reversal from allodynia compared to vehicle injected rats (ipsilateral hindpaw ANOVA, $F_{(1,8)}=39.00$, $p=0.0002$; contralateral hindpaw ANOVA, $F_{(1,8)}=15.01$, $p=0.0047$). Peak effect was observed four days after injection of NorBIRT when compared to sham controls (Multiple t-test using Holm-Sidak Method; ipsilateral hindpaw P=0.233866, contralateral hindpaw P=0.846681). See FIG. 38A (ipsilateral hindpaw), 38B (contralateral hindpaw).

Intravenous Injection of NorBIRT

Intravenous (i.v.) injection of NorBIRT at relatively high doses reverses CCI-induced mechanical allodynia in a dose depended manner after 10 days. The LFA-1 anatgonist reversed allodynia produced by CCI. Prior to surgical manipulation, all groups exhibited similar bilateral (ipsilateral and contralateral) BL behavioral thresholds (ipsilateral paw ANOVA, $F_{(3,15)}=4.842$; $p=0.8953$; contralateral paw ANOVA, $F_{(3,15)}=2.463$ $p=0.1025$). Following CCI, clear bilateral allodynia developed by Day 3 and continued through to Day 10 compared to sham-operated rats (ipsilateral paw 2 way ANOVA, $F_{(3,15)}=59.72$; $p<0.0001$; contralateral paw 2 way ANOVA, $F_{(3,15)}=21.28$; $p<0.0001$). On Day 10, compared to uninjected rats, NorBIRT produced a dose-dependent reversal from allodynia for four days following the highest injected dose (100 000 ng) (ipsilateral paw 2 way ANOVA, $F_{(3,15)}=73.22$; $p<0.0001$, FIG. 39A; contralateral paw 2 way ANOVA, $F_{(3,15)}=35.83$; $p<0.0001$) FIG. 39B. 100 000 ng and 5000 ng produced attenuated allodynia bilaterally.

An experiment with low dose intravenous injection showed that NorBIRT at low dose did not reverse CCI-inducted mechanical allodynia after 10 days. Prior to surgical manipulation, all groups exhibited similar BL behavioral thresholds in their ipsilateral paw (ipsilateral paw ANOVA, $F_{(5,26)}=2.090$; $p=0.0990$; contralateral paw ANOVA, $F_{(5,26)}=3.136$ $p=0.0240$). Following CCI, clear bilateral allodynia developed by Day 3 and continued through to Day 10 compared to sham-operated rats (ipsilateral paw ANOVA, $F_{(4,21)}=0.9919$; $p=0.4336$; contralateral paw ANOVA, $F_{(4,21)}=1.628$; $p=0.1926$). At 5 days after the injection, NorBIRT did not produce a does-dependent reversal from allodynia (ipsilateral paw 2-way ANOVA, $F_{(5,26)}=25.54$; $p<0.0001$, FIG. 40A; contralateral paw ANOVA, $F_{(5,26)}=30.27$; $p<0.0001$), FIG. 40B. Throughout the 8 days after injection, compared to Sham rats, NorBIRT does not produce a dose-dependent reversal from allodynia (ipsilateral paw 2 way ANOVA, $F_{(4,24)}=45.42$; $p<0.0.0001$; contralateral paw 2 way ANOVA, $F_{(4,24)}=42.24$; $p<0.0001$).

What is claimed is:

1. A method of treating chronic neuropathic pain or chronic neuropathic pain in combination with allodynia in a subject in need comprising administering to said subject a therapeutically-effective amount of a composition comprising a LFA1 antagonist wherein said LFA1 antagonist is a compound according to the chemical structure:

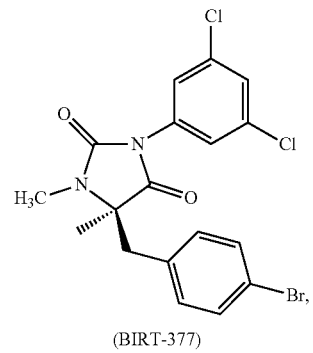 [SMILES: CN1C(=O)N(c2cc(Cl)cc(Cl)c2)C(=O)[C@@]1(C)Cc1ccc(Br)cc1]

(BIRT-377)

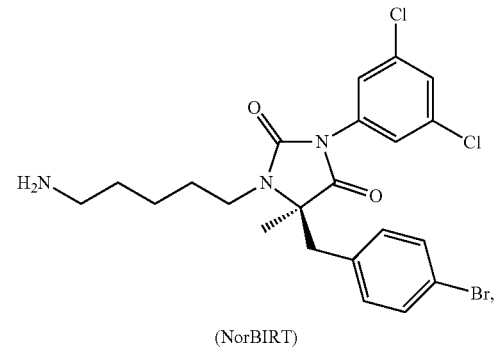 [SMILES: C[C@@]1(Cc2ccc(Br)cc2)C(=O)N(c2cc(Cl)cc(Cl)c2)C(=O)N1CCCCCN]

(NorBIRT)

a mixture thereof, or a pharmaceutically acceptable salt, stereoisomer, solvate or polymorph thereof, and wherein said LFA1 antagonist(s) is the only therapeutic agent useful for treating chronic neuropathic pain in said composition.

2. The method according to claim 1 which treats chronic neuropathic pain.

3. The method according to claim 2 wherein said neuropathic pain is peripheral neuropathic pain.

4. The method according to claim 1 wherein said LFA1 antagonist is BIRT-377 or a mixture of BIRT-377 and NorBIRT.

5. The method according to claim 1 wherein said LFA1 antagonist is BIRT-377.

6. The method according to claim 2 wherein said LFA1 antagonist is BIRT-377.

7. The method according to claim 3 wherein said LFA1 antagonist is BIRT-377.

8. The method according to claim 1 wherein said LFA1 antagonist is administered to said subject orally.

9. The method according to claim 1 wherein said LFA1 antagonist is administered to said subject parenterally.

10. The method according to claim 1 wherein said LFA1 antagonist is administered to said subject intrathecally.

11. The method according to claim 4 wherein said LFA1 antagonist is administered to said subject orally.

12. The method according to claim 4 wherein said LFA1 antagonist is administered to said subject parenterally.

13. The method according to claim 4 wherein said LFA1 antagonist is administered to said subject intrathecally.

14. The method according to claim 5 wherein said LFA1 antagonist is administered to said subject orally.

15. The method according to claim 5 wherein said LFA1 antagonist is administered to said subject parenterally.

16. The method according to claim 5 wherein said LFA1 antagonist is administered to said subject intrathecally.

17. The method according to claim 6 wherein said LFA1 antagonist is administered to said subject orally.

18. The method according to claim 6 wherein said LFA1 antagonist is administered to said subject parenterally.

19. The method according to claim 6 wherein said LFA1 antagonist is administered to said subject intrathecally.

20. The method according to claim 7 wherein said LFA1 antagonist is administered to said subject orally.

21. The method according to claim 7 wherein said LFA1 antagonist is administered to said subject parenterally.

22. The method according to claim 7 wherein said LFA1 antagonist is administered to said subject intrathecally.

23. A method of treating chronic neuropathic pain or chronic neuropathic pain in combination with allodynia in a subject in need comprising administering to said subject a therapeutically-effective amount of a composition comprising a LFA1 antagonist wherein said LFA1 antagonist is a compound according to the chemical structure:

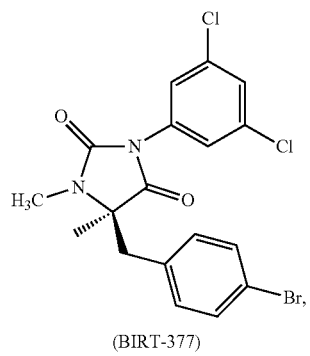 [SMILES: CN1C(=O)N(c2cc(Cl)cc(Cl)c2)C(=O)[C@@]1(C)Cc1ccc(Br)cc1]

(BIRT-377)

or a pharmaceutically acceptable salt, stereoisomer, solvate or polymorph thereof, and wherein said LFA1 antagonist is the only therapeutic agent useful for treating chronic neuropathic pain in said composition.

24. The method according to claim 23 wherein said neuropathic pain is peripheral neuropathic pain and said composition is administered to said patient intravenously or intrathecally.

25. The method according to claim 23 wherein said LFA1 antagonist is BIRT-377 and said method treats chronic neuropathic pain.

26. The method according to claim 24 wherein said LFA1 antagonist is BIRT-377.

* * * * *